United States Patent
Han et al.

(10) Patent No.: US 12,168,677 B2
(45) Date of Patent: *Dec. 17, 2024

(54) PROTEINS FOR THE TREATMENT OF EPITHELIAL BARRIER FUNCTION DISORDERS

(71) Applicant: Genevive, Inc., San Mateo, CA (US)

(72) Inventors: Andrew Wonhee Han, Brisbane, CA (US); Andrew W. Goodyear, Brisbane, CA (US); Tarunmeet Gujral, Brisbane, CA (US); Todd Zachary DeSantis, Brisbane, CA (US); Karim Dabbagh, Brisbane, CA (US)

(73) Assignee: Genevive, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/354,372

(22) Filed: Jul. 18, 2023

(65) Prior Publication Data
US 2024/0076323 A1    Mar. 7, 2024

Related U.S. Application Data

(63) Continuation of application No. 17/526,970, filed on Nov. 15, 2021, now abandoned, which is a continuation of application No. 16/618,499, filed as application No. PCT/US2018/035682 on Jun. 1, 2018, now Pat. No. 11,174,293.

(60) Provisional application No. 62/518,138, filed on Jun. 12, 2017, provisional application No. 62/518,137, filed on Jun. 12, 2017, provisional application No. 62/514,165, filed on Jun. 2, 2017, provisional application No. 62/514,148, filed on Jun. 2, 2017.

(51) Int. Cl.

| | |
|---|---|
| *C07K 14/195* | (2006.01) |
| *A61K 38/16* | (2006.01) |
| *A61K 45/06* | (2006.01) |
| *A61P 1/04* | (2006.01) |
| *C12N 1/20* | (2006.01) |
| *C12N 5/07* | (2010.01) |
| *C12N 15/70* | (2006.01) |
| *C12N 15/85* | (2006.01) |

(52) U.S. Cl.
CPC .......... *C07K 14/195* (2013.01); *A61K 38/164* (2013.01); *A61K 45/06* (2013.01); *A61P 1/04* (2018.01); *C12N 1/20* (2013.01); *C12N 5/06* (2013.01); *C12N 15/70* (2013.01); *C12N 15/85* (2013.01)

(58) Field of Classification Search
CPC .......................... C07K 14/195; A61K 38/164
See application file for complete search history.

(56) References Cited

U.S. PATENT DOCUMENTS

| | | |
|---|---|---|
| 4,399,216 A | 8/1983 | Axel |
| 5,767,063 A | 6/1998 | Lee |
| 11,174,293 B2 * | 11/2021 | Han ........................ A61P 1/04 |
| 2002/0052336 A1 | 5/2002 | Yerxa |
| 2005/0100531 A1 | 5/2005 | Bienenstock |
| 2008/0311097 A1 | 12/2008 | Israelsen |
| 2015/0258151 A1 | 9/2015 | Mani |
| 2016/0143962 A1 | 5/2016 | Berry |
| 2020/0181206 A1 | 6/2020 | Han |
| 2022/0106365 A1 | 4/2022 | Han |

FOREIGN PATENT DOCUMENTS

WO    WO 2016/141108    9/2016

OTHER PUBLICATIONS

MAG: trigger factor (GenBank: MED9972910.1) (Year: 2024).*
Protease complex subunit PrcB family protein (GenBank: WP_117914106.1) (Year: 2020).*
Trigger factor (plasmid) [[Eubacterium] eligens ATCC 27750] GenBank: ACR73640.1 (Year: 2017).*
Altschul et al., "Basic local alignment search tool," Journal of molecular biology, Oct. 5, 1990, 215(3):403-410.
Altschul et al., "Gapped BLAST and PSI-BLAST: a new generation of protein database search programs," Nucleic acids research, Sep. 1, 1997, 25(17):3389-3402.
Antonsson et al., "Induction of Apoptosis by Staurosporine Involves the Inhibition of Expression of the Major Cell Cycle Proteins at the G2/M Checkpoint Accompanied by Alterations in Erk and Akt Kinase Activities," Anticancer research, Aug. 1, 2009, 29(8):2893-2898.
Aroniadis et al., "Fecal microbiota transplantation: past, present and future," Current opinion in gastroenterology, Jan. 1, 2013, 29(1):9 Pages.
atum.bio [online], "GPS Technology," retrieved on Jun. 16, 2020, retrieved from URL< www.atum.bio/services/genegps>, 5 pages.
Ayoubi et al., "Regulation of gene expression by alternative promoters.," The FASEB Journal, Mar. 1996, 10(4):9 Pages.
Baron et al., "Variation Between Observers in Describing Mucosal Appearances in Proctocolitis," British medical journal, Jan. 11, 1964, 1(5375):89-92.
Beduneau et al., "A tunable Caco-2/HT29-MTX co-culture model mimicking variable permeabilities of the human intestine obtained by an original seeding procedure," European Journal of Pharmaceutics and Biopharmaceutics, Jul. 1, 2014, 87(2):9 Pages.

(Continued)

*Primary Examiner* — Lianko G Garyu
(74) *Attorney, Agent, or Firm* — Fish & Richardson P.C.

(57) ABSTRACT

The disclosure relates to therapeutic proteins and pharmaceutical compositions comprising said proteins, which have utility in treating various human diseases. In particular aspects, the disclosed therapeutic proteins are useful for treating human gastrointestinal inflammatory diseases and gastrointestinal conditions associated with decreased epithelial cell barrier function or integrity. Further, the disclosed therapeutic proteins are useful for treating human inflammatory bowel disease, including inter alia, Crohn's disease and ulcerative colitis.

18 Claims, 26 Drawing Sheets

Specification includes a Sequence Listing.

(56) References Cited

OTHER PUBLICATIONS

Berge et al., "Pharmaceutical Salts," Journal of pharmaceutical sciences, Jan. 1, 1977, 66(1): 1-19.
Berger et al., "Oleic Acid Uptake Reveals the Rescued Enterocyte Phenotype of Colon Cancer Caco-2 by HT29-MTX Cells in Co-Culture Mode," International journal of molecular sciences, Jul. 2017, 18(7):21 Pages.
Best et al., "Development of a Crohn's disease activity index.," National Cooperative Crohn's Disease Study, Gastroenterol, Mar. 1, 1976, 70(3): 439-444.
Bibiloni et al., "VSL#3 Probiotic-Mixture Induces Remission in Patients with Active Ulcerative Colitis," Am J Gastroenterol, Jul. 1, 2005, 100(7): 9 Pages.
Boltin et al., "Mucin Function in Inflammatory Bowel Disease: An Update," Journal of clinical gastroenterology, Feb. 1, 2013, 47(2):106-111.
Botoman et al., "Management of Inflammatory Bowel Disease," American family physician, Jan. 1, 1998, 57(1):7 Pages.
Bowie et al., "Deciphering the message in protein sequences: tolerance to amino acid substitutions," Science, Mar. 16, 1990, 247(4948):1306-1310.
Bratt et al., A phase 1 trial with transgenic bacteria expressing interleukin-IO in Crohn's disease; Clinical Gastroenterology and Hepatology, 2006, 4:754-759.
Cani et al., "Changes in Gut Microbiota Control Metabolic Endotoxemia-Induced Inflammation in High-Fat Diet-Induced Obesity and Diabetes in Mice," Diabetes, Jun. 1, 2008, 57(6):1470-1481.
Chassaing et al., "Dextran sulfate sodium (DSS)-induced colitis in mice," Current protocols in immunology, Feb. 2014, 104(1):15-25.
Collins et al., "Finishing the euchromatic sequence of the human genome.," International Human Genome Sequencing Consortium, Nature, 431(7011):4 Pages.
Coskun, "Intestinal epithelium in inflammatory bowel disease," Frontiers in Medicine, Aug. 25, 2014, 1:24, 5 pages.
Danese et al., "Etiopathogenesis of inflammatory bowel diseases," World journal of gastroenterology: WJG, Aug. 14, 2006, 12(30):4807-4812.
Delzenne et al., "Targeting gut microbiota in obesity: effects of prebiotics and probiotics," Nature Reviews Endocrinology, Nov. 2011, 7(11):9 Pages.
Dewi et al., "In vitro assessment of human endothelial cell permeability: effects of inflammatory cytokines and dengue virus infection," Journal of virological methods, Nov. 1, 2004, 121(2):171-180.
Dewi et al., "Peripheral blood mononuclear cells increase the permeability of dengue virus-infected endothelial cells in association with downregulation of vascular endothelial cadherin," Journal of General Virology, Mar. 1, 2008, 89(3):642-652.
Duncan et al., "Proposal of *Roseburia faecis* sp. nov., *Roseburia hominis* sp. nov. and *Roseburia inulinivorans* sp. nov., based on isolates from human faeces," International journal of systematic and evolutionary microbiology, Oct. 1, 2006, 56(10):2437-2441.
Durrer et al., "Genetically engineered probiotic for the treatment of phenylketonuria (PKU); assessment of a novel treatment in vitro and in the PAHenu2 mouse model of PKU," PloS one, May 17, 2017, 12(5):17 Pages.
Everard et al., "Cross-talk between Akkermansia muciniphila and intestinal epithelium controls diet-induced obesity," Proceedings of the national academy of sciences, May 28, 2013, 110(22):9066-9071.
Everard et al., "Responses of Gut Microbiota and Glucose and Lipid Metabolism to Prebiotics in Genetic Obese and Diet-Induced Leptin-Resistant Mice," Diabetes, Nov. 1, 2011, 60(11):2775-2786.
Gassler et al., "Inflammatory bowel disease is associated with changes of enterocytic junctions," American Journal of Physiology-Gastrointestinal and Liver Physiology, Jul. 1, 2001, 281(1):G216-G228.
Gaston et al., "S-Nitrosylation Signaling in Cell Biology," Molecular interventions, Aug. 1, 2003, 3(5):253-263.

GenBank Accession No. FUXV01000001, "Intestinibacter bartlettii DSM 16795 genome assembly, contig: EJ10DRAFT_scaffold00001.1, whole genome shotgun sequence," Mar. 4, 2017, 199 pages.
GenBank Accession No. NR 074613, "[Eubacterium] eligens ATCC 27750 16S ribosomal RNA, partial sequence," Mar. 12, 2019, 2 pages.
GenBank Accession No. ACR73640, 2017.
GenBank Accession No. CP001104, "[Eubacterium] eligens ATCC 27750 chromosome, complete genome," Aug. 25, 2017, 311 pages.
GenBank Accession No. SKA51491, 2017.
GenBank Accession No. WP 007286875.1, 2019.
genscript.com [online], "OptimumGene—Codon Optimization," retrieved Jun. 17, 2020, GenScript: www.genscript.com/codon-opt.html, 5 pages.
Glozak et al., "Acetylation and deacetylation of non-histone proteins," Gene, Dec. 19, 2005, 363:15-23.
Han et al., "Detergent-free biotin switch combined with liquid chromatography/tandem mass spectrometry in the analysis of S-nitrosylated proteins," Rapid Communications in Mass Spectrometry: An International Journal Devoted to the Rapid Dissemination of Up-to-the-Minute Research in Mass Spectrometry, Apr. 30, 2008, 22(8):1137-1145.
Hanniffy et al., "Mucosal Delivery of a Pneumococcal Vaccine Using Lactococcus lactis Affords Protection against Respiratory Infection," The Journal of infectious diseases, Jan. 15, 2007, 195(2):185-193.
Harvey et al., "Methods and Devices, A Simple Index of Crohn's-Disease Activity," The Lancet, Mar. 8, 1980, 315(8167):514.
Henikoff et al, "Amino acid substitution matrices from protein blocks," Proceedings of the National Academy of Sciences, Nov. 15, 1992, 89(22):10915-10919.
Higgins et al., "CLUSTAL: a package for performing multiple sequence alignment on a microcomputer," Gene, Dec. 15, 1988, 73(1):237-244.
Holdeman et al., "New Genus, Coprococcus, Twelve New Species, and Emended Descriptions of Four Previously Described Species of Bacteria from Human Feces," International Journal of Systematic and Evolutionary Microbiology, Apr. 1, 1974, 24(2):260-277.
hopkinsmedicine.org [online], Ulcerative Colitis: Introduction Johns Hopkins Medicine, 2013, retrevied Mar. 30, 2020, retrieved from URL <www.hopkinsmedicine.org/gastroenterology_ hepato logy/_pdfs/small_largeintestine/ulcerative_colitis.pdf>, 14 pages.
Horhota et al., "Glycerol Nucleoside Triphosphates: Synthesis and Polymerase Substrate Activities," Organic letters, Nov. 9, 2006, 8(23):5345-5347.
Hsiao et al., "High-frequency transformation of yeast by plasmids containing the cloned yeast ARG4 gene," Proceedings of the National Academy of Sciences, Aug. 1, 1979, 76(8):3829-3833.
Huynh et al., "Probiotic Preparation VSL#3 Induces Remission in Children with Mild to Moderate Acute Ulcerative Colitis: A Pilot Study," Inflammatory bowel diseases, May 1, 2009, 15(5):760-768.
Imai et al., "Transcriptional silencing and longevity protein Sir2 is an NAD-dependent histone deacetylase," Nature, Feb. 2000, 403:795-800.
Irvine et al., "Quality of life: A valid and reliable measure of therapeutic efficacy in the treatment of inflammatory bowel disease," Gastroenterology, Feb. 1, 1994, 106(2): 287-296.
IUPAC, Commission on the Nomenclature of Organic Chemistry (CNOC) and IUPAC-IUB Commission on Biochemical "Nomenclature of α-amino acids. (Recommendations, 1974)," Biochemistry, Jan. 1, 1975, 14(2):449-462.
Jaffrey et al., "The Biotin Switch Method for the Detection of S-Nitrosylated Proteins," Science's STKE, Jun. 12, 2001, (86):10 Pages.
Jensen, "Modification-specific proteomics: characterization of post-translational modifications by mass spectrometry," Curr Opin Chem Biology, Feb. 1, 2004, 8(1):33-41.
Johansson et al., "Bacteria penetrate the normally impenetrable inner colon mucus layer in both murine colitis models and patients with ulcerative colitis," Gut, Feb. 1, 2014, 63(2):281-291.
Karlin et al., "Applications and statistics for multiple high-scoring segments in molecular sequences," Proceedings of the National Academy of Sciences, Jun. 15, 1993, 90(12):5873-5877.

(56) References Cited

OTHER PUBLICATIONS

Kiesler et al., "Experimental Models of Inflammatory Bowel Diseases," Cellular and molecular gastroenterology and hepatology, Mar. 1, 2015, 1(2):154-170.
Kim et al., "Investigating Intestinal Inflammation in DSS-induced Model of IBD," Journal of Visualized Experiments, Feb. 1, 2012, 1(60):6 Pages.
Kyte et al., "A Simple Method for Displaying the Hydropathic Character of a Protein," Journal of molecular biology, May 5, 1982, 157(1):105-132.
Lerner et al., "Dysbiosis May Trigger Autoimmune Diseases via Inappropriate Post-Translational Modification of Host Proteins," Frontiers in Microbiology, Feb. 5, 2016, 7:84, 6 pages.
Levesque et al., "Converging goals of treatment of inflammatory bowel disease from clinical trials and practice," Gastroenterology, Jan. 1, 2015, 148(1):37-51.
Machiels et al., "A decrease of the butyrate-producing species *Roseburia hominis* and *Faecalibacterium prausnitzii* defines dysbiosis in patients with ulcerative colitis," Gut, Aug. 1, 2014, 63(8):1275-1283.
Maloy et al., "Intestinal homeostasis and its breakdown in inflammatory bowel disease," Nature, Jun. 2011, 474(7351):298-306.
Mandic et al., "Evaluation of head and neck squamous cell carcinoma invasiveness by the electrical resistance breakdown assay, " Clinical & experimental metastasis, Jun. 1, 2005, 21(8):699-704.
Mansour et at., "Disruption of the proto-oncogene int-2 in mouse embryo-derived stem cells: a general strategy for targeting mutations to non-selectable genes," Nature, Nov. 24, 1988, 336(6197):348-352.
March et al., "The DNA sequence of the gene (rnc) encoding ribonuclease III of *Escherichia coli*," Nucleic acids research, Jul. 11, 1985,13(13):4677-4685.
Martini et al., "Mend Your Fences: The Epithelial Barrier and its Relationship With Mucosal Immunity in Inflammatory Bowel Disease," Cellular and molecular gastroenterology and hepatology, Jul. 1, 2017, 4(1):33-46.
Matts, "The value of rectal biopsy in the diagnosis of ulcerative colitis," QJM, 1961, 30: 393-407.
Merrifield, "Solid Phase Peptide Synthesis. I. The Synthesis of a Tetrapeptide," Journal of the American Chemical Society, Jul. 1963, 85(14):2149-2154.
Moayyedi et al., "Fecal Microbiota Transplantation Induces Remission in Patients With Active Ulcerative Colitis in a Randomized Controlled Trial," Gastroenterology, Jul. 1, 2015, 149(1):102-109.
Molodecky et al., Increasing incidence and prevalence of the inflammatory bowel diseases with time, based on systematic review, Gastroenterology, Jan. 1, 2012, 142(1):51 Pages.
Myers et al., "Optimal alignments in linear space," Bioinformatics, Mar. 1, 1988, 4(1):11-17.
Narula et al., "Systematic Review and Meta-analysis: Fecal Microbiota Transplantation for Treatment of Active Ulcerative Colitis," Inflammatory bowel diseases, Oct. 1, 2017, 23(10):1702-1709.
NCBI Reference Sequence: WP_041687898.1, 2015.
NCBI Reference Sequence: WP_041688962.1, 2015.
NCBI Reference Sequence: WP_055216081.1, 2015.
Needleman et al., "A General Method Applicable to the Search for Similarities in the Amino Acid Sequence of Two Proteins," Journal of Molecular Biology Mar. 28, 1970, 48(3):444-453.
Neurath, "Cytokines in inflammatory bowel disease," Nature Reviews Immunology, May 2014, 14(5):329-342.
Paine, "Colonoscopic evaluation in ulcerative colitis," Gastroenterology report, Aug. 1, 2014, 2(3):161-168.
Pan et al., "Oral administration of Lactobacillus paracasei alleviates clinical symptoms of colitis induced by dextran sulphate sodium salt in BALB/c mice," Beneficial Microbes, Sep. 1, 2014, 5(3):315-322.
Patterson et al., "Human Gut Symbiont Roseburia hominis Promotes and Regulates Innate Immunity," Frontiers in immunology, Sep. 26, 2017, 8:1166, 14 pages.
PCT International Preliminary Report in Patentability in International Appln. No. PCT/US2018/035682, dated Aug. 30, 2018, 9 pages.
PCT International Search Report and Written Opinion in International Appln. No. PCT/US18/35682, dated Oct. 19, 2018, 16 pages.
Pearson et al., "Improved tools for biological sequence comparison," Proceedings of the National Academy of Sciences, Apr. 1, 1988, 85(8):2444-2448.
Plovier et al., "A purified membrane protein from Akkermansia muciniphila or the pasteurized bacterium improves metabolism in obese and diabetic mice," Nature medicine., Jan. 2017, 23(1):107-113.
Plyum et al., "Heme binding properties of *Staphylococcus aureus* IsdE," Biochemistry, 2007, 12777-12787.
Qazi et al., "The risk of inflammatory bowel disease flares after fecal microbiota transplantation: Systematic review and meta-analysis," Gut Microbes, Nov. 2, 2017, 8(6):16 Pages.
Rachmilewitz, "Coated mesalazine (5-aminosalicylic acid) versus sulphasalazine in the treatment of active ulcerative colitis: a randomised trial," British Medical Journal, Jan. 14, 1989, 298(6666):82-86.
Sands et al., "Infliximab Maintenance Therapy for Fistulizing Crohn's Disease," New England Journal of Medicine, Feb. 26, 2004, 350(9):876-885.
Sands, "From symptom to diagnosis: clinical distinctions among various forms of intestinal inflammation," Gastroenterology, May 1, 2004, 126(6): 1518-1532.
Schroeder et al., "Coated Oral 5-Aminosalicylic Acid Therapy for Mildly to Moderately Active Ulcerative Colitis," N Engl J Med, Dec. 24, 1987, 317(26):1625-1629.
Shawki et al., "Mechanisms of Intestinal Epithelial Barrier Dysfunction by Adherent-Invasive *Escherichia coli*," Cellular and molecular gastroenterology and hepatology, Jan. 1, 2017, 3(1):41-50.
Sheth et al., "Manipulating bacterial communities by in situ microbiome engineering," Trends in Genetics, Apr. 1, 2016, 32(4):22 Pages.
Shigemori et al., "Oral delivery of Lactococcus lactis that secretes bioactive heme oxygenase-1 alleviates development of acute colitis in mice," Microbial Cell Factories, Dec. 1, 2015, 14(1):12 Pages.
Simmonds et al., "Paneth cell metaplasia in newly diagnosed inflammatory bowel disease in children," BMC Gastroenterol, Dec. 14, 2014, 14(1):6 Pages.
Srinivasan et al., "TEER measurement techniques for in vitro barrier model systems," Journal of laboratory automation, Apr. 2015, 20(2):35 Pages.
Srutkova et al., "Bifidobacterium longum CCM 7952 Promotes Epithelial Barrier Function and Prevents Acute DSS-Induced Colitis in Strictly Strain-Specific Manner." PLoS One, Jul. 28, 2015, 10(7):20 Pages.
Steidler et al., "Treatment of Murine Colitis by Lactococcus lactis Secreting Interleukin-10," Science, Aug. 25, 2000, 259(5483):1352-1355.
Strober et al., Proinflammatory Cytokines in the Pathogenesis of Inflammatory Bowel Diseases, Gastroenterology May 1, 2011, 140(6):1756-1767.
Sutherland et al., "5-aminosalicylic acid enema in the treatment of distal ulcerative colitis, proctosigmoiditis, and proctitis," Gastroenterology, 1987, 92: 1994-1998.
ThermoFisher.com [online], "Invitrogen GeneArt Gene Synthesis," 2017, retrieved on Jun. 18, 2020, retrieved from URL <www.thermofisher.com/us/en/home/life-science/cloning/genesynthesis/geneart-gene-synthesis/geneoptimizerhtm>, 4 pages.
Thia et al., "Measurement of Disease Activity in Ulcerative Colitis: Interobserver Agreement and Predictors of Severity," Inflammatory bowel diseases, Jun. 2011, 17(6):8 Pages.
Travis et al., "Developing an instrument to assess the endoscopic severity of ulcerative colitis: the Ulcerative Colitis Endoscopic Index of Severity (UCEIS)," Gut, Apr. 1, 2012, 61(4):535-542.
UniProt.org [online], "C4Z2Y2_EUBE2," May 10, 2017, Retrieved from the Internet Jan. 27, 2020, retrevied from URL<https://www.uniprot.org/uniprot/C4Z2Y2>, dated Jul. 28, 2009, 3 pages.
Van Solingen et al., "Fusion of Yeast Spheroplasts," Journal of Bacteriology, May 1, 1977, 130(2):946-947.

(56) References Cited

OTHER PUBLICATIONS

Vandenbroucke et al., "Active delivery of trefoil factors by genetically modified Lactococcus lactis prevents and heals acute colitis in mice," Gastroenterology, Aug. 1, 2004, 127(2):502-513.
Yan et at, "Colon-specific delivery of a probiotic-derived soluble protein ameliorates intestinal inflammation in mice through an EGFR-dependent mechanism," The Journal of clinical investigation, Jun. 1, 2011, 121(6): 13 Pages.
Yang et al., "Lysine Acetylation: Codified Crosstalk with Other Posttranslational Modifications," Molecular cell, Aug. 22, 2008, 31(4):449-461.
Zhang et al., "Cytokines, Inflammation and Pain," International anesthesiology clinics, 2007, 45(2):10 Pages.
Zhang et al., "Interactions between Intestinal Microbiota and Host Immune Response in Inflammatory Bowel Disease," Frontiers in immunology, Aug. 14, 2017, 8(942): 13 Pages.
Zolotarevsky et al., "A Membrane-Permeant Peptide That Inhibits MLC Kinase Restores Barrier Function in In Vitro Models of Intestinal Disease," Gastroenterology, Jul. 1, 2002, 123(1):163-172.

\* cited by examiner

PROTEINS FOR THE TREATMENT OF EPITHELIAL BARRIER FUNCTION DISORDERS

CROSS-REFERENCE TO RELATED APPLICATIONS

This application is a Continuation application of U.S. application Ser. No. 17/526,970, filed on Nov. 15, 2021, which is a Continuation application of U.S. application Ser. No. 16/618,499, filed on Dec. 2, 2019, now U.S. Pat. No. 11,174,293, which is a National Stage Application under 35 U.S.C. § 371 and claims the benefit of International Application No. PCT/US2018/035682, filed on Jun. 1, 2018, which claims the benefit of priority to U.S. Provisional Application No. 62/514,165, filed on Jun. 2, 2017, U.S. Provisional Application No. 62/514,148, filed on Jun. 2, 2017, U.S. Provisional Application No. 62/518,137, filed on Jun. 12, 2017, and U.S. Provisional Application No. 62/518,138, filed on Jun. 12, 2017. Each of these applications is incorporated herein by reference in its entirety.

SEQUENCE LISTING

This application contains a Sequence Listing that has been submitted electronically as an XML file named "47192-0014003_SL_ST26.XML". The XML file, created on Jun. 28, 2023, is 39,992 bytes in size. The material in the XML file is hereby incorporated by reference in its entirety.

TECHNICAL FIELD

The present disclosure relates to novel proteins and pharmaceutical compositions comprising said proteins that have application, inter alia, in the treatment of gastrointestinal inflammatory diseases and epithelial barrier function disorders. In some embodiments, the proteins and pharmaceutical compositions described herein have particular application in the treatment or prevention of disease states associated with abnormally permeable epithelial barriers as well as inflammatory bowel diseases or disorders.

BACKGROUND

Inflammatory bowel disease (IBD) is a heterogeneous disease of unknown etiology resulting in frequent and bloody bowel movements accompanied with histopathological damage to the gastrointestinal mucosa (Zhang et al., 2017, Front Immunol, 8:942). While specific triggers of disease remain poorly defined, one proposal of disease progression suggests a breakdown of intestinal barrier function allows bacteria or bacterial components to translocate into mucosal tissue (Coskun, 2014, Front Med (Lausanne), 1:24; Martini et al., 2017, Cell Mol Gastroenterol Hepatol, 4:33-46). Bacterial translocation results in activation of inflammatory signaling which triggers additional barrier disruption, resulting in a cyclic amplification loop of barrier disruption, bacterial translocation and inflammation. While many current therapies target inflammation, the lack of therapies promoting mucosal healing provides an opportunity for novel therapies promoting epithelial repair and intestinal barrier integrity.

Expanding upon the hypothesis that bacterial translocation can trigger IBD, more recent studies have demonstrated detrimental changes in intestinal microbiota, or dysbiosis, may promote development of IBD.

Currently, many IBD therapeutics available in the market merely aim to target and suppress the discussed inflammatory response associated with IBD. While helpful, this narrow therapeutic mode of action disregards the important contribution that epithelial barrier integrity plays in the etiology of the disease.

Thus, there is a great need in the art for the development of a therapeutic, which not only suppresses the immune system's inflammatory response, but that also acts in concert to restore the epithelial barrier function in an individual. Also, there is a need for the production of a protein therapeutic such as that described herein which is stable through the manufacturing and/or processing of the protein therapeutic as well as under long term storage conditions.

SUMMARY OF THE DISCLOSURE

The present disclosure addresses the important need in the medical community for a therapeutic which can effectively treat a subject suffering from a gastrointestinal disorder such as an inflammatory bowel disease (IBD). In one aspect, novel protein therapeutics are provided which can facilitate or enhance the maintenance of epithelial barrier integrity and/or improve epithelial barrier repair. In some embodiments, the epithelial barrier is intestinal epithelial barrier. These protein therapeutics can also reduce inflammation of the intestine of the subject and/or decrease symptoms associated with inflammation of the intestine.

The protein therapeutics provided herein are useful in treating the numerous diseases and/or symptoms that may be associated with decreased gastrointestinal epithelial cell barrier function or integrity.

Provided herein is a therapeutic protein encoded by the genome of *Eubacterium eligens*, the protein designated herein as "SG-15." In some embodiments, the SG-15 protein comprises the amino acid sequence of SEQ ID NO:1, as well as fragments or variants thereof.

In some embodiments, the SG-15 protein comprises an amino acid sequence which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:1, SEQ ID NO:3, SEQ ID NO:5, or SEQ ID NO:7 wherein the amino acid sequence has at least 1, 2, 3 or 4 amino acid substitutions relative to SEQ ID NO:1, SEQ ID NO:3, SEQ ID NO:5, or SEQ ID NO:7, respectively. In other embodiments, the amino acid sequence has at least 2 and less than 3, 4, 5, 6, 7, 8, 9, or 10 amino acid substitutions. In still other embodiments, the SG-15 protein comprises an amino acid sequence which is not naturally occurring.

In some embodiments, the SG-15 protein comprises SEQ ID NO:1, SEQ ID NO:3, SEQ ID NO:5, or SEQ ID NO:7.

In some embodiments, the SG-15 protein is about 350 to 450 amino acids, 375 to 425 amino acids, 380 to 420 amino acids, 390 to 410 amino acids, or 395 to 405 amino acids in length. In other embodiments, the SG-15 protein is 390, 391, 392, 393, 394, 395, 396, 397, 398, 399, 400, 401, 402, 403, 404, 405, 406, 407, 408, 409, or 410 amino acids in length.

In some embodiments, a polynucleotide is provided which encodes the amino acid sequence of SG-15 (SEQ ID NO:1) or fragment or variant thereof. In other embodiments, the polynucleotide encodes a protein which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:1, SEQ ID NO:3, SEQ ID NO:5, or SEQ ID NO:7. In still other embodiments, the polynucleotide comprises a nucleotide sequence which is at least 75%, 80%, 85%, 90%, 91%, 92%, 93%, 94%, 95%, 96%, 97%, 98%, 99% or 100% identical to SEQ ID NO:2, SEQ ID NO:4, SEQ ID NO:6 or SEQ ID NO:8.

Provided herein is a therapeutic protein encoded by the genome of *Eubacterium eligens*, the protein designated herein as "SG-16." In some embodiments, the SG-16 protein comprises the amino acid sequence of SEQ ID NO:9, as well as fragments or variants thereof.

In some embodiments, the SG-16 protein comprises an amino acid sequence which is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:9 or SEQ ID NO:11, wherein the amino acid sequence has at least 1, 2, 3 or 4 amino acid substitutions relative to SEQ ID NO:9 or SEQ ID NO:11, respectively. In other embodiments, the amino acid sequence has at least 2 and less than 3, 4, 5, 6, 7, 8, 9, or 10 amino acid substitutions. In still other embodiments, the SG-16 protein comprises an amino acid sequence which is not naturally occurring.

In some embodiments, the SG-16 protein comprises SEQ ID NO:9 or SEQ ID NO:11.

In some embodiments, the SG-16 protein is about 95 to 150 amino acids, 100 to 135 amino acids, 105 to 130 amino acids, or 110 to 125 amino acids in length. In other embodiments, the SG-16 protein is 110, 111, 112, 113, 114, 115, 116, 117, 118, 119, 120, 121, 122, 123, 124, 125, 126, 127, 128, 129, or 130 amino acids in length.

In some embodiments, a polynucleotide is provided which encodes the amino acid sequence of SG-16 (SEQ ID NO:9) or fragment or variant thereof. In other embodiments, the polynucleotide encodes a protein which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:9 or SEQ ID NO:11. In still other embodiments, the polynucleotide comprises a nucleotide sequence which is at least 75%, 80%, 85%, 90%, 91%, 92%, 93%, 94%, 95%, 96%, 97%, 98%, 99% or 100% identical to SEQ ID NO:10 or SEQ ID NO: 12.

Provided herein is a therapeutic protein encoded by the genome of *Eubacterium eligens*, the protein designated herein as "SG-17." In some embodiments, the SG-17 protein comprises the amino acid sequence of SEQ ID NO: 13, as well as fragments or variants thereof.

In some embodiments, the SG-17 protein comprises an amino acid sequence which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:13, SEQ ID NO:15 or SEQ ID NO:17 wherein the amino acid sequence has at least 1, 2, 3 or 4 amino acid substitutions relative to SEQ ID NO:13, SEQ ID NO:15, or SEQ ID NO:17, respectively. In other embodiments, the amino acid sequence has at least 2 and less than 3, 4, 5, 6, 7, 8, 9, or 10 amino acid substitutions. In still other embodiments, the SG-17 protein comprises an amino acid sequence which is not naturally occurring.

In some embodiments, the SG-17 protein comprises SEQ ID NO:13, SEQ ID NO:15, or SEQ ID NO:17.

In some embodiments, the SG-17 protein is about 300 to 475 amino acids, 310 to 450 amino acids, 315 to 335 amino acids, or 320 to 330 amino acids in length. In other embodiments, the SG-17 protein is 315, 316, 317, 318, 319, 320, 321, 322, 323, 324, 325, 326, 327, 328, 329, 330, 331, 332, 333, 334, or 335 amino acids in length.

In some embodiments, a polynucleotide is provided which encodes the amino acid sequence of SG-17 (SEQ ID NO:13) or fragment or variant thereof. In other embodiments, the polynucleotide encodes a protein which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:13, SEQ ID NO:15, or SEQ ID NO:17. In still other embodiments, the polynucleotide comprises a nucleotide sequence which is at least 75%, 80%, 85%, 90%, 91%, 92%, 93%, 94%, 95%, 96%, 97%, 98%, 99% or 100% identical to SEQ ID NO:14, SEQ ID NO:16 or SEQ ID NO: 18.

Provided herein is a therapeutic protein encoded by the genome of *Clostridium bartlettii* sp. nov., the protein designated herein as "SG-18." In some embodiments, the SG-18 protein comprises the amino acid sequence of SEQ ID NO:19, as well as fragments or variants thereof.

In some embodiments, the SG-18 protein comprises an amino acid sequence which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:19, SEQ ID NO:21, SEQ ID NO:23 or SEQ ID NO:25 wherein the amino acid sequence has at least 1, 2, 3 or 4 amino acid substitutions relative to SEQ ID NO:19, SEQ ID NO:21, SEQ ID NO:23 or SEQ ID NO:25, respectively. In other embodiments, the amino acid sequence has at least 2 and less than 3, 4, 5, 6, 7, 8, 9, or 10 amino acid substitutions. In still other embodiments, the t SG-18 protein comprises an amino acid sequence which is not naturally occurring.

In some embodiments, the SG-18 protein comprises to SEQ ID NO:19, SEQ ID NO:21, SEQ ID NO:23 or SEQ ID NO:25.

In some embodiments, the SG-18 protein is about 240 to 290 amino acids, 250 to 275 amino acids, 255 to 280 amino acids, or 260 to 275 amino acids in length. In other embodiments, the SG-18 protein is 255, 256, 257, 258, 259, 260, 261, 262, 263, 264, 265, 266, 267, 268, 269, 270, 271, 272, 273, 274, or 275 amino acids in length.

In some embodiments, a polynucleotide is provided which encodes the amino acid sequence of SG-18 (SEQ ID NO:19) or fragment or variant thereof. In other embodiments, the polynucleotide encodes a protein which is at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to SEQ ID NO:19, SEQ ID NO:21, SEQ ID NO: 23 or SEQ ID NO:25. In still other embodiments, the polynucleotide comprises a nucleotide sequence which is at least 75%, 80%, 85%, 90%, 91%, 92%, 93%, 94%, 95%, 96%, 97%, 98%, 99% or 100% identical to SEQ ID NO:20, SEQ ID NO:22, SEQ ID NO:24 or SEQ ID NO:26.

ADDITIONAL EMBODIMENTS

In some embodiments, the SG protein is chemically modified at the N-terminus and/or the C-terminus. In other embodiments, the N-terminus of the SG protein is chemically modified by acetylation. In still other embodiments, the C-terminus is chemically modified by amidation.

In some embodiments, the SG protein is pegylated.

In some embodiments, the SG protein is substantially purified and which is modified by glycosylation, ubiquitination, nitrosylation, methylation, acetylation, or lipidation.

In some embodiments, the SG protein is fused to second protein. In other embodiments, the second protein is an immunoglobulin Fe domain or a human serum albumin protein domain.

In some embodiments, the disclosure teaches an antibody or fragment thereof which specifically binds the SG protein.

In some embodiments, the SG protein increases the barrier function of an epithelial cell layer in an in vitro assay, wherein the increase is relative to the barrier function in the assay in the absence of the protein. In other embodiments, the in vitro assay is a transepithelial electrical resistance (TEER) assay. In still other embodiments, the increase in barrier function is an increase in electrical resistance of at least 5%, 10%, 20%, 30%, 40%, 50%, 60%, 70%, 80%, or 90% greater than the electrical resistance in the assay in the absence of the SG protein. In some embodiments, the epithelial cell layer is an intestinal epithelial cell layer. In still other embodiments, the intestinal epithelial cell layer is a cell layer which comprises enterocytes and goblet cells.

In some embodiments, the SG protein decreases the secretion of a pro-inflammatory cytokine from a cell in an in vitro assay. In other embodiments, the in vitro assay comprises incubation of monocytic cells with heat killed E. coli in the presence and absence of the SG protein. In still other embodiments, the at least one pro-inflammatory cytokine is selected from the group consisting of TNF-α, IL-17, IL-1β, IL-2, IFN-γ, IL-6, IL-12, IL-25, IL-33, IL-8, MCP-1, MIP-3α, CXCL1, and IL-23.

In some embodiments, the SG protein increases secretion of an anti-inflammatory cytokine from a cell in an in vitro assay. In other embodiments, the in vitro assay comprises incubation of a monocyte with heat killed E. coli in the presence and absence of the SG protein. In still embodiments, the at least one anti-inflammatory cytokine is selected from the group consisting of IL-4, IL-10, IL-13, IFN-α, and TGF-β.

In some embodiments, the SG protein reduces intestinal tissue pathology in a subject administered the SG protein. In some embodiments, the subject was induced to have intestinal tissue damage by treatment with a chemical. In other embodiments, the subject was treated with the chemical dextran sodium sulfate (DSS) to induce intestinal tissue damage. In still other embodiments, the subject is a mammal. In yet other embodiments, the animal is a rodent. In other embodiments, the subject is a non human primate.

In some embodiments, the SG protein reduces gastrointestinal inflammation in a subject administered the SG protein. In other embodiments, the SG protein reduces intestinal mucosa inflammation in the subject. In still other embodiments, the SG protein improves intestinal epithelial cell barrier function or integrity in the subject.

In some embodiments, the SG protein increases the amount of mucin in intestinal tissue in a subject administered the SG protein.

In some embodiments, the SG protein increases intestinal epithelial cell wound healing in a subject administered the SG protein. In other embodiments, the SG protein increases intestinal epithelial cell wound healing in an in vitro assay.

In some embodiments, the SG protein prevents or reduces colon shortening in a subject administered the SG protein.

In some embodiments, the SG protein modulates (i.e. increases or decreases) a cytokine in the blood, plasma, serum, tissue and/or mucosa of a subject administered the SG protein.

In some embodiments, the SG protein decreases the levels of at least one pro-inflammatory cytokine in the blood, plasma, serum, tissue and/or mucosa of the subject. In other embodiments, the at least one pro-inflammatory cytokine is selected from the group consisting of TNF-α, IL-17, IL-1β, IL-2, IFN-γ, IL-6, IL-12, IL-25, IL-33, IL-8, MCP-1, MIP-3α, CXCL1, and IL-23.

In some embodiments, the SG protein increases the levels of at least one anti-inflammatory cytokine in the blood, plasma, serum, tissue and/or mucosa of the subject. In other embodiments, the at least one anti-inflammatory cytokine is selected from the group consisting of IL-4, IL-10, IL-13, IFN-α, and TGF-β.

In some embodiments, the SG protein decreases the level of at least one anti-inflammatory cytokine in the blood, plasma, serum, tissue and/or mucosa of the subject. In other embodiments, the at least one anti-inflammatory cytokine is selected from the group consisting of IL-4, IL-10, IL-13, IFN-α, and TGF-β.

In some embodiments, the disclosure teaches a polynucleotide encoding an SG protein and methods of expressing the polypeptide in a host cell. In a particular embodiment, the polynucleotide comprises a sequence which encodes an SG protein that is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, or 100% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25. In further embodiments, the polynucleotide comprises a sequence which encodes an SG protein that is less than 100% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25, respectively. In still other embodiments, the polynucleotide is codon-optimized for expression in a recombinant host cell. In yet other embodiments, the polynucleotide is codon-optimized for expression in E. coli.

In some embodiments, the disclosure teaches a nucleic acid which comprises a sequence that is at least 70%, 75%, 80%, 85%, 90%, 91%, 92%, 93%, 94%, 95%, 96%, 97%, 98%, 99%, or 100% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:26. In further embodiments, the nucleic acid comprises a sequence which is less than 100% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:26, respectively.

In some aspects, an expression vector is provided, comprising an exogenous polynucleotide that encodes an SG protein comprising an amino acid sequence having at least 70%, 75%, 80%, 85%, 90%, 91%, 92%, 93%, 94%, 95%, 96%, 97%, 98%, 99%, or 100% identity to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25. In further embodiments, the polynucleotide encodes a protein which is less than 100% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25, respectively.

In some aspects, an expression system is provided, comprising a host cell and the expression vector comprising the aforementioned exogenous polynucleotide.

In some embodiments, the host cell is prokaryotic or eukaryotic. In other embodiments, the host cell is mammalian cell, a yeast cell or a bacterial cell. In still other embodiments, the bacterial cell is Escherichia coli. In yet other embodiments, the mammalian cell is a CHO cell.

In some aspects, a method of producing the SG protein is provided.

In some embodiments, the method for producing the SG protein comprises transforming or transfecting the aforementioned host cell with the aforementioned expression vector, culturing the transformed or transfected host cell under conditions sufficient for the expression of the SG protein encoded by the aforementioned exogenous polynucleotide. In other embodiments, the method further comprises purifying the protein from the transformed or transfected host cell and culture media.

In some aspects, the disclosure provides a pharmaceutical composition for treating an inflammatory bowel disease, comprising: an SG protein comprising an amino acid sequence having at least 70%, 75%, 80%, 85%, 90%, 91%, 92%, 93% 94%, 95%, 96%, 97%, 98%, 99%, 99.1%, 99.2%, 99.3%, 99.4%, 99.5%, 99.6%, 99.7%, 99.8%, 99.9% or 100% sequence identity to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25 and a pharmaceutically acceptable carrier. In some embodiments, the SG protein is purified or substantially purified. In some embodiments, the SG protein comprises the amino acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO: 25 or a variant thereof wherein the variant is at least 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical to but less than 100% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25, respectively.

In some embodiments, the pharmaceutical composition is formulated for rectal, parenteral, intravenous, topical, oral, dermal, transdermal, or subcutaneous administration. In other embodiments, the pharmaceutical composition is a liquid, a gel, or a cream. In still other embodiments, the pharmaceutical composition is a solid composition comprising an enteric coating.

In some embodiments, the pharmaceutical composition is a cream, a capsule, a liquid, a gel, or an emulsion.

In some embodiments, the pharmaceutical composition is formulated to provide delayed release of the SG protein. In other embodiments, the delayed release is release of the SG protein into the gastrointestinal tract. In yet other embodiments, the delayed release of the SG protein is into the mouth, the small intestine, the large intestine and/or the rectum.

In some embodiments, the pharmaceutical composition is formulated to provide sustained release of the SG protein. In other embodiments, the sustained release of the SG protein is release into the gastrointestinal tract. In yet other embodiments, the sustained release of the SG protein is into the mouth, the small intestine, the large intestine and/or the rectum. In still other embodiments, the sustained release composition releases the SG protein over a time period of about 1 to 20 hours, 1 to 10 hours, 1 to 8 hours, 4 to 12 hours or 5 to 15 hours.

In some embodiments, the pharmaceutical composition further comprises a second therapeutic agent. In other embodiments, the second therapeutic agent is selected from the group consisting of an anti-diarrheal, a 5-aminosalicylic acid compound, an anti-inflammatory agent, an antibiotic, an anti-cytokine agent, an anti-inflammatory cytokine agent, a steroid, a corticosteroid, an immunosuppressant, a JAK inhibitor, an anti-integrin biologic, an anti-IL12/23R biologic, and a vitamin.

In some embodiments, the pharmaceutical composition further comprises a protease inhibitor. In still other embodiments, the protease inhibitor inhibits degradation of the SG protein in the presence of fecal matter and/or in the presence of blood.

As aforementioned, these novel protein therapeutics are able to promote epithelial barrier function and integrity in a subject. In some embodiments, the epithelial barrier function is intestinal epithelial barrier function. Additionally, the therapeutic effect of the SG protein includes suppression of an inflammatory immune response in an IBD individual. Thus, the disclosure provides detailed guidance for methods of utilizing the taught therapeutic proteins to treat a host of gastrointestinal inflammatory conditions, and disease states involving compromised gastrointestinal epithelial barrier integrity. Accordingly, in some aspects, methods of treating a disease—such as an intestinal epithelium barrier function associated disease—are provided, which utilize any sequence disclosed in the current application and sequence listing.

In some embodiments, a method for treating an inflammatory bowel disease or disorder in a patient in thereof is provided, comprising: administering to the patient a pharmaceutical composition, comprising: i) an SG protein as described herein; and ii) a pharmaceutically acceptable carrier.

In some embodiments, the patient has been diagnosed with intestinal inflammation. In other embodiments, the intestinal inflammation is in the small intestine and/or the large intestine. In still other embodiments, the intestinal inflammation is in the rectum. In still other embodiments, the patient has been diagnosed with pouchitis.

In some embodiments, the patient has been diagnosed with intestinal ulcers. In other embodiments, the patient has been diagnosed with draining enterocutaneous and/or rectovaginal fistulas.

In some embodiments, the patient has been diagnosed with Crohn's disease (CD). In other embodiments, the CD is mildly active CD. In still other embodiments, the CD is moderately to severely active CD. In yet other embodiments, the patient has been diagnosed with pediatric CD.

In some embodiments, the patient has been diagnosed with short bowel syndrome or irritable bowel syndrome.

In some embodiments, the patient has been diagnosed with mucositis. In other embodiments, the mucositis is oral mucositis. In still other embodiments, the mucositis is chemotherapy-induced mucositis, radiation therapy-induced mucositis, chemotherapy-induced oral mucositis, or radiation therapy-induced oral mucositis. In yet other embodiments, the mucositis is gastrointestinal mucositis. In still other embodiments, the gastrointestinal mucositis is mucositis of the small intestine, the large intestine, or the rectum.

In some embodiments, the administering to a patient diagnosed with CD resulted in a reduced number of draining enterocutaneous and/or rectovaginal fistulas. In other embodiments, the administering maintains fistula closure in adult patients with fistulizing disease.

In other embodiments, the patient has been diagnosed with ulcerative colitis (UC). In other embodiments, the UC is mildly active UC. In still other embodiments, the UC is moderately to severely active UC. In still other embodiments, the patient has been diagnosed with pediatric UC.

In some embodiments, the patient is in clinical remission from an IBD. In other embodiments, the patient is in clinical remission from UC, pediatric UC, CD or pediatric CD.

In some embodiments, the patient has an inflammatory bowel disease or disorder other than Crohn's disease or ulcerative colitis. In other embodiments, the patient has at least one symptom associated with inflammatory bowel disease.

In some embodiments, the administering reduces gastrointestinal inflammation and/or reduces intestinal mucosa inflammation associated with inflammatory bowel disease in the patient. In other embodiments, the administering improves intestinal epithelial cell barrier function or integrity in the patient.

In some embodiments, after the administering the patient experiences a reduction in at least one symptom associated with an inflammatory bowel disease or disorder. In other embodiments, the at least one symptom is selected from the group consisting of abdominal pain, blood in stool, pus in stool, fever, weight loss, frequent diarrhea, fatigue, reduced appetite, nausea, cramps, anemia, tenesmus, and rectal bleeding. In still other embodiments, after the administering the patient experiences reduced frequency of diarrhea, reduced blood in stool and/or reduced rectal bleeding.

In some embodiments, the patient has experienced inadequate response to conventional therapy. In other embodiments, the conventional therapy is treatment with an aminosalicylate, a corticosteroid, a thiopurine, methotrexate, a JAK inhibitor, a sphingosine 1-phosphate (SIP) receptor inhibitor, an anti-integrin biologic, an anti-IL12/23R or anti-IL23/p10 biologic, and/or an anti-tumor necrosis factor agent or biologic.

In some embodiments, the administering modulates (i.e. increases or decreases) levels of a cytokine in the blood, plasma, serum, mucosa or tissue of the patient.

In some embodiments, the administering suppresses the levels of at least one pro-inflammatory cytokine in the blood, plasma, serum, mucosa or tissue of the patient. In other embodiments, the at least one pro-inflammatory cytokine is selected from the group consisting of TNF-α, IL-17, IL-1β, IL-2, IFN-γ, IL-6, IL-12, IL-25, IL-33, IL-8, MCP-1, MIP-3α, CXCL1, and IL-23.

In some embodiments, the administering increases the levels of at least one anti-inflammatory cytokine in the blood, plasma, serum, mucosa or tissue of the patient. In other embodiments, the at least one anti-inflammatory cytokine is selected from the group consisting of IL-4, IL-10, IL-13, IFN-α, and TGF-β.

In some embodiments, the administering decreases the level of at least one anti-inflammatory cytokine in the blood, plasma, serum, mucosa or tissue of the patient. In other embodiments, the at least one anti-inflammatory cytokine is selected from the group consisting of IL-4, IL-10, IL-13, IFN-α, and TGF-β.

In some embodiments, the administering increases the amount of mucin in intestinal lumen of the patient.

In some embodiments, the administering increases intestinal epithelial cell wound healing in the patient.

In some embodiments, the administering prevents or reduces colon shortening in the patient.

In some embodiments, the administering comprises rectal, intravenous, parenteral, oral, topical, dermal, transdermal or subcutaneous administering of the pharmaceutical composition to the patient. In other embodiments, the administering is to the gastrointestinal lumen.

In some embodiments, the patient is also administered at least one second therapeutic agent. In other embodiments, the at least one second therapeutic agent is selected from the group consisting of an anti-diarrheal, an anti-inflammatory agent, an antibody, an antibiotic, or an immunosuppressant. In still other embodiments, the at least one second therapeutic agent is an aminosalicylate, a steroid, or a corticosteroid. In other embodiments, the at least one second therapeutic agent is selected from the group consisting of adalimumab, pegol, golimumab, infliximab, vedolizumab, ustekinumab, tofacitinib, and certolizumab or certolizumab pegol.

DETAILED DESCRIPTION

Figure 1A:
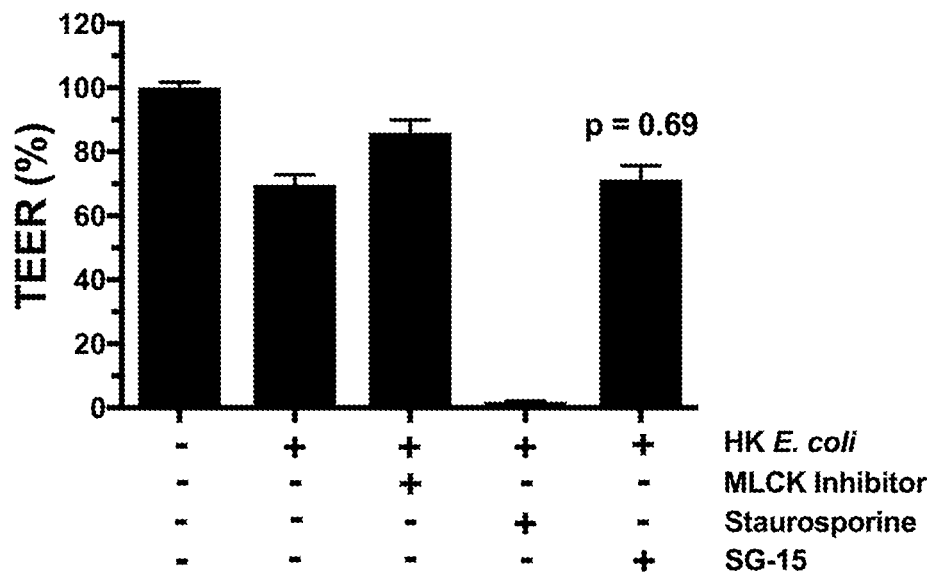
FIG. 1A and FIG. 1B show restoration, by SG-15, of epithelial barrier integrity following inflammation induced disruption, as described in Example 1B.

The present disclosure provides novel protein therapeutics that are useful in the treatment of subjects suffering from symptoms associated with gastrointestinal disorders. For example, an SG protein described herein can promote or enhance epithelial barrier function and/or integrity. The SG protein may also suppress the inflammatory immune response in an IBD individual. The protein therapeutic provided herein is useful in treating the numerous diseases that are associated with decreased gastrointestinal epithelial cell barrier function or integrity and inflammation of the intestine.

In the present disclosure, provided are also SG protein variants that have therapeutic activity comparable to or superior to the original protein, but the SG protein variants have enhanced stability through the manufacturing and processing of the protein therapeutic products as well as under long-term storage conditions.

Definitions

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art. Thus, while the following terms are believed to be well understood by one of ordinary skill in the art, the following definitions are set forth to facilitate explanation of the presently disclosed subject matter.

Throughout this specification, the word "comprise" or variations such as "comprises" or "comprising" will be understood to imply the inclusion of a stated component, or group of components, but not the exclusion of any other components, or group of components.

The term "a" or "an" refers to one or more of that entity, i.e. can refer to a plural referents. As such, the terms "a" or "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

The term "including" is used to mean "including but not limited to." "Including" and "including but not limited to" are used interchangeably.

The terms "SG protein" and "SG" as used herein and when immediately followed by a numerical designation refer to various proteins, wherein the complete designation (i.e., SG/number) refers to specific protein sequences as described herein. The terms "SG/number protein" and "SG/number" wherein the term "number" is provided as an actual numerical designation as used herein encompass SG protein sequence variants and/or fragments (which are further defined herein).

The terms "gastrointestinal" or "gastrointestinal tract," "alimentary canal," and "intestine," as used herein, may be used interchangeably to refer to the series of hollow organs extending from the mouth to the anus and including the mouth, esophagus, stomach, small intestine, large intestine, rectum and anus. The terms "gastrointestinal" or "gastrointestinal tract," "alimentary canal," and "intestine" are not always intended to be limited to a particular portion of the alimentary canal.

The term "SG-15" as used herein refers to a protein comprising the amino acid sequence of SEQ ID NO:1 and also to variants thereof having the same or similar functional activity as described herein. Accordingly, SG-15 can refer herein to proteins comprising or consisting of SEQ ID NO:1, SEQ ID NO:3, SEQ ID NO:5 or SEQ ID NO:7, or variants or fragments thereof. In U.S. provisional patent application (62/514,165, filed Jun. 2, 2017, to which the present specification claims priority and which is incorporated herein by reference in its entirety) the term "Experimental Protein 4" and variants thereof was used and is synonymous with SG-15 as used herein or variants thereof.

The term "SG-16" as used herein refers to a protein comprising the amino acid sequence of SEQ ID NO:9 and also to variants thereof having the same or similar functional activity as described herein. Accordingly, SG-16 can refer herein to proteins comprising or consisting of SEQ ID NO:9 or SEQ ID NO:11, or variants or fragments thereof. In U.S. provisional patent application (62/514,148, filed Jun. 2, 2017, to which the present specification claims priority and which is incorporated herein by reference in its entirety) the term "Experimental Protein 6" and variants thereof was used and is synonymous with SG-16 as used herein or variants thereof.

The term "SG-17" as used herein refers to a protein comprising the amino acid sequence of SEQ ID NO:13 and also to variants thereof having the same or similar functional activity as described herein. Accordingly, SG-17 can refer herein to proteins comprising or consisting of SEQ ID NO:13, SEQ ID NO:15 or SEQ ID NO:17, or variants or fragments thereof. In U.S. provisional patent application (62/518,137, filed Jun. 12, 2017, to which the present specification claims priority and which is incorporated herein by reference in its entirety) the term "Experimental Protein 7" and variants thereof was used and is synonymous with SG-17 as used herein or variants thereof.

The term "SG-18" as used herein refers to a protein comprising the amino acid sequence of SEQ ID NO:19 and also to variants thereof having the same or similar functional activity as described herein. Accordingly, SG-18 can refer herein to proteins comprising or consisting of SEQ ID NO:19, SEQ ID NO:21, SEQ ID NO:23 or SEQ ID NO:25, or variants or fragments thereof. In U.S. provisional patent application (62/518,138, filed Jun. 12, 2017, to which the present specification claims priority and which is incorporated herein by reference in its entirety) the term "Experimental Protein 5" and variants thereof was used and is synonymous with SG-18 as used herein or variants thereof.

A "signal sequence" (also termed "presequence," "signal peptide," "leader sequence," or "leader peptide") refers to a sequence of amino acids located at the N-terminus of a nascent protein, and which can facilitate the secretion of the protein from the cell. The resultant mature form of the extracellular protein lacks the signal sequence, which is cleaved off during the secretion process.

The recitations "sequence identity," "percent identity," "percent homology," or for example, comprising a "sequence 50% identical to," as used herein, refer to the extent that sequences are identical on a nucleotide-by-nucleotide or amino acid-by-amino acid basis, over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The phrases "substantially similar" and "substantially identical" in the context of at least two nucleic acids or polypeptides typically means that a polynucleotide or polypeptide comprises a sequence that has at least about 70%, 75%, 80%, 85%, 86%, 87%, 88%, 89%, 90%, 91%, 92%, 93%, 94%, 95%, 96%, 97%, 98%, 99%, 99.5%, 99.6%, 99.7% or even 99.8% sequence identity, in comparison with a reference polynucleotide or polypeptide. In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

Related (and derivative) proteins encompass "variant" proteins. Variant proteins can differ from another (i.e., parental) protein and/or from one another by a small number of amino acid residues. A variant may include one or more amino acid mutations (e.g., amino acid deletion, insertion or substitution) as compared to the parental protein from which it is derived.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more "conservative substitutions." An example of a conservative substitution is the exchange of an amino acid in one of the following groups for another amino acid of the same group (see U.S. Pat. No. 5,767,063; Kyte and Doolittle (1982) *J. Mol. Biol.* 157:105-132). (1) Hydrophobic: Norleucine, Ile, Val, Leu, Phe, Cys, Met; (2) Neutral hydrophilic: Cys, Ser, Thr; (3) Acidic: Asp, Glu; (4) Basic: Asn, Gln, His, Lys, Arg; (5) Residues that influence chain orientation: Gly, Pro; (6) Aromatic: Trp, Tyr, Phe; and (7) Small amino acids: Gly, Ala, Ser. Thus, the term "conservative substitution" with respect to an amino acid denotes that one or more amino acids are replaced by another, chemically similar residue, wherein said substitution does not generally affect the functional properties of the protein. Examples include substitution of amino acid residues with similar characteristics, e.g., small amino acids, acidic amino acids, polar amino acids, basic amino acids, hydrophobic amino acids and aromatic amino acids. In some embodiments, the disclosure provides for proteins that have at least one non-naturally occurring, conservative amino acid substitution relative to the amino acid sequence identified in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23 or SEQ ID NO:25. Some common exemplary examples of conservative amino acid substitutions are found below.

The term "amino acid" or "any amino acid" refers to any and all amino acids, including naturally occurring amino acids (e.g., α-amino acids), unnatural amino acids, modified amino acids, and unnatural or non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur, e.g., in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 unnatural amino acids are known and thousands of more combinations are possible. "Modified" amino acids include amino acids (e.g., natural amino acids) that have been chemically modified to include a group, groups, or chemical moiety not naturally present on the amino acid.

As used herein, a "synthetic nucleotide sequence" or "synthetic polynucleotide sequence" is a nucleotide sequence that is not known to occur in nature, or that is not naturally occurring. Generally, such a synthetic nucleotide sequence will comprise at least one nucleotide difference when compared to any other naturally occurring nucleotide sequence. As used herein, a "synthetic amino acid sequence" or "synthetic peptide sequence" or "synthetic polypeptide sequence" or "synthetic protein sequence" is an amino acid sequence that is not known to occur in nature, or that is not naturally occurring. Generally, such a synthetic amino acid sequence will comprise at least one amino acid difference when compared to any other naturally occurring amino acid sequence.

As used herein, a "synthetic protein" or "synthetic therapeutic protein" means a protein that comprises an amino acid sequence that contains one or more amino acids substituted with different amino acids relative to a naturally occurring amino acid sequence. That is, a "synthetic protein" comprises an amino acid sequence that has been altered to contain at least one non-naturally occurring substitution modification at a given amino acid position(s) relative to a naturally occurring amino acid sequence.

The term "about" as used herein with respect to % sequence identity, or % sequence homology, of a nucleic acid sequence, or amino acid sequence, means up to and including ±1.0% in 0.1% increments. For example, "about 90%" sequence identity includes 89.0%, 89.1%, 89.2%, 89.3%, 89.4%, 89.5%, 89.6%, 89.7%, 89.8%, 89.9%, 90%, 90.1%, 90.2%, 90.3%, 90.4%, 90.5%, 90.6%, 90.7%, 90.8%, 90.9%, and 91 %. If not used in the context of % sequence identity, then "about" means±1%, 2%, 3%, 4%, 5%, 6%, 7%, 8%, 9%, or 10%, depending upon context of the value in question.

For the most part, the names of natural and non-natural aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and aminoacyl residues employed in this specification and appended claims differ from those suggestions, they will be made clear to the reader.

Throughout the present specification, unless natural amino acids are referred to by their full name (e.g., alanine, arginine, etc.), they are designated by their conventional three-letter or single-letter abbreviations (e.g., Ala or A for alanine, Arg or R for arginine, etc.). Unless otherwise indicated, three-letter and single-letter abbreviations of amino acids refer to the L-isomeric form of the amino acid. The term "L-amino acid," as used herein, refers to the "L" isomeric form of a peptide, and conversely the term "D-amino acid" refers to the "D" isomeric form of a peptide (e.g., Dasp, (D)Asp or D-Asp; Dphe, (D)Phe or D-Phe). Amino acid residues in the D isomeric form can be substituted for any L-amino acid residue, as long as the desired function is retained by the peptide. D-amino acids may be indicated as customary in lower case when referred to using single-letter abbreviations.

In the case of less common or non-natural amino acids, unless they are referred to by their full name (e.g., sarcosine, ornithine, etc.), three- or four-character codes are frequently employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (γ-glutamic acid), Gaba (γ-aminobutanoic acid), β-Pro (pyrrolidine-3-carboxylic acid), and 8Ado (8-amino-3,6-dioxaoctanoic acid), Abu (2-amino butyric acid), βhPro (β-homoproline), βhPhe (β-homophenylalanine) and Bip (β,β diphenylalanine), and Ida (Iminodiacetic acid).

Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—NH$_2$" moiety at the C-terminus of the sequence indicates a hydroxy group or an amino group, corresponding to the presence of an amido (CONH$_2$) group at the C-terminus, respectively. In each sequence of the disclosure, a C-terminal "—OH" moiety may be substituted for a C-terminal "—NH$_2$" moiety, and vice-versa.

The term "Ac," as used herein, refers to acetyl protection through acylation of the C- or N-terminus of a polypeptide. In certain peptides shown herein, the NH$_2$ locates at the C-terminus of the peptide indicates an amino group. The term "carboxy," as used herein, refers to —CO$_2$H.

The term "pharmaceutically acceptable salt," as used herein, represents salts or zwitterionic forms of the peptides, proteins, or compounds of the present disclosure, which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see *Handbook of Pharmaceutical Salts: Properties, Selection, and Use* by Stahl and Wermuth (Wiley-VCH, 2002).

As used herein, the term "at least a portion" or "fragment" of a nucleic acid or polypeptide means a portion having the minimal size characteristics of such sequences, or any larger fragment of the full length molecule, up to and including the full length molecule.

The term "primer" as used herein refers to an oligonucleotide which is capable of annealing to a target polynucleotide.

As used herein, the phrases "recombinant construct," "expression construct," "chimeric construct," "construct," and "recombinant DNA construct" are used interchangeably herein and are well-known to the ordinarily skilled artisan.

As used herein, the term "host cell" refers to a cell or cell line into which a recombinant expression vector for production of a polypeptide may be introduced for expression of the polypeptide.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system.

The terms "patient," "subject," and "individual" may be used interchangeably and refer to either a human or a non-human animal. These terms include mammals such as humans, non-human primates, livestock animals (e.g., bovines, porcines), companion animals (e.g., canines, felines) and rodents (e.g., mice and rats). In certain embodiments, the terms refer to a human patient. In exemplary embodiments, the terms refer to a human patient that suffers from a gastrointestinal inflammatory condition.

As used herein, "improved" should be taken broadly to encompass improvement in an identified characteristic of a disease state, said characteristic being regarded by one of skill in the art to generally correlate, or be indicative of, the disease in question, as compared to a control, or as compared to a known average quantity associated with the characteristic in question. For example, "improved" epithelial barrier function associated with application of a protein of the disclosure can be demonstrated by comparing the epithelial barrier integrity of a human treated with a protein of the disclosure, as compared to the epithelial barrier integrity of a human not treated. Alternatively, one could compare the epithelial barrier integrity of a human treated with a protein of the disclosure to the average epithelial barrier integrity of a human, as represented in scientific or medical publications known to those of skill in the art. In the present disclosure, "improved" does not necessarily demand that the data be statistically significant (i.e. p<0.05); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments. Thus, an "inhibited immune response" or the "inhibition of inflammatory cytokines" does not require absolute inhibition.

Thus, as used herein, the terms "increase," "suppress" or "reduce," or grammatical equivalents thereof, indicate values that are relative to a reference (e.g., baseline) measurement, such as a measurement taken under comparable conditions (e.g., in the same individual prior to initiation of treatment described herein, or a measurement in a control individual (or multiple control individuals) in the absence of treatment) described herein. In some embodiments, a suitable control is a baseline measurement, such as a measurement in the same individual prior to initiation of the treatment described herein, or a measurement in a control individual (or multiple control individuals) in the absence of the treatment described herein.

As used herein, the term "IBD" or "inflammatory bowel disease" refers to conditions in which individuals have chronic or recurring immune response and inflammation of the gastrointestinal (GI) tract. The two most common inflammatory bowel diseases are ulcerative colitis (UC) and Crohn's disease (CD).

As used herein, the term "therapeutically effective amount" refers to an amount of a therapeutic agent (e.g., a peptide, polypeptide, or protein of the disclosure), which confers a therapeutic effect on the treated subject, at a reasonable benefit/risk ratio applicable to any medical treatment. Such a therapeutic effect may be objective (i.e., measurable by some test or marker) or subjective (i.e., subject gives an indication of, or feels an effect). In some embodiments, "therapeutically effective amount" refers to an amount of a therapeutic agent or composition effective to treat, ameliorate, or prevent (e.g., delay onset of) a relevant disease or condition, and/or to exhibit a detectable therapeutic or preventative effect, such as by ameliorating symptoms associated with the disease, preventing or delaying onset of the disease, and/or also lessening severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, or on combination with other therapeutic agents. Alternatively or additionally, a specific therapeutically effective amount (and/or unit dose) for any particular patient may depend upon a variety of factors including the particular form of disease being treated; the severity of the condition or pre-condition; the activity of the specific therapeutic agent employed; the specific composition employed; the age, body weight, general health, sex and diet of the patient; the time of administration, route of administration, and/or rate of excretion or metabolism of the specific therapeutic agent employed; the duration of the treatment; and like factors as is well known in the medical arts. The current disclosure utilizes therapeutically effective amounts of novel proteins, and compositions comprising same, to treat a variety of diseases, such as: gastrointestinal inflammatory diseases or diseases involving gastrointestinal epithelial barrier malfunction. The therapeutically effective amounts of the administered protein, or compositions comprising same, will in some embodiments reduce inflammation associated with IBD or repair gastrointestinal epithelial barrier integrity and/or function.

As used herein, the term "treatment" (also "treat" or "treating") refers to any administration of a therapeutic agent (e.g., a peptide, polypeptide, or protein of the disclosure), according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., chronic or recurring immune response and inflammation of the gastrointestinal (GI) tract); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

"Pharmaceutical" implies that a composition, reagent, method, and the like, are capable of a pharmaceutical effect, and also that the composition is capable of being administered to a subject safely. "Pharmaceutical effect," without limitation, can imply that the composition, reagent, or method, is capable of stimulating a desired biochemical, genetic, cellular, physiological, or clinical effect, in at least one individual, such as a mammalian subject, for example, a human, in at least 5% of a population of subjects, in at least 10%, in at least 20%, in at least 30%, in at least 50% of subjects, and the like. "Pharmaceutically acceptable" means approved by a regulatory agency of the Federal or a state government or listed in the U.S. Pharmacopoeia or other generally recognized pharmacopoeia for safe use in animals, and more particularly safe use in humans. "Pharmaceutically acceptable vehicle" or "pharmaceutically acceptable excipient" refers to a diluent, adjuvant, excipient or carrier with which a protein as described herein is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease, or causing the symptom to develop with less severity than in absence of the treatment). "Prevention" or "prophylaxis" may refer to delaying the onset of the disease or disorder.

The therapeutic pharmaceutical compositions taught herein may comprise one or more natural products. However, in certain embodiments, the therapeutic pharmaceutical compositions themselves do not occur in nature. Further, in certain embodiments, the therapeutic pharmaceutical compositions possess markedly different characteristics, as compared to any individual naturally occurring counterpart, or composition component, which may exist in nature. That is, in certain embodiments, the pharmaceutical compositions taught herein—which comprise a therapeutically effective amount of a purified protein—possess at least one structural and/or functional property that impart markedly different characteristics to the composition as a whole, as compared to any single individual component of the composition as it may exist naturally. The courts have determined that compositions comprising natural products, which possess markedly different characteristics as compared to any individual component as it may exist naturally, are statutory subject matter. Thus, the taught therapeutic pharmaceutical compositions as a whole possess markedly different characteristics. These characteristics are illustrated in the data and examples taught herein.

Details of the disclosure are set forth herein. Although methods and materials similar or equivalent to those described herein can be used in the practice or testing of the present disclosure, illustrative methods and materials are now described. Other features, objects, and advantages of the disclosure will be apparent from the description and from the claims.

Therapeutic Proteins Derived from the Microbiome—Overview of the Disclosure

Numerous diseases and disorders are associated with decreased gastrointestinal epithelial cell barrier function or integrity. These diseases and disorders are multifaceted and present diagnostically in a myriad of ways. One such disease is inflammatory bowel disease (IBD), the incidence and prevalence of which is increasing with time and in different regions around the world, indicating its emergence as a global disease. (Molodecky et al., Gastroenterol 142:46-54, 2012). IBD is a collective term that describes conditions with chronic or recurring immune response and inflammation of the gastrointestinal (GI) tract. The two most common inflammatory bowel diseases are ulcerative colitis (UC) and Crohn's disease (CD). Both are marked by an abnormal response of the GI immune system. Normally, immune cells protect the body from infection. In people with IBD, however, this immune system mistakes food, bacteria, and other materials in the intestine for pathogens and an inflammatory response is launched into the lining of the intestines, creating chronic inflammation. When this happens, the patient experiences the symptoms of IBD.

IBD involves chronic inflammation of all, or part, of the digestive tract. Both UC and CD usually involve, for example, severe diarrhea, abdominal pain, fatigue, and weight loss. IBD and associated disorders can be debilitating and sometimes lead to life-threatening complications.

With respect to intestinal barrier integrity, loss of integrity of the intestinal epithelium plays a key pathogenic role in IBD. Maloy, Kevin J.; Powrie, Fiona, "Intestinal homeostasis and its breakdown in inflammatory bowel disease," (2011) Nature. 474 (7351): 298-306. It is hypothesized that detrimental changes in the intestinal microbiota induce an inappropriate or uncontrolled immune response that results in damage to the intestinal epithelium. Breaches in this critical intestinal epithelium barrier allow further infiltration of microbiota that, in turn, elicit further immune responses. Thus, IBD is a multifactorial disease that is driven in part by an exaggerated immune response to gut microbiota that can cause defects in epithelial barrier function.

Microbiome profiling of IBD patients has revealed distinct profiles such as increased Proteobacteria, including adherent-invasive E. coli, often at the expense of potentially beneficial microbes such as Roseburia spp (Machiels et al., 2014, Gut, 63:1275-1283; Patterson et al., 2017, Front Immunol, 8:1166; Shawki and McCole, 2017, Cell Mol Gastroenterol Hepatol, 3:41-50). Moreover, a decrease in Roseburia hominis was linked with dysbiosis in patients with ulcerative colitis. IBD affected individuals have been found to have 30-50 percent reduced biodiversity of commensal bacteria, such as decreases in Firmicutes (namely Lachnospiraceae) and Bacteroidetes. Further evidence of the role of gut flora in the cause of inflammatory bowel disease is that IBD affected individuals are more likely to have been prescribed antibiotics in the 2-5 year period before their diagnosis than unaffected individuals. See, Aroniadis O C, Brandt L J, "Fecal microbiota transplantation: past, present and future," (2013) Curr. Opin. Gastroenterol. 29 (1) (2013): 79-84.

Protective bacterial communities, probiotics and bacterially derived metabolites have been demonstrated to improve disease in various clinical and pre-clinical studies. For example, fecal microbial transfer (FMT) experiments have shown some success in IBD patients, although challenges still exist with FMT (Moayyedi et al., 2015, Gastroenterology, 149:102-109 e106; Qazi et al., 2017, Gut Microbes, 8:574-588; Narula et al., 2017, Inflamm Bowel Dis, 23:1702-1709). In other studies treatment with probiotics including VSL #3, Lactobacillus spp. and Bifidobacterium spp. have also shown to have beneficial effects in humans and animal models (Srutkova et al., 2015, PLoS One, 10:e0134050; Pan et al., 2014, Benef Microbes, 5:315-322; Huynh et al., 2009, Inflamm Bowel Dis, 15:760-768; Bibiloni et al., 2005, Am J Gastroenterol, 100:1539-1546). Furthermore, bacterial products such as p40 from L. rhamnosus GG and Amuc-1100 from A. muciniphila have been shown to promote barrier function and protect in animal models of IBD and metabolic disease, receptively (Yan et al., 2011, J Clin Invest, 121:2242-2253; Plovier et al., Nat Med, 23:107-113).

While uses of live microbial populations to treat diseases is increasingly common, such methods rely on the ability of the administered bacteria to survive in the host or patient and to interact with the host tissues in a beneficial and therapeutic way. An alternative approach, provided here, is to identify microbially-encoded proteins and variants thereof which can affect cellular functions in the host and provide therapeutic benefit. Such proteins can be administered, for example, as pharmaceutical compositions comprising a substantially isolated or purified therapeutic, bacterially-derived protein or as a live biotherapeutic (bacterium) engineered to express the therapeutic protein as an exogenous protein. Moreover, methods of treatment comprising administration of the therapeutic protein are not limited to the gut (small intestine, large intestine, rectum) but may also include treatment of other disorders within the alimentary canal such as oral mucositis.

To identify microbially-derived proteins which may have therapeutic application in gastrointestinal inflammatory disorders, mucosal biopsies from humans who were healthy or who were diagnosed with IBD (UC) were analyzed to determine the microbial compositions of these mucosal biopsies. A comparison of the bacterial profiles from healthy vs. diseased subjects identified bacteria that were either likely to be beneficial (greater numbers in healthy vs. diseased) or detrimental (lower numbers in healthy vs. diseased). Among the bacterial species identified as beneficial was Eubacterium eligens and Clostridium bartlettii. Extensive bioinformatics analysis was then performed to predict proteins encoded by the bacterium and then to identify those proteins which are likely to be secreted by the bacterium. Proteins which were predicted to be secreted proteins were then characterized using a series of in vitro assays to study the effect of each protein on epithelial barrier integrity, cytokine production and/or release, and wound healing. Proteins identified as having activity which may facilitate maintenance or repair of epithelial barrier integrity were then assessed in an in vivo mouse model for colitis. These proteins, identified herein as "SG-15," "SG-16," SG-17" and SG-18," demonstrated in vitro and/or in vivo activity indicative of its ability to provide therapeutic benefit for improving epithelial barrier integrity and for treating diseases and disorders associated with epithelial barrier integrity as well as treating inflammatory gastrointestinal diseases such as IBDs, as described in more detail below.

The SG-15 Protein

A protein referred to herein as SG-15 is 400 amino acid residues in length (SEQ ID NO:1) and is encoded by a nucleotide sequence (provided as SEQ ID NO:2) present in the genome of *Eubacterium eligens*. A complete genomic sequence for an *E. eligens* strain can be found at GenBank accession number CP001104 (the sequence incorporated herein by reference in its entirety). A 16S rRNA gene sequence for the *E. eligens* strain can be found at GenBank accession number NR_074613. A predicted full-length protein (including a predicted signal sequence) encoded by the *E. eligens* genomic sequence is 494 amino acids in length (SEQ ID NO:5), encoded by SEQ ID NO:6. An alternate predicted full-length protein is 475 amino acids in length (SEQ ID NO:7), encoded by SEQ ID NO:8. Recombinant SG-15 can be expressed with an N-terminal methionine (encoded by the codon ATG). For example, recombinantly expressed SG-15 can be 401 amino acids in length (SEQ ID NO:3), encoded by SEQ ID NO:4 (1203 bp). SG-15 refers to the above proteins and variants thereof as taught herein.

The SG-16 Protein

A protein referred to herein as SG-16 is 119 amino acid residues in length (SEQ ID NO:9) and is encoded by a nucleotide sequence (provided as SEQ ID NO:10) present in the genome of *Eubacterium eligens* (e.g., GenBank accession number CP001104). A predicted full-length protein (including a predicted signal sequence) encoded by the *E. eligens* genomic sequence is 143 amino acids in length (SEQ ID NO:11), encoded by SEQ ID NO:12. SG-16 refers to the above proteins and variants thereof as taught herein.

The SG-17 Protein

A protein referred to herein as SG-17 is 327 amino acid residues in length (SEQ ID NO:13) and is encoded by a nucleotide sequence (provided as SEQ ID NO:14) present in the genome of *Eubacterium eligens* (e.g., GenBank accession number CP001104). A predicted full-length protein (including a predicted signal sequence) encoded by the *E. eligens* genomic sequence is 345 amino acids in length (SEQ ID NO:17), encoded by SEQ ID NO:18. Recombinant SG-17 can be expressed with an N-terminal methionine (encoded by the codon ATG). For example, recombinantly expressed SG-17 can be 328 amino acids in length (SEQ ID NO:15), encoded by SEQ ID NO:16. SG-17 refers to the above proteins and variants thereof as taught herein.

The SG-18 Protein

A protein referred to herein as SG-18 is 267 amino acid residues in length (SEQ ID NO:19) and is encoded by a nucleotide sequence (provided as SEQ ID NO:20) present in the genome of *Clostridium bartlettii* sp. nov. A genomic sequence for a *C. bartlettii* strain can be found at GenBank accession number FUXV01000001 (the sequence incorporated herein by reference in its entirety). A predicted full-length protein (including a predicted signal sequence) encoded by the *C. bartlettii* genomic sequence is 290 amino acids in length (SEQ ID NO:23), encoded by SEQ ID NO:24. An alternate predicted full-length protein is 279 amino acids in length (SEQ ID NO:25), encoded by SEQ ID NO:26. Recombinant SG-18 can be expressed with an N-terminal methionine (encoded by the codon ATG). For example, recombinantly expressed SG-18 can be 268 amino acids in length (SEQ ID NO:21), encoded by SEQ ID NO:22. SG-18 refers to the above proteins and variants thereof as taught herein.

The SG-15, SG-16, SG-17 and SG-18 proteins can be recombinantly expressed in commercially available and routinely used expression vectors and host cells. For example, these SG proteins used in the Examples below were expressed using a pGEX expression vector which expresses the protein of interest with a GST tag and protease site which is cleaved after expression and purification. This expression system can result in a protein, after cleavage with a protease, with an N-terminus which differs with respect to a few amino acid residues relative to the wildtype protein. Moreover, a few exogenous amino acid residues may be present at the C-terminus of the protein. Alternative expression systems include but are not limited to a pET-28 expression vector which adds an N-terminal FLAG tag, and a pD451 expression vector which can be used to express an SG protein having no exogenous N-terminal or C-terminal amino acids. Experiments performed and repeated with these proteins can show that the minor N-terminal and/or C-terminal variations resulting from the use of the different protein expression systems and DNA constructs retain equivalent functional activity in in vivo and in vitro assays. It is understood that unless otherwise indicated, for each of SG-15, SG-16, SG-17 and SG-18, the term "SG-number" refers herein to the amino acid sequence depicted herein as SEQ ID NO:1, SEQ ID NO:9, SEQ ID NO:13, or SEQ ID NO:19 respectively, and such variants of the specified SG protein comprising an amino acid sequence as taught herein. For example, SG protein variants can include variations in amino acid residues (substitution, insertion, deletion) as well as modifications such as fusion constructs and post-translational modifications (phosphorylation, glycosylation, etc.). Some exemplary embodiments of the SG proteins and encoding nucleic acids are provided in Table 1 below.

TABLE 1

| Amino Acid Sequence | Encoding Nucleic Acid Sequence |
|---|---|
| SEQ ID NO: 1 (SG-15) | SEQ ID NO: 2 (SG-15) |
| EYTEIRTASELVEAAKS | GAATACACAGAAATCCGAACAGCGTCAGAACTTGTGGA |
| ASGNYKLMTDIDMTGV | AGCAGCTAAGAGTGCGTCAGGAAATTATAAACTGATGA |
| EWTPWDFSGTFDGNGH | CAGATATAGATATGACAGGAGTTGAGTGGACGCCATGG |
| SILNLSVKTVSKKTMKT | GATTTTTCGGGAACATTTGACGGTAACGGACACAGCAT |
| YDGNRKEYKTYGAGFF | ACTTAACCTGTCAGTAAAGACAGTAAGCAAGAAGACAA |
| GVLTGAKVTGLDIYGA | TGAAGACCTATGACGGCAACAGAAAAGAGTACAAAAC |
| RIEITTTEPCFAAPIAGLA | ATACGGCGCAGGCTTCTTTGGGGTGCTTACAGGTGCGA |
| DDSDISDCIIKDTYVSLT | AAGTAACAGGACTGGATATATATGGAGCAAGAATTGAG |
| DSAKMWGTGGIAGFGS | ATTACTACAACGGAACCATGTTTTGCGGCACCAATAGC |
| GNLDNITTDVTLVCVDT | AGGGCTTGCAGACGACAGCGACATATCAGACTGTATAA |
| DAAVRDEQFMGGAYA | TTAAGGATACATATGTGTCACTCACAGATTCAGCTAAA |
| AGFLNIRNCSITIDGYDS | ATGTGGGGAACAGGCGGAATCGCTGGATTTGGAAGCGG |
| DHGYVHDGGLVGMYM | CAATCTTGATAATATTACTACAGATGTGACACTTGTATG |
| VYPLELSKTYQGEVLNN | TGTAGATACAGACGCAGCGGTCAGGGACGAGCAGTTCA |
| KVKGMITFFEDNTDRRA | TGGGAGGCGCGTATGCAGCAGGTTTCCTTAATATAAGG |

TABLE 1-continued

| Amino Acid Sequence | Encoding Nucleic Acid Sequence |
|---|---|
| YCQANMGEVMNWTYA YSGFTSDFKRNETYDYS VTLLPEMCSNPSYTDVV TEATASDFGYTTHTCST CGYTYSDTYTIHEHKVD SYSVVKEAASTDKKDGI EAGTCSLCNQTVYREY AANVVTDDNTQATDNK ASGTAVKKGMKESTAV FA | AATTGTTCTATAACAATAGATGGATATGATTCAGACCA CGGATATGTGCATGATGGCGGACTTGTCGGCATGTATA TGGTATATCCATTGGAACTGTCAAAGACATATCAGGGC GAAGTGCTTAACAACAAAGTTAAGGGAATGATAACATT TTTCGAAGACAATACAGACCGCCGTGCATACTGTCAGG CAAATATGGGTGAGGTCATGAACTGGACATATGCTAT TCAGGCTTCACATCAGATTTTAAGAGAAATGAGACATA TGATTATTCAGTGACACTGCTTCCGGAAATGTGCAGCA ATCCTTCATACACAGATGTAGTGACAGAAGCAACAGCA TCAGACTTTGGATACACAACACACCTGCAGTACATG TGGCTACACATATTCAGACACTTACACAATACATGAGC ATAAGGTCGACAGTTACAGCGTGGTAAAGGAAGCAGCC AGCACAGACAAGAAAGACGGAATAGAGGCAGGAACAT GCAGCCTGTGCAATCAGACAGTTTACAGGGAATATGCT GCAAATGTAGTAACAGACGATAATACACAGGCAACAG ACAATAAAGCATCAGGCACGGCTGTCAAAAAAGGAAT GAAAGAAAGTACAGCAGTATTTGCA |
| SEQ ID NO: 9 (SG-16) MTGCSGSKEPDNKTSV DYTVVENADLPEELKKL IESKKDKVMRLTYTTKD YTYVVAGYGTRETSGY SIKVNDVYTGDNALYID LNLIGPAAGEAVNEVET YPVIVLKMERREESVVF KM | SEQ ID NO: 10 (SG-16) ATGACAGGGTGTTCTGGCAGCAAAGAGCCAGATAATAA GACCAGTGTTGATTATACAGTGGTTGAAAATGCAGACC TGCCGGAAGAGCTTAAGAAGCTTATTGAAAGCAAAAAA GATAAAGTGATGAGGCTTACATACACGACTAAGGATTA TACATATGTTGTGGCCGGTTATGGAACAAGGGAAACAA GTGGATATTCAATTAAGGTAAATGATGTATACACAGGA GATAATGCACTATACATTGATCTTAATCTGATAGGTCCG GCAGCGGGGGAAGCTGTAAATGAGGTTGAGACATATCC GGTAATAGTGCTTAAGATGGAAAGACGTGAAGAAAGC GTTGTTTTTAAAATG |
| SEQ ID NO: 13 (SG-17) CNSKIDVKYDYNVEDY VQLGQYENISVQVDKTS IENELIESKIKQDVEDNT TYTEVDRGAIASDQILV TYTATSSGASLSGLTNT DGKTMILGTDTLGLELD ELDQALYGMTPGQTKIL IVDIPEDYSSDLYKGTRV VFELTMQTVAQANVPM ITNAYVKEAFGYDTVEE YRQSIKESLETDINSKVE NKIQEDVLSSLQDTFKIS SYPDSLMEETRSRLETSI GFYADFSNLSKDEYCQK QYGLSFDDFVKKSVVQ QLIMEAIVKDRNMTMR EYDYKGSLDDFAADNG YSNADTFVEKFGKDKIV KAMLVQKAQDYVIEHA NISYK | SEQ ID NO: 14 (SG-17) TGTAATAGTAAGATTGATGTTAAGTATGATTATAATGTT GAAGATTATGTTCAGCTTGGACAGTATGAAAACATATC AGTCCAGGTAGATAAAACTTCAATAGAGAATGAACTTA TAGAGAGTAAAATTAAACAGGATGTAGAAGATAATACT ACTTATACAGAAGTTGACAGAGGTGCAATAGCTTCTGA TCAGATTCTTGTTACATATACTGCTACATCTTCAGGCGC ATCTCTTAGCGGACTTACTAATACAGATGGTAAAACAA TGATTCTTGGAACGGATACTCTCGGACTTGAACTTGATG AGTTAGATCAGGCTTTATATGGTATGACCCCAGGTCAG ACAAAGATACTTATTGTTGATATACCTGAGGATTATAGT TCGGATTTATATAAGGGCACGAGGGTTGTATTTGAACTT ACAATGCAGACAGTTGCACAGGCAAATGTTCCAATGAT AACTAATGCATATGTTAAGGAAGCGTTTGGATATGATA CCGTTGAAGAATATAGACAGTCAATAAAGGAATCTCTT GAAACTGATATTAATTCAAAGGTTGAGAACAAGATACA GGAAGATGTATTATCTTCTTTACAGGATACATTCAAGAT AAGCAGTTATCCTGATTCACTTATGGAAGAAACAAGAT CCAGACTTGAAACATCTATTGGTTTCTATGCGGATTTTT CAAATCTTTCAAAGGATGAATACTGTCAGAAGCAGTAT GGACTTTCTTTTGATGACTTTGTTAAGAAATCTGTTGTA CAGCAGCTTATCATGGAGGCTATAGTTAAAGACCGCAA TATGACAATGAGAGAATACGATTATAAAGGTTCTCTTG ATGATTTTGCGGCAGATAATGGATATTCTAATGCGGAT ACATTTGTTGAAAAATTCGGAAAAGATAAGATTGTAAA GGCTATGCTTGTGCAGAAGGCACAGGATTATGTTATTG AGCATGCCAATATTTCTTATAAG |
| SEQ ID NO: 19 (SG-18) EVDSSKEQATSKDEKQV VVATSVAITEILDRLGVE VSGVPQTSYELPESAKG ATEIGSPMNPDMEIIKSL NPTDVICVDTLGSDFEK QFEENNINADFYNLSNV DGLKETIAALGEKFNKQ DKANEILDEIKEVENKV NSNKKSDDKILVLFGAP GSVMVATDKSYIGNLV ELAGGNNIFSNATSSFTQ INLEEIIKLNPDKILVMT HAVPEAAKKSVEEELSK DLWKNVNAVKNNDITY LENGYFGMSANLQIVEA VEKLGDILYE | SEQ ID NO: 20 (SG-18) GAGGTAGATAGTTCTAAAGAACAAGCTACATCAAAAGA TGAAAAACAAGTAGTAGTAGCTACATCAGTTGCAATTA CTGAAATATTAGATAGGTTAGGTGTAGAAGTTAGTGGT GTACCACAAACTAGCTATGAACTTCCAGAAAGTGCAAA AGGTGCTACGGAAATTGGAAGTCCAATGAATCCAGATA TGGAAATAATAAAATCACTAAATCCAACAGACGTAATA TGTGTTGATACTTTAGGAAGTGATTTTGAAAAACAATTT GAAGAAAACAATATAAATGCTGATTTTTATAATCTAAG CAATGTAGACGGATTAAAAGAAACAATAGCTGCTTTAG GAGAAAAATTCAATAAACAAGATAAAGCAAATGAAAT ATTAGATGAAATAAAAGAAGTAGAAAATAAAGTTAATT CTAATAAAAAATCTGATGATAAGATCTTAGTATTATTTG GAGCACCAGGAAGTGTAATGGTAGCTACGGACAAAAGT TATATAGGAAACTTAGTCGAGTTAGCTGGAGGAAATAA TATATTCTCAAATGCAACTAGCTCATTTACTCAAATAAA CTTAGAAGAAATAATAAAGTTAAATCCAGATAAAATAT TAGTTATGACTCATGCCGTTCCAGAGGCTGCAAAAAAA TCTGTAGAAGAAGAATTAAGTAAAGACCTTTGGAAAAA TGTAAATGCAGTTAAAAATAACGATATAACTTATTTAG |

TABLE 1-continued

| Amino Acid Sequence | Encoding Nucleic Acid Sequence |
|---|---|
| | AAAATGGTTATTTCGGAATGAGTGCAAACTTACAAATA GTTGAGGCAGTAGAAAAATTAGGAGATATATTATATGA G |

Epithelial Barrier Function in Disease

Studies in recent years have identified a major role of both genetic and environmental factors in the pathogenesis of IBD. Markus Neurath, "Cytokines in Inflammatory Bowel Disease," Nature Reviews Immunology, Vol. 14., 329-342 (2014). A combination of these IBD risk factors seems to initiate detrimental changes in epithelial barrier function, thereby allowing the translocation of luminal antigens (for example, bacterial antigens from the commensal microbiota) into the bowel wall. Id. Subsequently, aberrant and excessive responses, such as increased pro-inflammatory cytokine release, to such environmental triggers cause subclinical or acute mucosal inflammation in a genetically susceptible host. Id. Thus, the importance of proper epithelial barrier function in IBD is apparent, for in subjects that fail to resolve acute intestinal inflammation, chronic intestinal inflammation develops that is induced by the uncontrolled activation of the mucosal immune system. In particular, mucosal immune cells, such as macrophages, T cells, and the subsets of innate lymphoid cells (ILCs), seem to respond to microbial products or antigens from the commensal microbiota by, e.g., producing cytokines that can promote chronic inflammation of the gastrointestinal tract. Consequently, restoring proper epithelial barrier function to patients may be critical in resolving IBD.

The therapeutic activity of the SG proteins was assessed in part by its effects on epithelial barrier function both in vitro and in vivo. As shown in Examples 1B, 2B, 3B and 4B, SG protein activity was evaluated for effects on epithelial barrier integrity as shown by an in vitro trans-epithelial electrical resistance (TEER) assay. TEER assays are well-known methods for measuring effects on the structural and functional integrity of an epithelial cell layer (Srinivasan et al., 2015, J Lab Autom, 20:107-126; Beduneau et al., 2014, Eur J Pharm Biopharm, 87:290-298; Zolotarevsky et al., 2002, Gastroenterology, 123:163-172; Dewi, et al. (2004) J. Virol. Methods. 121:171-180, and in Mandic, et al. (2004) Clin. Exp. Metast. 21:699-704.). The assay performed and described herein consists of an epithelial monolayer made up of enterocyte and goblets cells to more accurately model the structural and functional components of the intestinal epithelium. The cells are cultured until tight junction formation occurs and barrier function capacity is assessed by a measurement of trans-epithelial electrical resistance. Upon addition of an insult, such as heat killed E. coli, there is a decrease in electrical resistance across the epithelial layer. Control reagents useful in the TEER assay include staurosporine and a myosin light chain kinase inhibitor. Staurosporine is a broad spectrum kinase inhibitor, originating from Streptomyces staurosporeus, which induces apoptosis. This reagent disrupts about 98% of the gap junctions leading to a decrease in electrical resistance in a TEER assay. Myosin light chain kinase (MLCK) is the terminal effector in a signaling cascade induced by pro-inflammatory cytokines, which results in contraction of the perijunctional actomyosin ring, resulting in separation of the gap junctions. By inhibiting MLCK, disruption of tight junctions is prevented. MLCK inhibitor in a TEER assay should reduce or prevent the reduction of electrical resistance in a TEER assay.

In some embodiments, the SG protein or variant or fragment thereof as described herein can be characterized by its ability to increase epithelial barrier function integrity as assessed by an in vitro TEER assay. The SG protein or variant or fragment thereof may increase electrical resistance in a TEER assay by at least about 10%, 20%, 30%, 40%, 50%, 60%, 70%, 80% or 90% as compared to the TEER assay performed in the absence of the protein.

In addition, Examples 1D, 2E, 3E and 4D assess effects of an SG protein on epithelial wound healing, an activity that can play a role in the maintenance or repair of and epithelial barrier such as an intestinal or mucosal epithelial barrier.

SG proteins were also characterized in an in vivo assay, specifically, the proteins were analyzed for their effects on pathological markers in a rodent model of IBD. Specifically, experiments were performed using a DSS (dextran sodium sulfate) animal model, a model well accepted for the study of agents on IBDs (Chassaign et al., 2014, Curr Protoc Imunol, 104:Unit-15.25; Kiesler et al., 2015, Cell Mol Gastroenterol Hepatol). DSS is a sulfated polysaccharide that is directly toxic to colonic epithelium and causes epithelial cell injury leading to loss of barrier function due to disrupted gap junctions. In these experiments, animals were treated with SG proteins prior to induction of colitis in the mouse. As a positive control, the mice were also treated with Gly2-GLP2, a stable analog of glucagon-like peptide 2 (GLP2). Gly2-GLP2 is known to promote epithelial cell growth and reduce colonic injury in experiment mouse colitis models. Results of the DSS studies show that the SG proteins affected markers such as epithelial barrier permeability, plasma levels of LPS binding protein, total body weight, and gross pathology.

Variants of SG Proteins

In another example, certain amino acids of the taught proteins may be substituted for other amino acids in a protein structure without appreciable loss of interactive binding capacity with structures such as, for example, binding sites on substrate molecules, receptors, antigen-binding regions of antibodies, and the like. Thus, these proteins would be biologically functional equivalents of the disclosed proteins (e.g. comprising SEQ ID NO:1, SEQ ID NO:9, SEQ ID NO:13 or SEQ ID NO:19, or variants thereof). So-called "conservative" changes do not disrupt the biological activity of the protein, as the structural change is not one that impinges on the protein's ability to carry out its designed function. It is thus contemplated by the inventors that various changes may be made in the sequence of genes and proteins disclosed herein, while still fulfilling the goals of the present disclosure.

In some embodiments, a modified or variant protein is provided which contains at least one non-naturally occurring amino acid substitution relative to the SG protein amino acid sequence (i.e., SEQ ID NO:1, SEQ ID NO:9, SEQ ID NO:13 or SEQ ID NO:19). In other embodiments, the variant protein comprises 1, 2, 3, 4, 5, 6, 7, 8, 9 or 10 amino acid substitutions relative to SEQ ID NO:1, SEQ ID NO:9, SEQ ID NO:13 or SEQ ID NO:19.

In some embodiments, the taught proteins have markedly different structural and/or functional characteristics, as compared to a protein comprising or consisting of SEQ ID NO:1, SEQ ID NO:9, SEQ ID NO:13 or SEQ ID NO:19.

The term "SG variant" as used herein can include SG proteins that are, e.g., not identical to a protein comprising the sequence of SEQ ID NO:1 (SG-15), SEQ ID NO:9 (SG-16), SEQ ID NO:13 (SG-17) or SEQ ID NO:19 (SG-18) and which are further modified such as by a PTM or fusion or linkage to a second agent, e.g., a protein or peptide.

Protein PTMs occur in vivo and can increase the functional diversity of the proteome by the covalent addition of functional groups or proteins, proteolytic cleavage of regulatory subunits or degradation of entire proteins. Isolated SG proteins prepared according to the present disclosure can undergo 1 or more PTMs in vivo or in vitro. The type of modification(s) depends on host cell in which the protein is expressed and includes but is not limited to phosphorylation, glycosylation, ubiquitination, nitrosylation (e.g., S-nitrosylation), methylation, acetylation (e.g., N-acetylation), lipidation (myristoylation, N-myristoylation, S-palmitoylation, farnesylation, S-prenylation, S-palmitoylation) and proteolysis may influence almost all aspects of normal cell biology and pathogenesis. The isolated and/or purified SG proteins or variants or fragments thereof as disclosed herein may comprise one or more the above recited post-translational modifications.

The SG protein or variant or fragment thereof may be a fusion protein in which the N- and/or C-terminal domain of the SG protein is fused to a second protein via a peptide bond. Commonly used fusion partners well known to the ordinarily skilled artisan include but are not limited to human serum albumin and the crystallizable fragment, or constant domain of IgG, Fc. In some embodiments, the SG protein or variant or fragment thereof is linked to a second protein or peptide via a disulfide bond, wherein the second protein or peptide comprises a cysteine residue.

As aforementioned, modifications and/or changes (e.g., substitutions, insertions, deletions) may be made in the structure of proteins disclosed herein. Thus, the present disclosure contemplates variation in sequence of these proteins, and nucleic acids coding therefore, where they are nonetheless able to retain substantial activity with respect to the functional activities assessed in various in vitro and in vivo assays as well as in therapeutic aspects of the present disclosure. In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity.

It is also contemplated that the SG protein or variant or fragment thereof is one which, when administered to a subject, can reduce disease-associated weight loss, improve the clinical pathology score, and/or minimize colon shortening in the subject. In some embodiments, the subject is a mammal which has genetically or clinically induced inflammatory disorder or dysfunctional epithelial barrier function. Alternatively, the animal has an idiopathic gastrointestinal disorder involving a decrease in epithelial barrier function or intestinal inflammatory disorder. In other embodiments, the mammal is a human, non-human primate, or a rodent. The rodent may be a mouse or rat.

In some embodiments, the SG protein or variant or fragment thereof according to the present disclosure is one which can modulate production of and/or secretion of a cytokine in an in vitro assay or in a subject administered the protein. In some embodiments, secretion of cytokines is reduced in vitro. Levels of cytokines produced and/or secreted in an in vitro assay or subject administered the protein are likely to be measured in the blood, serum, and/or plasma of the subject. Administration of the SG protein may result in a decrease in the serum levels of a pro-inflammatory cytokine such as one or more of TNF-α, IL-17, IL-1β, IL-2, IFN-γ, IL-6, IL-12, IL-25, IL-33, IL-8, MCP-1, MIP-3α, CXCL1, and IL-23. Alternatively, the cytokine may be an anti-inflammatory cytokine, in which case administration of the SG protein results in an increase in serum levels of an anti-inflammatory cytokine such as IL-4, IL-10, IL-13, IFN-α, and TGF-β.

In some embodiments, the SG protein or variant or fragment thereof has the functional ability to reduce gastrointestinal inflammation when administered to a subject such as a mammal (e.g., rodent, non human primate, or human). In other embodiments, the SG protein has the functional ability to reduce inflammatory (i.e. pro-inflammatory) cytokines, when administered to the subject. In yet other embodiments, the SG protein is able to reduce TNF-α and/or IL-23, when administered to the subject. In still other embodiments, the SG protein has the functional ability to increase anti-inflammatory cytokines, when administered to the subject. In some aspects, an SG protein of the disclosure is able to increase IL-10, when administered to the subject.

An SG protein or variant or fragment thereof according to the present disclosure is one which, when administered to a subject (e.g., rodent, non human primate, or human), can improve gastrointestinal epithelial cell barrier function, reduce disease-associated weight loss, improve clinical scores, improve colon length and/or colon weight-to-length readouts, induce or increase mucin gene expression (e.g., muc2 expression), increase the structural integrity and/or functionality of a gastrointestinal mucous barrier (e.g., in the small intestine, large intestine, mouth and/or esophagus), and/or reduce inflammation in the gastrointestinal tract.

In some embodiments, the SG protein or variant or fragment thereof resulting from such a substitution, insertion and/or deletion of amino acids relative to SEQ ID NO:1 (SG-15), SEQ ID NO:9 (SG-16), SEQ ID NO:13 (SG-17) or SEQ ID NO:19 (SG-18), maintains a level of functional activity which is substantially the same as that of the SG protein without the variation (e.g., is able to decrease epithelial barrier permeability in a DSS mouse model). The variant SG protein may be useful as a therapeutic for treatment or prevention of a variety of conditions, including, but not limited to inflammatory conditions and/or barrier function disorders, including, but not limited to, inflammation of the gastrointestinal (including oral, esophageal, and intestinal) mucosa, impaired intestinal epithelial cell gap junction integrity. In some embodiments, the modified SG protein has one or more of the following effects when administered to an individual suffering from, or predisposed to, an inflammatory condition and/or barrier function disorder: improvement of epithelial barrier integrity, e.g., following inflammation induced disruption; suppression of production of at least one pro-inflammatory cytokine (e.g., TNF-α and/or IL-23) by one or more immune cell(s); induction of mucin production in epithelial cells; and/or improvement of epithelial wound healing. Moreover, the modified or variant SG protein may be used for treatment or prevention of a disorder or condition such as, but not limited to, inflammatory bowel disease, ulcerative colitis, Crohn's disease, short bowel syndrome, GI mucositis, oral mucositis, chemotherapy-induced mucositis, radiation-induced mucositis, necrotizing enterocolitis, pouchitis, a metabolic disease, celiac disease, inflammatory bowel syndrome, or chemotherapy associated steatohepatitis (CASH).

As demonstrated in the Examples, in some embodiments, the SG protein can enhance epithelial wound healing. Accordingly, provided herein is a therapeutic SG protein comprising the amino acid sequence of SEQ ID NO:1, SEQ ID NO:9, SEQ ID NO: 13 or SEQ ID NO:19, or a variant or fragment thereof, wherein the SG protein can increase wound healing in an in vitro assay.

Methods of Treatment

The SG proteins described herein including variants (e.g., amino acid substitutions, deletions, insertions), modifications (e.g., glycosylation, acetylation), SG fragments and fusions thereof are contemplated for use in treating a subject diagnosed with or suffering from a disorder related to inflammation within the gastrointestinal tract and/or malfunction of epithelial barrier function within the gastrointestinal tract.

Provided herein are methods for treating a subject in need thereof comprising administering to the subject a pharmaceutical composition comprising an SG protein or fragment or variant thereof as described in the present disclosure. The subject can be one who has been diagnosed with inflammatory bowel disease, ulcerative colitis, pediatric UC, Crohn's disease, pediatric Crohn's disease, short bowel syndrome, mucositis GI mucositis, oral mucositis, mucositis of the esophagus, stomach, small intestine (duodenum, jejunum, ileum), large intestine (colon), and/or rectum, chemotherapy-induced mucositis, radiation-induced mucositis, necrotizing enterocolitis, pouchitis, a metabolic disease, celiac disease, irritable bowel syndrome, or chemotherapy associated steatohepatitis (CASH) Administration of the pharmaceutical compositions comprising an SG protein or fragment or variant thereof as described herein may also be useful for wound healing applications.

Inflammatory Bowel Disease

Inflammatory bowel disease (IBD) classically includes ulcerative colitis (UC) and Crohn's disease (CD). The pathogenesis of inflammatory bowel disease is not known. A genetic predisposition has been suggested, and a host of environmental factors, including bacterial, viral and, perhaps, dietary antigens, can trigger an ongoing enteric inflammatory cascade. Id. IBD can cause severe diarrhea, pain, fatigue, and weight loss. IBD can be debilitating and sometimes leads to life-threatening complications. Accordingly, in some embodiments, the method of treatment as described herein is effective to reduce, prevent or eliminate any one or more of the symptoms described above wherein the method comprises administering to a patient in need thereof a therapeutically effective amount of a pharmaceutical composition comprising the SG protein or variant or fragment thereof. In some embodiments, the method of treatment results in remission.

Ulcerative Colitis

Ulcerative colitis is an inflammatory bowel disease that causes long-lasting inflammation and sores (ulcers), in the innermost lining of your large intestine (colon) and rectum.

Ulcerative colitis typically presents with shallow, continuous inflammation extending from the rectum proximally to include, in many patients, the entire colon. Fistulas, fissures, abscesses and small-bowel involvement are absent. Patients with limited disease (e.g., proctitis) typically have mild but frequently recurrent symptoms, while patients with pancolitis more commonly have severe symptoms, often requiring hospitalization. Botoman et al., "Management of Inflammatory Bowel Disease," Am. Fain. Physician, Vol. 57(1):57-68 (Jan. 1, 1998) (internal citations omitted). Thus, ulcerative colitis is an IBD that causes long-lasting inflammation and sores (ulcers) in the innermost lining of your large intestine (colon) and rectum.

Crohn's Disease

Unlike ulcerative colitis, Crohn's disease can involve the entire intestinal tract, from the mouth to the anus, with discontinuous focal ulceration, fistula formation and perianal involvement. The terminal ileum is most commonly affected, usually with variable degrees of colonic involvement. Subsets of patients have perianal disease with fissures and fistula formation. Only 2 to 3 percent of patients with Crohn's disease have clinically significant involvement of the upper gastrointestinal tract. Botoman et al., "Management of Inflammatory Bowel Disease," Am. Fain. Physician, Vol. 57(1):57-68 (Jan. 1, 1998) (internal citations omitted). Thus, Crohn's disease is an IBD that causes inflammation of the lining of your digestive tract. In Crohn's disease, inflammation often spreads deep into affected tissues. The inflammation can involve different areas of the digestive tract, i.e. the large intestine, small intestine, or both. Collagenous colitis and lymphocytic colitis also are considered inflammatory bowel diseases, but are usually regarded separately from classic inflammatory bowel disease.

Clinical Parameters of Inflammatory Bowel Disease

As previously discussed, inflammatory bowel disease encompasses ulcerative colitis and Crohn's disease. There are numerous scores and clinical markers known to one of skill in the art that can be utilized to access the efficacy of the administered proteins described herein in treating these conditions.

There are two general approaches to evaluating patients with IBD. The first involves the visual examination of the mucosa and relies on the observation of signs of damage to the mucosa, in view of the fact that IBD is manifested by the appearance of inflammation and ulcers in the GI tract. Any procedure that allows an assessment of the mucosa can be used. Examples include barium enemas, x-rays, and endoscopy. An endoscopy may be of the esophagus, stomach and duodenum (esophagogastroduodenoscopy), small intestine (enteroscopy), or large intestine/colon (colonoscopy, sigmoidoscopy). These techniques are used to identify areas of inflammation, ulcers and abnormal growths such as polyps.

Scoring systems based on this visual examination of the GI tract exist to determine the status and severity of IBD, and these scoring systems are intended to ensure that uniform assessment of different patients occurs, despite the fact that patients may be assessed by different medical professionals, in diagnosis and monitoring of these diseases as well as in clinical research evaluations. Examples of evaluations based on visual examination of UC are discussed and compared in Daperno M et al (J Crohns Colitis. 2011 5:484-98).

Clinical scoring systems also exist, with the same purpose. The findings on endoscopy or other examination of the mucosa can be incorporated into these clinical scoring systems, but these scoring systems also incorporate data based on symptoms such as stool frequency, rectal bleeding and physician's global assessment. IBD has a variety of symptoms that affect quality of life, so certain of these scoring systems also take into account a quantitative assessment of the effect on quality of life as well as the quantification of symptoms.

One example of a scoring system for UC is the Mayo scoring system (Schroeder et al., N Eng J Med, 1987, 317:1625-1629), but others exist that have less commonly been used and include the Ulcerative Colitis Endoscopic Index of Severity (UCEIS) score (Travis et al, 2012, Gut, 61:535-542), Baron Score (Baron et al., 1964, BMJ, 1:89), Ulcerative Colitis Colonoscopic Index of Severity (UCCIS) (Thia et al., 2011, Inflamm Bowel Dis, 17:1757-1764), Rachmilewitz Endoscopic Index (Rachmilewitz, 1989, BMJ, 298:82-86), Sutherland Index (also known as the UC Disease Activity Index (UCDAI) scoring system; Sutherland et al., 1987, Gastroenterology, 92:1994-1998), Matts Score (Matts, 1961, QJM, 30:393-407), and Blackstone Index (Blackstone, 1984, Inflammatory bowel disease. In: Blackstone M O (ed.) Endoscopic interpretation: normal and pathologic appearances of the gastrointestinal tract, 1984, pp. 464-494). For a review, see Paine, 2014, Gastroenterol Rep 2:161-168. Accordingly, also contemplated herein is a method for treating a subject diagnosed with and suffering from UC, wherein the treatment comprises administering an SG protein or variant or fragment thereof as described herein and wherein the treatment results in a decrease in the UC pathology as determined by measurement of the UCEIS score, the Baron score, the UCCIS score, the Rachmilewitz Endoscopic Index, the Sutherland Index, and/or the Blackstone Index.

An example of a scoring system for CD is the Crohn's Disease Activity Index (CDAI) (Sands B et al 2004, N Engl J Med 350 (9): 876-85); most major studies use the CDAI in order to define response or remission of disease. Calculation of the CDAI score includes scoring of the number of liquid stools over 7 days, instances and severity of abdominal pain over 7 days, general well-being over 7 days, extraintestinal complications (e.g., arthritis/arthralgia, iritis/uveitis, erythema nodosum, pyoderma gangrenosum, aphtous stomatitis, anal fissure/fistula/abscess, and/or fever >37.8° C.), use of antidiarrheal drugs over 7 days, present of abdominal mass, hematocrit, and body weight as a ratio of ideal/observed or percentage deviation from standard weight. Based on the CDAI score, the CD is classified as either asymptomatic remission (0 to 149 points), mildly to moderately active CD (150 to 220 points), moderately to severely active CD (221 to 450 points), or severely active fulminant disease (451 to 1000 points). In some embodiments, the method of treatment comprising administering to a patient diagnosed with CD a therapeutically effective amount of an SG protein or variant or fragment thereof results in a decrease in a diagnostic score of CD. For example, the score may change the diagnosis from severely active to mildly or moderately active or to asymptomatic remission.

The Harvey-Bradshaw index is a simpler version of the CDAI which consists of only clinical parameters (Harvey et al., 1980, Lancet 1(8178):1134-1135). The impact on quality of life is also addressed by the Inflammatory Bowel Disease Questionnaire (IBDQ) (Irvine et al., 1994, Gastroenterology 106: 287-296). Alternative methods further include CDEIS and SES CD (see, e.g., Levesque, et al. (2015) Gastroenterol. 148:37 57).

In some embodiments, a method of treating an IBD, e.g., UC, is provided wherein the treatment is effective in reducing the Mayo Score. The Mayo Score is a combined endoscopic and clinical scale used to assess the severity of UC and has a scale of 1-12 The Mayo Score is a composite of subscores for stool frequency, rectal bleeding, findings of flexible proctosigmoidoscopy or colonoscopy, and physician's global assessment (Paine, 2014, Gastroenterol Rep 2:161-168). With respect to rectal bleeding, blood streaks seen in the stool less than half the time is assigned 1 point, blood in most stools is assigned 2 points and pure blood passed is assigned 3 points. Regarding stool frequency, a normal number of daily stools is assigned 0 points, 1 or 2 more stools than normal is assigned 1 point, 3 or 4 more stools than normal is assigned 2 points, and 5 or more stools than usual is assigned 3 points. With respect to the endoscopy component, a score of 0 indicates normal mucosa or inactive UC, a score of 1 is given for mild disease with evidence of mild friability, reduced vascular pattern, and mucosal erythema, a score of 2 is given for moderate disease with friability, erosions, complete loss of vascular pattern, and significant erythema, and a score of 3 is given for ulceration and spontaneous bleeding (Schroeder et al., 1987, N Engl J Med, 317:1625-1629). Global assessment by a physician assigns 0 points for a finding of normal, 1 point for mild colitis, 2 points for moderate colitis and 3 points for severe colitis. Accordingly, in some embodiments, a patient treated with an SG therapeutic protein or variant or fragment thereof is successfully treated when the patient experiences a reduction in the Mayo Score by at least 1, 2 or 3 points in at least one of: rectal bleeding, blood streaks seen in the stool, endoscopy subscore and physician's global assessment. In some embodiments, the method of treatment comprising administering to a patient diagnosed with UC a therapeutically effective amount of an SG protein or variant or fragment thereof results in a decrease in a diagnostic score of UC. For example, the score may change a diagnostic score, e.g., Mayo Score, by at least 1, 2, 3, 4, 5, 6, 7, 8, 9, 10 or 11 points.

Pouchitis

Additionally or alternatively, the compositions comprising an SG therapeutic protein or variant and methods of administration as described herein can be used to treat pouchitis. Pouchitis is an inflammation of the lining of a pouch that is surgically created in the treatment of UC. Specifically, subjects having serious UC may have their diseased colon removed and the bowel reconnected by a procedure called ileoanal anastomosis (IPAA) or J-pouch surgery. Pouchitis cases can recur in many patients, manifesting either as acute relapsing pouchitis or chronic, unremitting pouchitis. Accordingly, provided herein are methods for treating pouchitis, acute pouchitis or recurrent pouchitis.

Pouchitis activity can be classified as remission (no active pouchitis), mild to moderately active (increased stool frequency, urgency, and/or infrequent incontinence), or severely active (frequent incontinence and/or the patient is hospitalized for dehydration). The duration of pouchitis can be defined as acute (less than or equal to four weeks) or chronic (four weeks or more) and the pattern classified as infrequent (1-2 acute episodes), relapsing (three or fewer episodes) or continuous. The response to medical treatment can be labeled as treatment responsive or treatment refractory, with the medication for either case being specified. Accordingly, in some embodiments, a method for treating a subject diagnosed with pouchitis is provided wherein treatment with a pharmaceutical composition comprising an SG protein or variant or fragment thereof results in a decrease in the severity of the pouchitis and/or results in remission.

Mucositis and Mucosal Barriers

The mucosa of the gastrointestinal (GI) tract is a complex microenvironment involving an epithelial barrier, immune cells, and microbes. A delicate balance is maintained in the healthy colon. Luminal microbes are physically separated from the host immune system by a barrier consisting of epithelium and mucus. The pathogenesis of IBD, although not fully elucidated, may involve an inappropriate host response to an altered commensal flora with a dysfunctional mucous barrier. See, Boltin et al., "Mucin Function in Inflammatory Bowel Disease an Update," J. Clin. Gastroenterol., Vol. 47(2):106-111 (February 2013).

Mucositis occurs when cancer treatments (particularly chemotherapy and radiation) break down the rapidly divided epithelial cells lining the intestinal tract (which goes from the mouth to the anus), leaving the mucosal tissue open to ulceration and infection. Mucosal tissue, also known as mucosa or the mucous membrane, lines all body passages that communicate with the air, such as the respiratory and alimentary tracts, and have cells and associated glands that secrete mucus. The part of this lining that covers the mouth, called the oral mucosa, is one of the most sensitive parts of the body and is particularly vulnerable to chemotherapy and radiation. The oral cavity is the most common location for mucositis. While the oral mucosa is the most frequent site of mucosal toxicity and resultant mucositis, it is understood that mucositis can also occur along the entire alimentary tract including the esophagus, stomach, small intestine (duodenum, jejunum, ileum), large intestine (colon), and rectum. In some embodiments, a pharmaceutical composition comprising an SG protein or a variant or fragment thereof is therapeutically effective to treat mucositis of the mouth, esophagus, stomach, small intestine (duodenum, jejunum, ileum), large intestine (colon), and/or rectum Oral mucositis can lead to several problems, including pain, nutritional problems as a result of inability to eat, and increased risk of infection due to open sores in the mucosa. It has a significant effect on the patient's quality of life and can be dose-limiting (i.e., requiring a reduction in subsequent chemotherapy doses). The World Health Organization has an oral toxicity scale for diagnosis of oral mucositis: Grade 1: soreness±erythema, Grade 2: erythema, ulcers; patient can swallow solid food; Grade 3: ulcers with extensive erythema; patient cannot swallow solid food; Grade 4: mucositis to the extent that alimentation is not possible. Grade 3 and Grade 4 oral mucositis is considered severe mucositis. Accordingly, provided herein is a method for treating a subject diagnosed with oral mucositis, wherein administration of a pharmaceutical composition comprising an SG protein or a variant or fragment thereof reduces the grade of oral toxicity by at least 1 point of the grade scale of 1 to 4.

Colon Shortening

Ulcerative colitis is an idiopathic inflammatory bowel disease that affects the colonic mucosa and is clinically characterized by diarrhea, abdominal pain and hematochezia. The extent of disease is variable and may involve only the rectum (ulcerative proctitis), the left side of the colon to the splenic flexure, or the entire colon (pancolitis). The severity of the disease may also be quite variable histologically, ranging from minimal to florid ulceration and dysplasia. Carcinoma may develop. The typical histological (microscopic) lesion of ulcerative colitis is the crypt abscess, in which the epithelium of the crypt breaks down and the lumen fills with polymorphonuclear cells. The lamina propria is infiltrated with leukocytes. As the crypts are destroyed, normal mucosal architecture is lost and resultant scarring shortens and can narrow the colon. Thus, colon shortening can be a consequence of colitis disease and is often used diagnostically. For example, non-invasive plain abdominal x-rays can demonstrate the gaseous outline of the transverse colon in the acutely ill patient. Shortening of the colon and loss of haustral markings can also be demonstrated by plain films, as well as a double-contrast barium enema. Indications of ulcerative disease include loss of mucosal detail, cobblestone filling defects, and segmental areas of involvement. See, "Ulcerative Colitis: Introduction—Johns Hopkins Medicine," found at: www.hopkinsmedicine.org/gastroenterology_hepatology/_pdfs/small_large_intestine/ulcerative_colitis.pdf.

Further, art recognized in vivo models of colitis will utilize shortening of colon length in scoring the severity of colitis in the model. See, Kim et al., "Investigating Intestinal Inflammation in DSS-induced Model of IBD," Journal of Visualized Experiments, Vol. 60, pages 2-6 (February 2012).

Epithelial Barrier Function in Non-IBD Disease

An improperly functioning epithelial barrier is increasingly implicated in, e.g., IBDs and mucositis. Moreover, there are numerous other diseases that studies have shown are also caused, linked, correlated, and/or exacerbated by, an improperly functioning epithelial barrier. These diseases include: (1) metabolic diseases, including-obesity, type 2 diabetes, non-alcoholic steatohepatitis (NASH), non-alcoholic fatty liver disease (NAFLD), liver disorders, and alcoholic steatohepatitis (ASH); (2) celiac disease; (3) necrotizing enterocolitis; (4) irritable bowel syndrome (IBS); (5) enteric infections (e.g. *Clostridium difficile*); (6) other gastro intestinal disorders in general; (7) interstitial cystitis; (8) neurological disorders or cognitive disorders (e.g. Alzheimer's, Parkinson's, multiple sclerosis, and autism); (9) chemotherapy associated steatohepatitis (CASH); and (10) pediatric versions of the aforementioned diseases. See, e.g.: Everard et al., "Responses of Gut Microbiota and Glucose and Lipid Metabolism to Prebiotics in Genetic Obese and Diet-Induced Leptin-Resistant Mice," Diabetes, Vol. 60, (November 2011), pgs. 2775-2786; Everard et al., "Cross-talk between Akkermansia muciniphila and intestinal epithelium controls diet-induced obesity," PNAS, Vol. 110, No. 22, (May 2013), pgs. 9066-9071; Cani et al., "Changes in Gut Microbiota Control Metabolic Endotoxemia-Induced Inflammation in High-Fat Diet-Induced Obesity and Diabetes in Mice," Diabetes, Vol. 57, (June 2008), pgs. 1470-1481; Delzenne et al., "Targeting gut microbiota in obesity: effects of prebiotics and probiotics," Nature Reviews, Vol. 7, (November 2011), pgs. 639-646. Consequently, restoring proper epithelial barrier function to patients may be critical in resolving the aforementioned disease states.

A properly functioning epithelial barrier in the lumen of the alimentary canal, including the mouth, esophagus, stomach, small intestine, large intestine, and rectum, is critical in controlling and maintaining the microbiome within the gastrointestinal tract and alimentary canal. The ecosystem for the microbiome includes the environment, barriers, tissues, mucus, mucin, enzymes, nutrients, food, and communities of microorganism, that reside in the gastrointestinal tract and alimentary canal. The integrity and permeability of the intestinal mucosal barrier impacts health in many critical ways.

A loss of integrity of the mucosal barrier in gastrointestinal disorders due to changes in mucin secretion may be related to host immune changes, luminal microbial factors, or directly acting genetic or environmental determinants. Thus, the disequilibrium of the mucous barrier may be central to the pathogenesis of IBD. Boltin et al., "Mucin Function in Inflammatory Bowel Disease an Update," J. Clin. Gastroenterol., Vol. 47(2):106-111 (February 2013).

Mucins are the primary constituent of the mucous layer lining the GI tract. There are at least 21 mucin (MUC) genes known in the human genome, encoding either secreted or membrane-bound mucins. The predominant mucins in the normal colorectum are MUC1, MUC2, MUC3A, MUC3B, MUC4, MUC13, and MUC17.1 MUC2 is the primary secretory, gel-forming component of intestinal mucus, produced in goblet cells. See, Boltin et al., "Mucin Function in Inflammatory Bowel Disease an Update," J. Clin. Gastroenterol., Vol. 47(2):106-111 (February 2013). Along with additional secreted mucins such as MUC1, 3A, 3B, 4, 13 and 17.1, goblet cell secretion of MUC2 forms a protective barrier on colonic epithelial cells reducing exposure to intestinal contents which may damage epithelial cells or prime immune responses.

Inflammatory Mechanisms in IBDs

There is significant evidence showing that certain cytokines are involved with IBD. Recent studies have demonstrated that cytokines play a crucial role in the pathogenesis of inflammatory bowel diseases (IBDs), such as Crohn's disease and ulcerative colitis, where they control multiple aspects of the inflammatory response. Markus Neurath, "Cytokines in Inflammatory Bowel Disease," Nature Reviews Immunology, Vol. 14., 329-342 (2014). In particular, the imbalance between pro-inflammatory and anti-inflammatory cytokines that occurs in IBD impedes the resolution of inflammation and instead leads to disease perpetuation and tissue destruction. Id. Recent studies suggest the existence of a network of regulatory cytokines that has important implications for disease progression. Id. Accordingly, experiments were performed to study the effects of an SG protein on production and/or secretion of pro-inflammatory and anti-inflammatory cytokines.

Pro-Inflammatory Cytokines

Briefly, pro-inflammatory cytokines are cytokines that are important in cell signaling and promote systemic inflammation. They are produced predominantly by activated macrophages and are involved in the upregulation of inflammatory reactions. Pro-inflammatory cytokines arise from genes that code for the translation of small mediator molecules that induce a response after upregulation. Interleukin-1 (IL-1), IL6, IL-12, IL-18, IL-23, CD40L, tumor necrosis factor (TNF) such as TNF-α, gamma-interferon (IFN-gamma), granulocyte-macrophage colony stimulating factor, and MCP-1 are well characterized as pro-inflammatory cytokines. Inflammation is characterized by an interplay between pro- and anti-inflammatory cytokines.

Reducing the biological activities of pro-inflammatory cytokines can be useful for the treatment of some diseases. For instance, blocking IL-1 or TNF-α has been successful in helping patients with rheumatoid arthritis, inflammatory bowel disease, or graft-vs-host disease. See, Strober W, Fuss I J (May 2011). "Proinflammatory cytokines in the pathogenesis of inflammatory bowel diseases," Gastroenterology, Vol. 140 (6): 1756-67.

Anti-Inflammatory Cytokines

Briefly, anti-inflammatory cytokines are a series of immunoregulatory molecules that regulate the proinflammatory cytokine response. These molecules thus modulate and help to decrease inflammatory responses triggered by pro-inflammatory cytokines. Anti-inflammatory cytokines include, e.g., IL4, IL-10, IL-13, IFN-α, and transforming growth factor-beta (TGF-β) are recognized as anti-inflammatory cytokines.

In some embodiments of the methods taught herein, administration of the pharmaceutical composition comprising an SG protein or variant or fragment thereof is able to bring about reduced production of at least one pro-inflammatory cytokine (e.g., TNF-α and/or IL-23) by an immune cell in a patient administered the composition. In some embodiments, the administration is able to bring about an increase in the production of at least one anti-inflammatory cytokine (e.g., IL-10) by an immune cell in the patient. In some embodiments, the administration is able to bring about a decrease in the production of at least one anti-inflammatory cytokine (e.g., IL-10) by an immune cell in the patient. In some embodiments, the administration is able to bring about an improvement of mucin production in epithelial cells and/or epithelial wound healing in the patient.

The dosing regimen used for treatment depends upon the desired therapeutic effect, on the route of administration, and on the duration of the treatment. The dose will vary from patient to patient, depending upon the nature and severity of disease, the patient's weight, special diets then being followed by a patient, concurrent medication, and other factors which those skilled in the art will recognize.

Generally, dosage levels of a therapeutic (e.g., SG) protein between 0.0001 to 10 mg/kg of body weight daily are administered to the patient, e.g., patients suffering from inflammatory bowel disease. The dosage range will generally be about 0.5 mg to 100.0 g per patient per day, which may be administered in single or multiple doses.

In some aspects, the dosage range will be about 0.5 mg to 10 g per patient per day, or 0.5 mg to 9 g per patient per day, or 0.5 mg to 8 g per patient per day, or 0.5 mg to 7 g per patient per day, or 0.5 mg to 6 g per patient per day, or 0.5 mg to 5 g per patient per day, or 0.5 mg to 4 g per patient per day, or 0.5 mg to 3 g per patient per day, or 0.5 mg to 2 g per patient per day, or 0.5 mg to 1 g per patient per day.

In some aspects, the dosage range will be about 0.5 mg to 900 mg per patient per day, or 0.5 mg to 800 mg per patient per day, or 0.5 mg to 700 mg per patient per day, or 0.5 mg to 600 mg per patient per day, or 0.5 mg to 500 mg per patient per day, or 0.5 mg to 400 mg per patient per day, or 0.5 mg to 300 mg per patient per day, or 0.5 mg to 200 mg per patient per day, or 0.5 mg to 100 mg per patient per day, or 0.5 mg to 50 mg per patient per day, or 0.5 mg to 40 mg per patient per day, or 0.5 mg to 30 mg per patient per day, or 0.5 mg to 20 mg per patient per day, or 0.5 mg to 10 mg per patient per day, or 0.5 mg to 1 mg per patient per day.

Combination Therapies Comprising Therapeutic Proteins

The pharmaceutical compositions taught herein comprising an SG protein may be combined with other treatment therapies and/or pharmaceutical compositions. For example, a patient suffering from an inflammatory bowel disease, may already be taking a pharmaceutical prescribed by their doctor to treat the condition. In embodiments, the pharmaceutical compositions taught herein, are able to be administered in conjunction with the patient's existing medicines.

For example, the SG proteins taught herein may be combined with one or more of: an anti-diarrheal, a 5-aminosalicylic acid compound, an anti-inflammatory agent, an antibiotic, an antibody (e.g., antibodies targeting an inflammatory cytokine, e.g., antibodies targeting an anti-cytokine agent such as anti-TNF-α, (e.g., adalimumab, certolizumab pegol, golimumab, infliximab, V565) or anti-IL-12/IL-23 (e.g., ustekinumab, risankizumab, brazikumab, ustekinumab), a JAK inhibitor (e.g., tofacitinib, PF06700841, PF06651600, filgotinib, upadacitinib), an anti-integrin agent (e.g., vedolizumab, etrolizumab), a SIP inhibitor (e.g., etrasimod, ozanimod, amiselimod), a recombinant cell-based agent (e.g., Cx601), a steroid, a corticosteroid, an immunosuppressant (e.g., azathioprine and mercaptopurine), vitamins, and/or specialized diet.

Cancer patients undergoing chemotherapy or radiation therapy and suffering from or at risk of developing mucositis, e.g., oral mucositis, may be administered a pharmaceutical composition according to the present disclosure in combination with an agent used to treat mucositis such as oral mucositis. In some embodiments, a method of treatment comprises administering to a patient suffering from mucositis a combination of a pharmaceutical composition comprising an SG protein or a variant or fragment thereof and one or more second therapeutic agents selected from the group consisting of amifostine, benzocaine, benzydamine, ranitidine, omeprazole, capsaicin, glutamine, prostaglandin E2, Vitamin E, sucralfate, and allopurinol.

In some embodiments of the methods herein, the second therapeutic agent is administered in conjunction with an SG protein described herein, either simultaneously or sequentially. In some embodiments, the protein and the second agent act synergistically for treatment or prevention of the disease, or condition, or symptom. In other embodiments, the protein and the second agent act additively for treatment or prevention of the disease, or condition, or symptom.

Pharmaceutical Compositions Comprising a Therapeutic SG Protein

Pharmaceutical compositions are provided herein which comprise an SG protein, variant or fragment thereof according to the present disclosure or pharmaceutically acceptable salt thereof and a pharmaceutically acceptable excipient. In some embodiments, the pharmaceutical composition is formulated for administration to the gastrointestinal lumen, including the mouth, esophagus, small intestine, large intestine, rectum and/or anus.

In some embodiments, the composition comprises one or more other substances which are associated with the source of the SG protein, for example, cellular components from a host cell, or substance associated with chemical synthesis of the protein. In other embodiments, the pharmaceutical composition is formulated to include one or more second active agents as described herein. Moreover, the composition may comprise ingredients that preserve the structural and/or functional activity of the active agent(s) or of the composition itself. Such ingredients include but are not limited to antioxidants and various antibacterial and antifungal agents, including but not limited to parabens (e.g., methylparabens, propylparabens), chlorobutanol, phenol, sorbic acid, thimerosal or combinations thereof.

The terms "pharmaceutical" or pharmaceutically acceptable" refers compositions that do not or preferably do not produce an adverse, allergic, or other untoward reaction when administered to an animal, such as, for example, a human, as appropriate. The preparation of a pharmaceutical composition or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by the FDA Office of Biological Standards.

The pharmaceutical compositions of the disclosure are formulated according to the intended route of administration and whether it is to be administered, e.g., in solid, liquid or aerosol form. In a preferred embodiment, the composition can be administered rectally, but may also be administered topically, by injection, by infusion, orally, intrathecally, intranasally, subcutaneously, mucosally, localized perfusion bathing target cells directly, via a catheter, via a lavage, or by other method or any combination of the foregoing as would be known to one of ordinary skill in the art. Liquid formulations comprising a therapeutically effective amount of the SG protein can be administered rectally by enema, catheter, use of a bulb syringe. A suppository is an example of a solid dosage form formulated for rectal delivery. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and or about 1% to about 2%. Injectable liquid compositions are typically based upon injectable sterile saline or phosphate-buffered saline or other injectable carriers known in the art. Other liquid compositions include suspensions and emulsions. Solid compositions such as for oral administration may be in the form of tablets, pills, capsules (e.g., hard or soft-shelled gelatin capsules), buccal compositions, troches, elixirs, suspensions, syrups, wafers, or combinations thereof. The active agent in such liquid and solid compositions, i.e., a protein as described herein, is typically a component, being about 0.05% to 10% by weight, with the remainder being the injectable carrier and the like.

The pharmaceutical composition may be formulated as a controlled or sustained release composition which provide release of the active agent(s) including the therapeutic protein of the present disclosure over an extended period of time, e.g., over 30-60 minutes, or over 1-10 hours, 2-8 hours, 8-24 hours, etc. Alternatively or additionally, the composition is formulated for release to a specific site in the host body. For example, the composition may have an enteric coating to prevent release of the active agent(s) in an acidic environment such as the stomach, allowing release only in the more neutral or basic environment of the small intestine, colon or rectum. Alternatively or additionally, the composition may be formulated to provide delayed release in the mouth, small intestine or large intestine.

Each of the above-described formulations may contain at least one pharmaceutically acceptable excipient or carrier, depending up the intended route of administration, e.g., a solid for rectal administration or liquid for intravenous or parenteral administration or administration via cannula. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18$^{th}$ Ed. Mack Printing Company, 1990, pp. 1289-1329, incorporated herein by reference).

The pharmaceutical compositions for administration can be present in unit dosage forms to facilitate accurate dosing. Typical unit dosage forms include prefilled, premeasured ampules or syringes of the liquid compositions or suppositories, pills, tablets, capsules or the like in the case of solid compositions. In some embodiments of such compositions, the active agent, i.e., a protein as described herein, may be a component (about 0.1 to 50 wt/wt %, 1 to 40 wt/wt %, 0.1 to 1 wt/wt %, or 1 to 10 wt/wt %) with the remainder being various vehicles or carriers and processing aids helpful for forming the desired dosing form.

The actual dosage amount in a unit dosage form of the present disclosure administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Protein Expression Systems and Protein Production

Provided herein are compositions and methods for producing isolated SG proteins of the present disclosure as well as expression vectors which contain polynucleotide sequence encoding the SG proteins and host cells which harbor the expression vectors.

The SG proteins of the present disclosure can be prepared by routine recombinant methods, e.g., culturing cells transformed or transfected with an expression vector containing a nucleic acid encoding a therapeutic SG protein, variant or fragment thereof. Host cells comprising any such vector are also provided. Host cells can be prokaryotic or eukaryotic and examples of host cells include E. coli, yeast, or mammalian cells. A method for producing any of the herein described proteins is further provided and comprises culturing host cells under conditions suitable for expression of the desired protein and recovering the desired protein from the cell culture. The recovered protein can then be isolated and/or purified for use in in vitro and in vivo methods, as well as for formulation into a pharmaceutically acceptable composition. In some embodiments, the SG protein is expressed in a prokaryotic cell such as E. coli and the isolation and purification of the protein includes step to reduce endotoxin to levels acceptable for therapeutic use in humans or other animals.

Expression Vectors

Provided herein are expression vectors which comprise a polynucleotide sequence which encodes an SG protein of the present disclosure or a variant and/or fragment thereof. Polynucleotide sequences encoding the SG proteins of the disclosure can be obtained using standard recombinant techniques. Desired encoding polynucleotide sequences may be amplified from the genomic DNA of the source bacterium, i.e., E. eligens and or C. bartlettii. Alternatively, polynucleotides can be synthesized using nucleotide synthesizer. Once obtained, sequences encoding the polypeptides are inserted into a recombinant vector capable of replicating and expressing heterologous (exogenous) polynucleotides in a host cell. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using a pBR322, pUC, pET or pGEX vector, a plasmid derived from an E. coli species. Such vectors contain genes encoding ampicillin (Amp) and tetracycline (Tet) resistance and thus provides easy means for identifying transformed cells. These vectors as well as their derivatives or other microbial plasmids or bacteriophage may also contain, or be modified to contain, promoters which can be used by the microbial organism for expression of endogenous proteins.

An expression vector of the present disclosure may comprise a promoter, an untranslated regulatory sequence located upstream (5') and operably linked to a protein-encoding nucleotide sequence such that the promoter regulated transcription of that coding sequence. Prokaryotic promoters typically fall into two classes, inducible and constitutive. An inducible promoter is a promoter that initiates increased levels of transcription of the encoding polynucleotide under its control in response to changes in the culture condition, e.g., the presence or absence of a nutrient or a change in temperature. A large number of promoters recognized by a variety of potential host cells are well known and a skilled artisan can choose the promoter according to desired expression levels. Promoters suitable for use with prokaryotic hosts include E. coli promoters such as lac, trp, tac, trc and ara, viral promoters recognized by E. coli such as lambda and T5 promoters, and the T7 and T7lac promoters derived from T7 bacteriophage. A host cell harboring a vector comprising a T7 promoter, e.g., is engineered to express a T7 polymerase. Such host cells include E. coli BL21(DE3), Lemo21(DE3), and NiCo21(DE3) cells. In some embodiments, the promoter is an inducible promoter which is under the control of chemical or environmental factors.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Suitable vectors for expression in both prokaryotic and eukaryotic host cells are known in the art and some are further described herein.

Vectors of the present disclosure may further comprise a signal sequence which allows the translated recombinant protein to be recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. Well-known signal sequences for use in eukaryotic expression systems include but are not limited to interleukin-2, CD5, the Immunoglobulin Kappa light chain, trypsinogen, serum albumin, and prolactin.

SG proteins or variants or fragments thereof as described herein can be expressed as a fusion protein or polypeptide. Commonly used fusion partners include but are not limited to human serum albumin and the crystallizable fragment, or constant domain of IgG, Fc. The histidine tag or FLAG tag can also be used to simplify purification of recombinant protein from the expression media or recombinant cell lysate. The fusion partners can be fused to the N- and/or C-terminus of the protein of interest.

Host Cells

Suitable host cells for cloning or expressing the DNA in the vectors herein include prokaryote, yeast, or higher eukaryote cells. Numerous cell lines and cultures are available for use as a host cell, and they can be obtained for example through the American Type Culture Collection (ATCC), which is an organization that serves as an archive for living cultures and genetic materials. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* species, as well as a number of commercially available bacterial hosts such as SURE® Competent Cells and SOLOPACK™ Gold Cells (STRATAGENE®, La Jolla). In certain embodiments, bacterial cells such as *E. coli* are particularly contemplated as host cells.

Examples of eukaryotic host cells for replication and/or expression of a vector include, but are not limited to, HeLa, NIH3T3, Jurkat, 293, Cos, CHO, Saos, and PC12. Additional eukaryotic host cells include yeasts (e.g., *Pichia pastoris* and *Saccharomyces cerevisiae*) and cells derived from insects (e.g., *Spodoptera frugiperda* or *Trichoplusia ni*). Many host cells from various cell types and organisms are available and would be known to one of skill in the art. Similarly, a viral vector may be used in conjunction with either a eukaryotic or prokaryotic host cell, particularly one that is permissive for replication or expression of the vector. The selection of the appropriate host cell is deemed to be within the skill in the art.

Methods are well known for introducing recombinant DNA, i.e., an expression vector, into a host cell so that the DNA is replicable, either as an extrachromosomal element or as a chromosomal integrant, thereby generating a host cell which harbors the expression vector of interest. Methods of transfection are known to the ordinarily skilled artisan, for example, by $CaPO_4$ and electroporation. Depending on the host cell used, transformation is performed using standard techniques appropriate to such cells. The calcium treatment employing calcium chloride, as described in Sambrook et al. (1989, Cold Spring Harbor Laboratory Press) or electroporation is generally used for prokaryotes or other cells that contain substantial cell-wall barriers. General aspects of mammalian cell host system transformations have been described in U.S. Pat. No. 4,399,216. Transformations into yeast are typically carried out according to the method of Van Solingen et al., J. Bact, 130:946 (1977) and Hsiao et al., Proc. Natl. Acad. Sci. (USA), 76:3829 (1979). Other methods for introducing DNA into cells include nuclear microinjection, electroporation, bacterial protoplast fusion with intact cells, or introduction using polycations, e.g., polybrene, polyomithine. For various techniques for transforming mammalian cells, see Keown et al., Methods in Enzymology. 185:527-537 (1990) and Mansour et al., Nature, 336:348-352 (1988).

Accordingly, provided herein is a recombinant vector or expression vector as described above and comprising a polynucleotide which encodes an SG therapeutic protein sequence of interest (e.g., SEQ ID NO:2 (SG-15), SEQ ID NO:10 (SG-16), SEQ ID NO:14 (SG-17) or SEQ ID NO:20 (SG-18), or variant and/or fragment thereof as described herein). The polynucleotide can be, for example, any one of SEQ ID NO:2, SEQ ID NO:10, SEQ ID NO:14 or SEQ ID NO:20, or a variant or a fragment thereof. Moreover, the present disclosure teaches a host cell harboring the vector. The host cell can be a eukaryotic or prokaryotic cell as detailed above. In a preferred embodiment, the host cell is a prokaryotic cell. In a further preferred embodiment, the host cell is *E. coli*. The recombinant expression vector may be constructed to express an SG protein with, e.g, an affinity tag at the N-terminus and/or the C-terminus. The affinity tag can be linked to the SG protein via a short amino acid sequence which contains a protease cleavage site. Accordingly, after cleavage of the expressed protein with the protease, the SG protein may contain exogenous amino acids at the N- or C-terminus of the therapeutic protein without affecting functional activity of the protein.

In some embodiments, the polynucleotide encoding the protein of interest is codon-optimized. A codon optimization algorithm is applied to a polynucleotide sequence encoding a protein in order to choose an appropriate codon for a given amino acid based on the expression host's codon usage bias. Many codon optimization algorithms also take into account other factors such as mRNA structure, host GC content, ribosomal entry sites. Some examples of codon optimization algorithms and gene synthesis service providers are: AU™: www.atum.bio/services/genegps; GenScript: www.genscript.com/codon-opt.html; ThermoFisher: www.thermofisher.com/us/en/home/life-science/cloning/gene-synthesis/geneart-gene-synthesis/geneoptimizer.html; and Integrated DNA Technologies: www.idtdna.com/CodonOpt. The nucleotide sequence is then synthesized and cloned into an appropriate expression vector.

Methods to Produce the Protein

Methods are provided for producing the proteins described herein but are well known to the ordinarily skilled artisan. Host cells transformed or transfected with expression or cloning vectors described herein for protein production are cultured in conventional nutrient media modified as appropriate for inducing promoters, selecting and/or maintaining transformants, and/or expressing the genes encoding the desired protein sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991) and Molecular Cloning: A Laboratory Manual (Sambrook, et al., supra).

Generally, "purified" will refer to a specific protein composition that has been subjected to fractionation to remove non-proteinaceous components and various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present disclosure, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Another contemplated is the purification of a specific fusion protein using a specific binding partner. Such purification methods are routine in the art. As the present disclosure provides DNA sequences for the specific proteins, any fusion protein purification method can now be practiced. This is exemplified by the generation of a specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

Recombinantly expressed SG proteins of the present disclosure can be recovered from culture medium or from host cell lysates. The suitable purification procedures include, for example, by fractionation on an ion-exchange (anion or cation) column; ethanol precipitation; reverse phase HPLC; chromatography on silica or on a cation-exchange resin such as DEAE; chromatofocusing; SDS-PAGE; ammonium sulfate precipitation; gel filtration or size exclusion chromatograph (SEC) using, for example, Sephadex G-75; and metal chelating columns to bind epitope-tagged forms of a polypeptide of the present disclosure. Various methods of protein purification can be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular polypeptide produced.

Alternative methods, which are well known in the art, can be employed to prepare an SG protein of the present disclosure. For example, a sequence encoding a protein or portion thereof, can be produced by direct peptide synthesis using solid-phase techniques (see, e.g., Stewart et al., 1969, Solid-Phase Peptide Synthesis, W.H. Freeman Co., San Francisco, Calif; Merrifield. J. 1963, Am. Chem. Soc., 85:2149-2154. Automated synthesis can be accomplished, for instance, using an Applied Biosystems Peptide Synthesizer (Foster City, Calif.) using manufacturer's instructions.

In some embodiments, the disclosure provides chimeric molecules comprising any of the herein described polypeptides fused to a heterologous polypeptide or amino acid sequence and the polynucleotides encoding the chimeric molecules. Examples of such chimeric molecules include, but are not limited to, any of the herein described polypeptides fused to an epitope tag sequence, an Fc region of an immunoglobulin.

Recombinant Bacterial Delivery Systems

The present disclosure contemplates utilizing delivery systems outside of the traditional pharmaceutical formulations that comprise a purified protein. In some embodiments, the disclosure utilizes recombinant bacterial delivery systems, phage-mediated delivery systems, chitosan-DNA complexes, or AAV delivery systems.

One particular recombinant bacterial delivery system is based upon *Lactococcus lactis*. Essentially, one may clone the gene encoding the therapeutic protein (e.g. SEQ ID NO:1, SEQ ID NO:9, SEQ ID NO:13 or SEQ ID NO: 19) into an expression vector, and then transform the vector into *L. lactis*. Subsequently, one may then administer the *L. lactis* to a patient. See, e.g. Bratt, et al., "A phase 1 trial with transgenic bacteria expressing interleukin-10 in Crohn's disease," Clinical Gastroenterology and Hepatology, 2006, Vol. 4, pgs. 754-759 ("We treated Crohn's disease patients with genetically modified *Lactococcus lactis* (LL-Thy12) in which the thymidylate synthase gene was replaced with a synthetic sequence encoding mature human interleukin-10."); Shigemori, et al., "Oral delivery of *Lactococcus lactis* that secretes bioactive heme oxygenase-1 alleviates development of acute colitis in mice," Microbial Cell Factories, 2015, Vol. 14:189 ("Mucosal delivery of therapeutic proteins using genetically modified strains of lactic acid bacteria (gmLAB) is being investigated as a new therapeutic strategy."); Steidler, et al., "Treatment of murine colitis by *Lactococcus lactis* secreting interleukin-10," Science, 2000, Vol. 289, pgs. 1352-1355 ("The cytokine interleukin-10 (IL-10) has shown promise in clinical trials for treatment of inflammatory bowel disease (IBD). Using two mouse models, we show that the therapeutic dose of IL-10 can be reduced by localized delivery of a bacterium genetically engineered to secrete the cytokine. Intragastric administration of IL-IOÐsecreting *Lactococcus lactis* caused a 50% reduction in colitis in mice treated with dextran sulfate sodium and prevented the onset of colitis in IL-102/2 mice. This approach may lead to better methods for cost effective and long-term management of IBD in humans."); Hanniffy, et al., "Mucosal delivery of a pneumococcal vaccine using *Lactococcus lactis* affords protection against respiratory infection," Journal of Infectious Diseases, 2007, Vol. 195, pgs. 185-193 ("Here, we evaluated *Lactococcus lactis* intracellularly producing the pneumococcal surface protein A (PspA) as a mucosal vaccine in conferring protection against pneumococcal disease."); and Vandenbroucke, et al., "Active delivery of trefoil factors by genetically modified *Lactococcus lactis* prevents and heals acute colitis in mice," Gastroenterology, 2004, Vol. 127, pgs. 502-513 ("We have positively evaluated a new therapeutic approach for acute and chronic colitis that involves in situ secretion of murine TFF by orally administered *L. lactis*. This novel approach may lead to effective management of acute and chronic colitis and epithelial damage in humans.").

In another embodiment, a "synthetic bacterium" may be used to deliver an SG protein or variant or fragment thereof wherein a probiotic bacterium is engineered to express the therapeutic SG protein (see, e.g., Durrer and Allen, 2017, PLoS One, 12:e0176286).

Phages have been genetically engineered to deliver specific DNA payloads or to alter host specificity. Transfer methods, such as phages, plasmids, and transposons, can be used to deliver and circulate engineered DNA sequences to microbial communities, via processes such as transduction, transformation, and conjugation. For purposes of the present disclosure, it is sufficient to understand that an engineered phage could be one possible delivery system for a protein of the disclosure, by incorporating the nucleic acid encoding said protein into the phage and utilizing the phage to deliver the nucleic acid to a host microbe that would then produce the protein after having the phage deliver the nucleic acid into its genome.

Similar to the aforementioned engineered phage approach, one could utilize a transposon delivery system to incorporate nucleic acids encoding a therapeutic protein into a host microbe that is resident in a patient's microbiome. See, Sheth, et al., "Manipulating bacterial communities by in situ microbiome engineering," Trends in Genetics, 2016, Vol. 32, Issue 4, pgs. 189-200.

The following examples are intended to illustrate, but not limit, the disclosure.

EXAMPLES

The following experiments utilize a robust mixture of in vitro experiments combined with in vivo models of IBD to demonstrate the therapeutic ability of the taught proteins and methods. Specifically, Examples 1 to 4 below demonstrate the functional utility of the therapeutic SG proteins to treat a gastrointestinal inflammatory disease, or disease involving impaired epithelial barrier integrity/function. Each of Examples 1 to 4 describes in vitro and in vivo experiments to assess functional activity of proteins SG-15, SG-16, SG-17 and SG-18, respectively.

Example 1. SG-15

A. Expression of SG-15

For experiments described in the examples below, a polynucleotide comprising a sequence encoding residues 1-400 of SEQ ID NO:1 (SG-15) was obtained by PCR amplification of genomic DNA obtained from *Eubacterium eligens* (C15-B4; DSM 3376 type strain; See, e.g., Holdeman, L. V., Moore, W. E. C. (1974) New genus, *Coprococcus*, twelve new species, and amended descriptions of four previously described species of bacteria from human feces. Int J Syst Bacteriol 24, 260-277. The encoding polynucleotide was then subcloned into an inducible expression vector and used to transform *E. coli* BL21(DE3) cells for expression and purification of SG-15 as detailed below, using culturing and purification methods which are routine in the art.

Expression and purification of proteins for use in various experiments pertaining to the present disclosure and for the following examples is described here. Expression was achieved using a pGEX vector system which is designed for inducible, high-level intracellular expression of genes or gene fragments. Expression in *E. coli* yields tagged proteins with the GST moiety at the amino terminus and the protein of interest at the carboxyl terminus. The vector has a tac promoter for chemically inducible, high-level expression and an internal laq1$^q$ gene for use in any *E. coli* host.

The polynucleotide comprising a nucleotide sequence (PCR-amplified from *E. eligens* DSM 3376 and encoding residues 1 to 400 of SEQ ID NO:1) was inserted into the BamHI and NotI sties of the multiple-cloning site of a pGEX-6P-1 vector (GE Healthcare Life Science, Pittsburgh, PA) to express SG-15 as a GST fusion protein which was then cleaved at the Precision protease site, whereby an exogenous GPLG sequence is present at the N-terminus and AAS is present at the C-terminus of the cleaved and purified protein. BL21(DE) *E. coli* cells were transformed with the expression construct. BL21(DE3) transformants were grown in 10 L LB with 50 µg/ml carbenicillin at 37° C. When cultures reached a density of 0.8 $OD_{600}$, they were chilled to 16° C. and expression was induced with 1 mM IPTG at 16° C. for 16 h. Cells were harvested and lysed by sonication, and a soluble lysate was applied to a GSTrap column. Bound protein was washed with HEPES buffer and then purified tag-free SG-15 was eluted by adding HRV3C protease to cleave the protein C-terminal to the GST-tag. Eluted fractions containing protein as determined by SDS-PAGE and Coomasie Brilliant Blue staining were identified and pooled, then applied to a HiTrap Q HP anion exchange column then to a HiLoad Superdex 200 26/60 preparative size exclusion column (SEC) to obtain a final preparation.

In an alternative method of expression and purification with the same expression construct, BL21 transformants were grown in LB and 100 µg/ml carbenicillin and 1 µg/ml chloramphenicol at 30° C. Expression was induced when a culture density of 0.6 $OD_{600}$ was reached, with 0.4 mM IPTG for 4 h. Cells were harvested by centrifugation then lysed by sonication, and a soluble lysate was applied to a GST-resin column. Bound protein was washed with PBS and then purified tag-free SG-15 was eluted by adding PreScission Protease to cleave the protein C-terminal to the GST-tag.

Purified proteins were quantified by densitometry using bovine serum albumin as a reference following SDS-PAGE and Coomassie Brilliant Blue staining. Endotoxin levels were measured with Endosafe® nexgen-MCSrm (Charles River, Wilmington, MA) according to the manufacturer's instructions. Endotoxin levels of proteins used for the assays described herein were lower than 1 EU/mg.

B. Effect of SG-15 on Restoration of Epithelial Barrier Integrity Following Inflammation Induced Disruption The following experiment assesses the effects of an SG-15 protein as disclosed herein to restore gastrointestinal epithelial barrier integrity in vitro.

Assays were performed as described below in trans-well plates where co-cultures of multiple cell types were performed utilizing a permeable membrane to separate cells. In the apical (top) chamber, human colonic epithelial cells, consisting of a mixture of enterocytes and goblet cells, were cultured until cells obtained tight junction formation and barrier function capacity as assessed by measurement of trans-epithelial electrical resistance (TEER). In the basolateral chamber, monocytes were cultured separately. Epithelial cells were primed with inflammatory cytokines. The assays measured the effect of a therapeutic protein, i.e., SG-15, on epithelial barrier function, wound healing, and production of cytokines.

Cell culture. The HCT8 human enterocyte cell line (ATCC Cat. No. CCL-244) was maintained in RPMI-1640 medium supplemented with 10% fetal bovine serum, 100 IU/ml penicillin, 100 µg/ml streptomycin, 10 µg/ml gentamicin and 0.25 µg/ml amphotericin (cRPMI). HT29-MTX human goblet cells (Sigma-Aldrich (St. Louis, MO; Cat. No. 12040401) were maintained in DMEM medium with 10% fetal bovine serum, 100 IU/ml penicillin, 100 µg/ml streptomycin, 10 µg/ml gentamicin and 0.25 µg/ml amphotericin (cDMEM). Epithelial cells were passaged by trypsinization and were used between 5 and 15 passages following thawing from liquid nitrogen stocks. U937 monocytes (ATCC Cat. No. 700928) were maintained in cRPMI medium as a suspension culture, and split by dilution as needed to maintain cells between $5 \times 10^5$ and $2 \times 10^6$ cells/ml. U937 cells were used up to passage 18 following thawing from liquid nitrogen stocks.

Epithelial cell culture. A mixture of HCT8 enterocytes and HT29-MTX goblet cells were plated at a 9:1 ratio, respectively, in the apical chamber of the transwell plate as described previously (Berget et al., 2017, Int J Mol Sci, 18:1573; Beduneau et al., 2014, Eur J Pharm Biopharm, 87:290-298). A total of $10^5$ cells were plated in each well ($9 \times 10^4$ HCT8 cells and $1 \times 10^4$ HT29-MTX cells per well). Epithelial cells were trypsinized from culture flasks and viable cells determined by trypan blue counting. The correct volumes of each cell type were combined in a single tube and centrifuged. The cell pellet was resuspended in cRPMI and added to the apical chamber of the transwell plate. Cells were cultured for 8 to 10 days at 37° C.+5% $CO_2$, and media was changed every 2 days.

Monocyte culture. On day 6 of epithelial cell culture $2 \times 10^5$ cells/well U937 monocytes were plated into a 96 well receiver plate. Cells were cultured at 37° C.+5% $CO_2$ and media was changed every 24 hours for four days.

Co-culture assay. Following 8-10 days of culture the transwell plate containing enterocytes were treated with 10 ng/ml IFN-γ added to the basolateral chamber of the transwell plate for 24 hours at 37° C.+5% $CO_2$. After 24 hours fresh cRPMI was added to the epithelial cell culture plate. Trans-epithelial electrical resistance (TEER) readings were measured after the IFN-γ treatment and were used as the pre-treatment TEER values. SG-15 was then added to the apical chamber of the transwell plate at a final concentration of 1 μg/ml (40 nM). The myosin light chain kinase (MLCK) inhibitor peptide 18 (BioTechne, Minneapolis, MN) was used at 50 nM as a positive control to prevent inflammation induced barrier disruption (Zolotarevskky et al., 202, Gastroenterology, 123:163-172). The bacterially derived molecule staurosporine was used at 100 nM as a negative control to induce apoptosis and exacerbate barrier disruption (Antonsson and Persson, 2009, Anticancer Res, 29:2893-2898). Compounds were incubated on enterocytes for 1 hour or 6 hours. Following pre-incubation with test compounds the transwell insert containing the enterocytes was transferred on top of the receiver plate containing U937 monocytes. Heat killed E. coli (HK E. coli) (bacteria heated to 80° C. for 40 minutes) was then added to both the apical and basolateral chambers and a multiplicity of infection (MOI) of 10. Transwell plates were incubated at 37° C.+5% $CO_2$ for 24 hours and a post treatment TEER measurement was made. The TEER assays were performed with recombinantly expressed mature (lacking a signal peptide) SG-15 protein such as that described in Example 1A above.

Data analysis. Raw electrical resistance values in ohms (Ω) were converted to ohms per square centimeter ($\Omega cm^2$) based on the surface area of the transwell insert (0.143 $cm^2$). To adjust for differential resistances developing over 10 days of culture, individual well post treatment $\Omega cm^2$ readings were normalized to pre-treatment $\Omega cm^2$ readings. Normalized 2 $cm^2$ values were then expressed as a percent change from the mean $\Omega cm^2$ values of untreated samples.

Figure 1B:
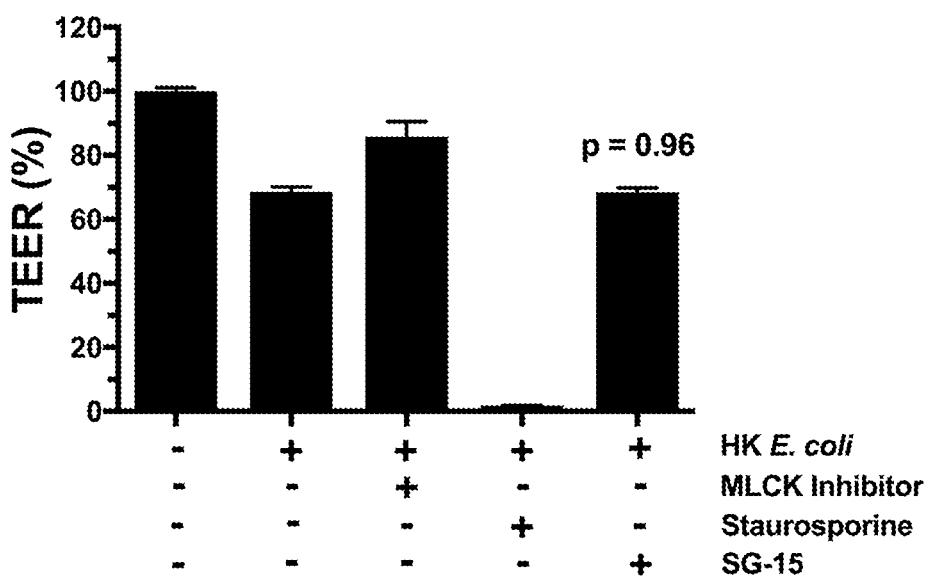

SG-15 protein was added 30 minutes (FIG. 1A) or 6 hours (FIG. 1B) prior to exposure of both epithelial cells and monocytes to heat killed Escherichia coli (HK E. coli), inducing monocytes to produce inflammatory mediators resulting in disruption of the epithelial monolayer as indicated by a reduction in TEER. A myosin light chain kinase (MLCK) inhibitor was utilized as a control compound, which has been shown to prevent barrier disruption and/or reverse barrier loss triggered by the antibacterial immune response. Staurosporine was used as a control compound that caused epithelial cell apoptosis and/or death, thus resulting in a drastic decrease in TEER, which indicates disruption and/or loss of epithelial cell barrier integrity/function. In FIG. 1A, TEER of epithelial cell barrier increased slightly from 69.6% only when epithelial cells were exposed to heat killed E. coli to 71.4% when incubating epithelial cells with SG-15 for 30 minutes before exposing to HK E. coli (p=0.69). In FIG. 1B, epithelial cells pre-incubated with SG-15 for 6 hours before HK E. coli exposure maintained 68.5% in TEER and a 68.6% without SG-15 treatment (p=0.96). The graphs in FIGS. 1A-1B represent data pooled from two individual experiments (n=6).

C. Effect of SG-15 on TNF-α, IL-23, and IL-10 Production by Heat Killed Escherichia coli The following experiment demonstrates the therapeutic ability of an SG-15 protein as disclosed herein to reduce immune activation as measured by cytokine production. The experiment thereby demonstrates potential functional utility of a therapeutic SG protein to treat a gastrointestinal inflammatory disease, or disease involving impaired epithelial barrier integrity/function, where modulation of cytokine levels would affect the disease state in a host.

Production of the cytokines TNF-α, IL-23, and IL-10 by monocytes was measured in the tissue culture supernatant from the basolateral chamber of the co-culture TEER assay performed in Example 1B. Following TEER readings, the supernatants were centrifuged at 10,000 g for 5 minutes at 4° C. to remove cell debris. Luminex analysis was performed according to the manufacturer's instructions (Magpix instrument and xPonent software version 4.2; Luminex Corporation (Austin, TX)). Luminex analysis was performed to determine the μg/ml concentration of TNF-α and IL-23 produced by monocytes. Luminex analysis utilizes a bead-based system for quantification of multiple cytokines from a single sample. Like an ELISA, Luminex beads are coated with a capture antibody, and incubation with samples allows the target to bind to the capture antibody. Beads are washed and incubated with a fluorescently labeled detection antibody for quantification of bound target. Cytometric analysis is used to differentiate bead populations, which are loaded with differential fluorescent dyes, and to quantify cytokine levels by measuring detection antibody signal.

Figure 2A:
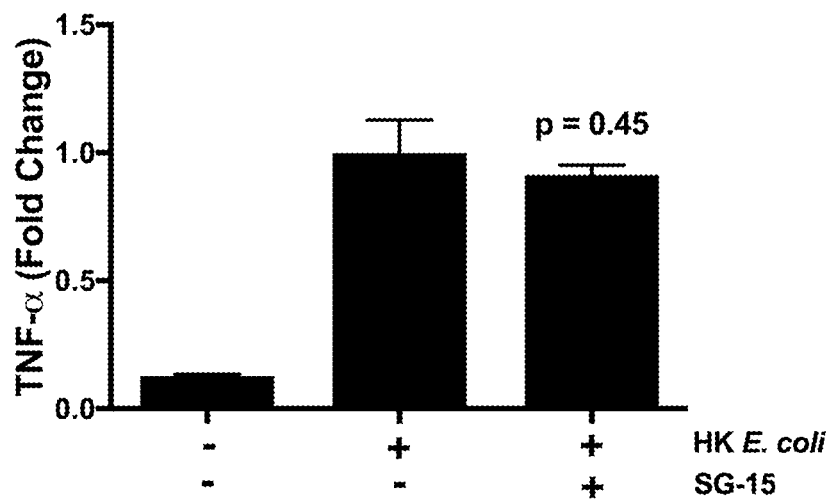
FIG. 2A shows effects of SG-15 administration on TNF-α production induced by heat killed *Escherichia coli* (HK *E. coli*), as described in Example 1C.
Figure 2B:
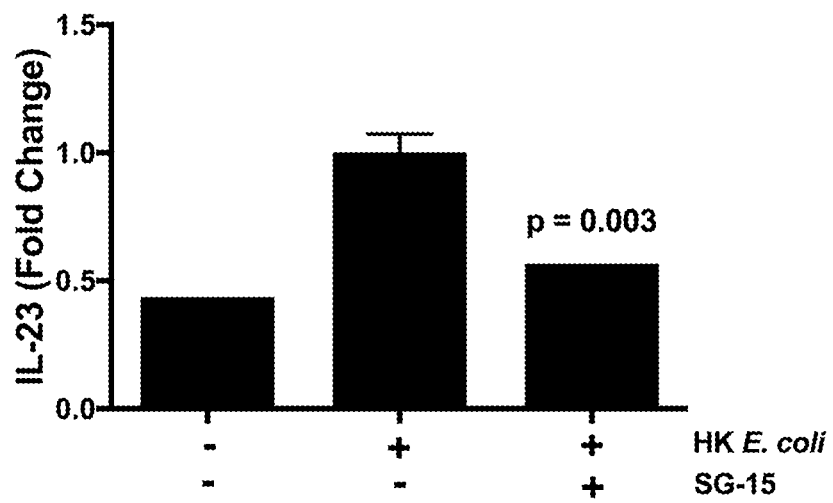
FIG. 2B shows effects of SG-15 administration on IL-23 production induced by HK *E. coli*, as described in Example 1C.
Figure 2C:
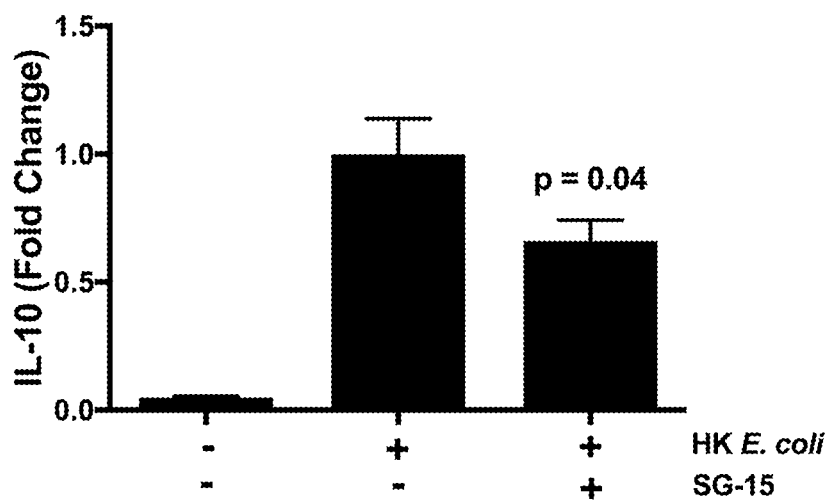
FIG. 2C shows effects of SG-15 administration on IL-10 production induced by HK *E. coli*, as described in Example 1C.

TNF-α, IL-23, and IL-10 production in untreated cells and cells pre-incubated with SG-15 for 6 hours prior to HK E. coli treatment was normalized to pg/ml concentrations elicited by HK E. coli only, which was set to 1.0. Pre-incubation with SG-15 significantly reduced TNF-α production to 0.91. Results are shown in FIG. 2A. Pre-incubation with SG-15 significantly reduced IL-23 production to 0.57. There was no significant difference between IL-23 production by control cells treated with media only, and cells treated with SG-15 and HK E. coli. Results are shown in FIG. 2B. Pre-incubation with SG-15 significantly reduced IL-10 production to 0.66. Results are shown in FIG. 2C. The graphs in FIGS. 2A, 2B and 2C each represent data pooled from an individual experiment (n=3).

D. Effects of SG-15 on Epithelial Cell Wound Healing

The following experiment demonstrates the therapeutic ability of an SG-15 protein as disclosed herein to increase gastrointestinal epithelial cell wound healing. The experiment is therefore a demonstration of the functional utility of a therapeutic SG-15 protein to treat a gastrointestinal inflammatory disease, or disease involving impaired epithelial barrier integrity/function, where increased epithelial cell wound healing would be beneficial.

HCT8 enterocytes and HT29-MTX goblet cells were used in wound healing studies. The 96 well Oris Cell Migration assay containing plugs preventing cell attachment in the center of each well was used according to the manufacturer's instructions (Platypus Technologies, Madison, WI).

The migration assay plates were warmed to room temperature prior to use and plugs were removed from 100% confluence wells prior to cell addition. The HCT8 enterocyte and HT29-MTX goblet cell lines were used at a 9:1 ratio with a total of $5 \times 10^4$ total cells added per well ($4.5 \times 10^4$ HCT8 cells and $0.5 \times 10^4$ HT29-MTX cells). Cells were incubated at 37° C.+5% $CO_2$ for 24 hours. Plugs were then removed from all control and sample wells. Control wells included cells treated with the diluent vehicle as the blank, 30 ng/ml epidermal growth factor (EGF) as the positive control, and 100 nM staurosporine as the negative control, all diluted in cRPMI. Sample wells contained SG-15 protein at a concentration of 1 μg/ml diluted in cRPMI. 100% and 0% wells were cultured in cRPMI. Treatments were added to cells and incubated at 37° C.+5% $CO_2$ for 48 hours. Prior to staining for viable cells, plugs were removed from the 0% wells. Treatment media was removed and cells were washed in PBS containing 0.9 mM $CaCl_2$) and 0.5 mM $MgCl_2$. The green fluorescent viability dye Calcenin AM was added to all wells at a concentration of 0.5 µg/ml in PBS containing 0.9 mM $CaCl_2$) and 0.5 mM $MgCl_2$, incubated for 30 min at 37° C.+5% $CO_2$, the dye was removed and cells were washed in PBS containing 0.9 mM $CaCl_2$) and 0.5 mM $MgCl_2$ and fluorescence was measured. Relative fluorescent values from 100% wells where plugs were removed prior to cell plating were set as the max effect, and 0% wells where plugs remained in place until immediately before staining were used as the baseline. Samples were normalized between 100% and 0% samples and values expressed as a percent growth.

Figure 3:
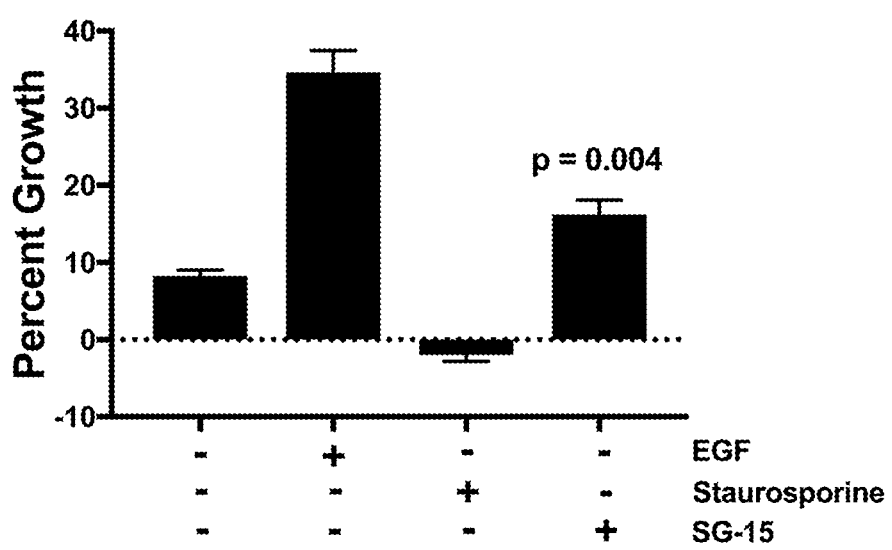
FIG. 3 shows effects of SG-15 administration on epithelial cell wound healing, as described in Example 1D.

As shown in FIG. 3, a significant increase in growth was observed with SG-15. In addition, control compounds modulated wound healing as expected with EGF increasing proliferation, and staurosporine suppressing cell proliferation. The graph in FIG. 3 represents data pooled from 4 replicate experiments (n=18).

E. SG-15 Demonstrates Therapeutic Activity in a DSS Model of Inflammatory Bowel Disease Example 1E demonstrates activity of an SG-15 protein as disclosed herein for the treatment of inflammatory bowel disease in an in vivo model. Specifically, the mice in Example 1E were treated with dextran sodium sulfate (DSS), a chemical known to induce intestinal epithelial damage and thereby reduce intestinal barrier integrity and function. DSS mice are well-accepted models of colitis. In Example 1E, mice were treated with SG-15 protein approximately concurrent with (6 hours prior to) administration of DSS. The mice were then assessed for effects of SG-15 on clinically relevant markers of improved health.

The graphs presented in Example 1E represent data pooled from 2 individual experiments, each using 10 mice (n=20). The SG-15 protein used in these experiments was the mature protein (no signal peptide), expressed as described in Example 1A above.

Eight-week old C57BL/6 mice were housed 5 animals were cage and given food and water ad libitum for 7 days. Following the 7-day acclimation period, treatments were initiated concurrently with addition of 2.5% DSS to the drinking water. Preliminary tracking studies with fluorescently labeled bovine serum albumin following intraperitoneal (i.p.) injection of protein demonstrated proteins reached the colon at 6 hours after i.p. delivery. Based on these results, 6 hr prior to addition of 2.5% DSS to the drinking water mice were treated with 50 nmoles/kg SG-15 i.p. or 0.2 mg/kg Gly2-GLP2 i.p. Six hours after the initial treatment the drinking water was changed to water containing 2.5% DSS. The mice were treated with 2.5% dextran sodium sulfate (DSS) in their drinking water for 6 days. Treatments were continued with SG-15 or Gly2-GLP2 twice a day (b.i.d.) in the morning and evening (every 8 and 16 hr) with i.p. injections at 50 nmoles/kg. Fresh 2.5% DSS drinking water was prepared every 2 days.

Figure 4:
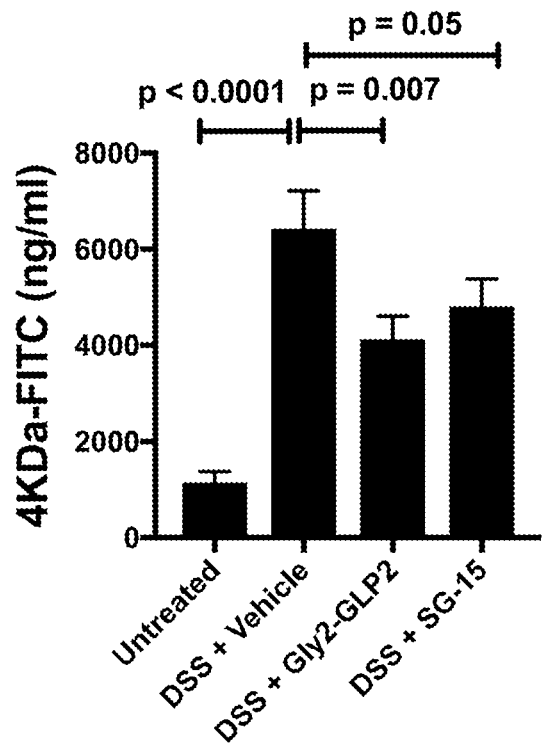
FIG. 4 shows effects of SG-15 administration on epithelial centric barrier function readouts in a DSS model of inflammatory bowel disease, as described in Example 1E.

On day six, mice were fasted for four hours and then orally gavaged with 600 mg/kg 4 KDa dextran labeled with fluorescein isothiocyanate (FITC) [4KDa-FITC]. One hour after the 4KDa-FITC gavage mice were euthanized, blood was collected and FITC signal was measured in serum. A significant increase in 4KDa-FITC dextran translocation across the epithelial barrier was observed in vehicle treated DSS mice in comparison to untreated mice. Additionally, a significant reduction in 4KDa-FITC dextran was observed in mice receiving DSS and treated with SG-15, as compared to DSS mice treated with vehicle. Results are shown in FIG. 4, and are presented as mean±SEM. The graph in FIG. 4 represents data pooled from 2 individual experiments (n=20).

Figure 5:
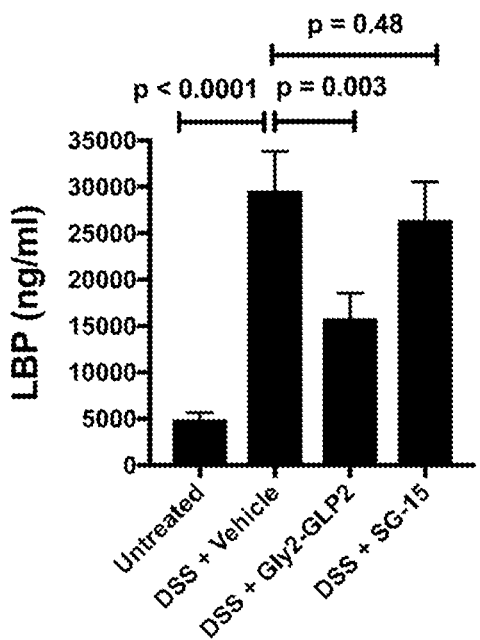
FIG. 5 shows effects of SG-15 administration on inflammatory readouts responsive to impaired barrier function in a DSS model of inflammatory bowel disease, as described in Example 1F.

F. Effects of SG-15 on Inflammation Readouts Responsive to Impaired Barrier Function in a Concurrent DSS Model of Inflammatory Bowel Disease SG-15 was also assessed for its effects on the levels of LPS binding protein (LBP) in the blood of the DSS animal with and without SG-15 administration. LPS binding protein (LBP), which has been linked to clinical disease activity in subjects with inflammatory bowel disease, was also measured by ELISA in the serum of mice tested in the DSS model described in Example 1E. A significant increase in LBP concentration was observed in vehicle-treated DSS mice, as compared to untreated mice. Additionally, a significant reduction in LBP was observed in SG-15 treated mice given DSS as compared to DSS mice treated with vehicle. Results are shown in FIG. 5, and are presented as mean±SEM. The graph in FIG. 5 represents data pooled from the 2 individual experiments (n=20).

G. Effects of SG-15 on Weight Loss in a Concurrent DSS Model of Inflammatory Bowel Disease Also assessed was the therapeutic ability of an SG-15 protein as disclosed herein to ameliorate weight loss in an animal suffering from an inflammatory intestinal disorder. Weight loss is a significant and potentially dangerous side effect of inflammatory bowel disease.

Figure 6:
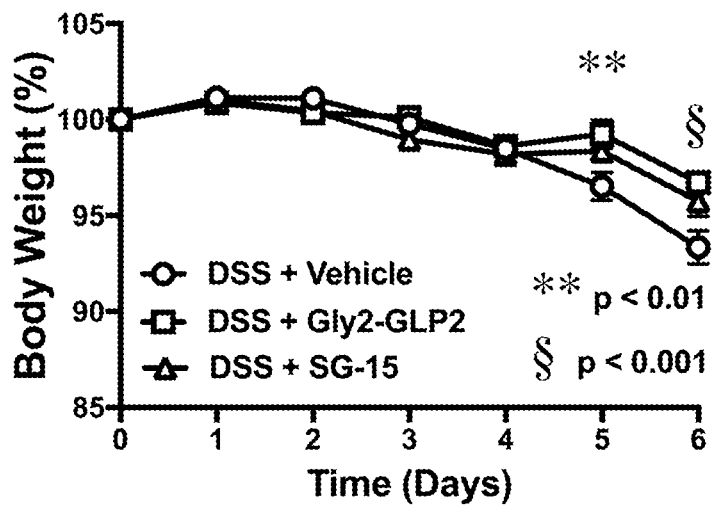
FIG. 6 shows effects of SG-15 administration on body weight in a DSS model of inflammatory bowel disease, as described in Example 1G.

Body weight was measured daily from mice included in the DSS model described in Example 1E. Percent change from starting weight on day 0 was determined for each mouse. SG-15 administration to DSS-treated mice significantly improved body weight compared to vehicle-treated DSS mice. Weight loss in mice treated with SG-15 at day 6 was similar to weight loss observed with Gly2-GLP2. Results are shown in FIG. 6. The graphs in FIG. 6 represent data pooled from the 2 individual experiments (n=20).

Figure 7:
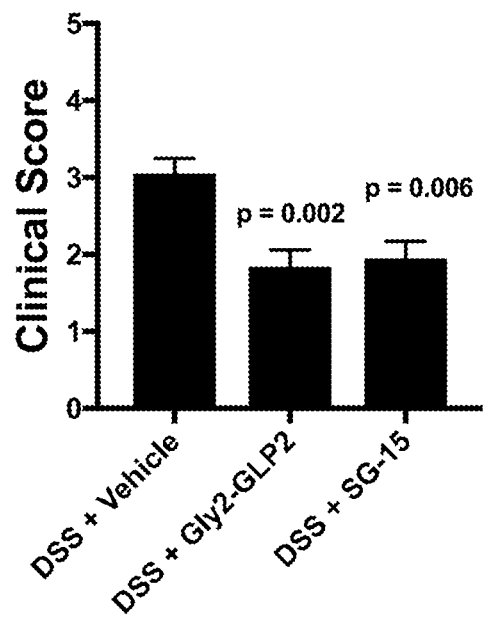
FIG. 7 shows effects of SG-15 administration on gross pathology in a DSS model of inflammatory bowel disease, as described in Example 1H.

H. Effects of SG-15 on Gross Pathology in a DSS Model of Inflammatory Bowel Disease Gross pathology observations were made in mice included in the concurrent DSS model performed in Example 1E. SG-15 administration to DSS treated mice significantly improved gross pathology as compared to vehicle treated DSS mice. No differences, however, were observed between clinical scores in DSS mice treated with Gly2-GLP2 and DSS mice treated with SG-15. The scoring system used was: (0)=no gross pathology, (1)=streaks of blood visible in feces, (2)=completely bloody fecal pellets, (3) bloody fecal material visible in cecum, (4) bloody fecal material in cecum and loose stool, (5)=rectal bleeding. Results are shown in FIG. 7, with the graph representing data pooled from the 2 individual experiments (n=20).

I. Effects of SG-15 on the Colon Length in a DSS Model of Inflammatory Bowel Disease The following experiment demonstrates the effects of SG-15 on colon shortening to treat in an in vivo model of inflammatory bowel disease.

Figure 8:
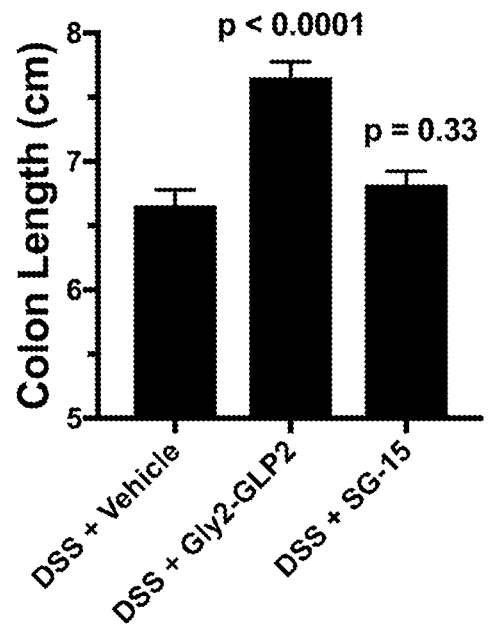
FIG. 8 shows effects of SG-15 administration on colon length in a DSS model of inflammatory bowel disease, as described in Example 1I.

Colon length was measured in mice included in the DSS model described in Example 1E. SG-15 administration to DSS treated mice reduced colon shortening elicited by DSS treatment. An improvement in colon length was observed with Gly2-GLP2 as a positive control. Results are shown in FIG. 8. The graph in FIG. 8 represents data pooled from the 2 individual experiments (n=20).

J. Effects of SG-15 on Colon Weight to Length Ratio in a DSS Model of Inflammatory Bowel Disease The following experiment demonstrates the effects of SG-15 as disclosed herein on changes in colon weight to length ratio induced by DSS treatment.

Figure 9:
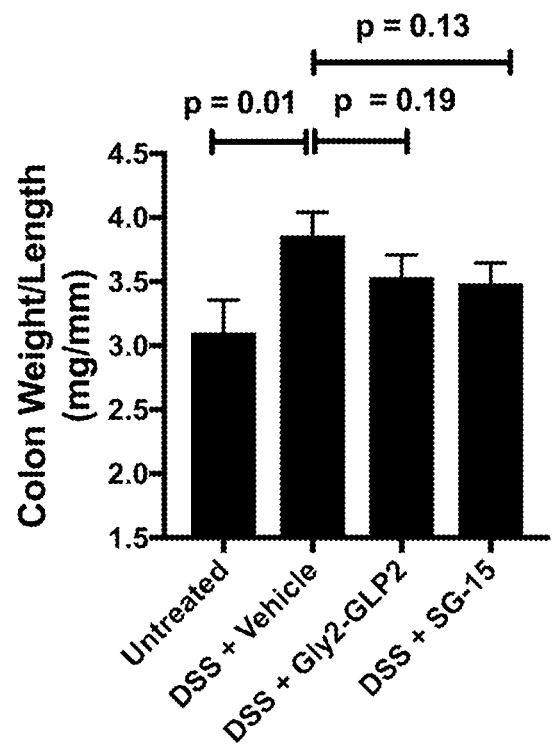
FIG. 9 shows effects of SG-15 administration on colon weight to length ratio in a DSS model of inflammatory bowel disease, as described in Example 1J.

Colon length and weight were measured in mice included in the DSS model study described in Example 1E. DSS-treated mice administered vehicle only resulted in colon shortening (see Example 1I), which in combination with increased tissue weight due to edema results in an increase in the tissue to weight ratio. Accordingly, the ratio of tissue weight to length can be used as a readout of DSS induced tissue damage. SG-15 administration to DSS treated mice (Example 1E) reduced the colon weight to length ratio elicited by DSS (DSS=3.9 mg/mm, DSS+SG-15=3.5 mg/mm; p=0.13). A reduction in colon weight to length ratio was also observed with Gly2-GLP2. However, no difference was observed between treated with SG-15 as compared to treatment with Gly2GLP2. Results are shown in FIG. 9. The graph in FIG. 9 represents data pooled from the 2 individual experiments (n=20).

Example 2. SG-16

A. Expression of SG-16

For experiments described in the examples below, a polynucleotide comprising a sequence encoding residues 1-119 of SEQ ID NO:9 (SG-16) was obtained by PCR amplification of genomic DNA obtained from *Eubacterium eligens* (C15-B4; DSM 3376 type strain), cloned into the pGEX-6-P1 vectors, expressed in *E. coli* transformed with the resultant vector construct, cleaved, and purified as described above in Example 1A. Purified protein was quantified by densitometry using bovine serum albumin as a reference following SDS-PAGE and Coomassie Brilliant Blue staining. Endotoxin levels were measured with Endosafe® nexgen-MCS™ (Charles River, Wilmington, MA) according to the manufacturer's instructions. Endotoxin levels of proteins used for the assays described herein were lower than 1 EU/mg.

B. Effect of SG-16 on Restoration of Epithelial Barrier Integrity Following Inflammation Induced Disruption The following experiment assesses the effects of an SG-16 protein as disclosed herein to restore gastrointestinal epithelial barrier integrity in vitro. Assays were performed and data were analyzed as described in Example 1B above to measure the effect of SG-16 on epithelial barrier function, muc2 gene expression, wound healing, and production of cytokines.

Figure 10A:
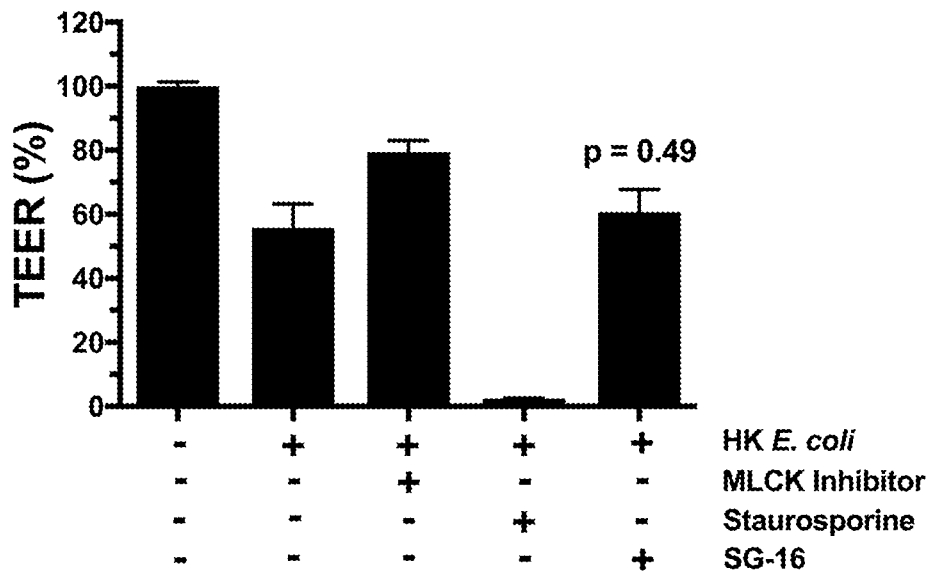
FIG. 10A and FIG. 10B show restoration, by SG-16, of epithelial barrier integrity following inflammation induced disruption, as described in Example 2B.
Figure 10B:
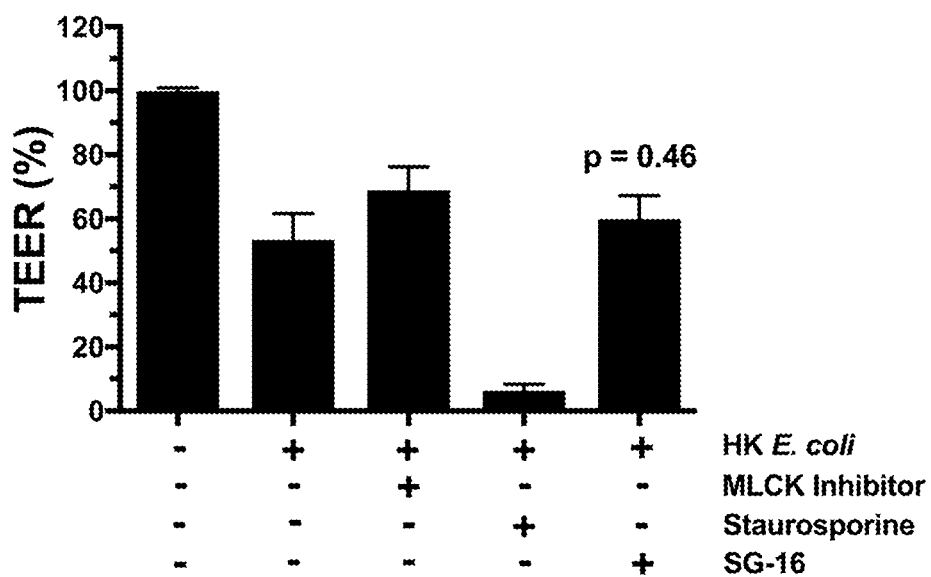

As described in Example 1B, a TEER assay was performed to study the effects of an SG protein on an in vitro intestinal epithelial barrier system which was challenged with heat killed *E. coli* (HK *E. coli*). SG-16 protein was added 30 minutes (FIG. 10A) or 6 hours (FIG. 10B) prior to exposure of both epithelial cells and monocytes to heat killed *Escherichia coli* (HK *E. coli*), inducing monocytes to produce inflammatory mediators resulting in disruption of the epithelial monolayer as indicated by a reduction in TEER. In FIG. 10A, TEER of epithelial cell barrier increased from 55.8% only when epithelial cells were exposed to heat killed *E. coli* to 60.7% when incubating epithelial cells with SG-16 for 30 minutes before exposing to HK *E. coli* (p=0.49). In FIG. 10B, epithelial cells pre-incubated with SG-16 for 6 hours before HK *E. coli* exposure showed an increase to about 60.0% in TEER from about 53.5% without SG-16 treatment (p=0.46). The graphs in FIGS. 10A-10B represent data pooled from 3 individual experiments (n=9).

C. Effect of SG-16 on TNF-α, IL-23, and IL-10 Production by Heat Killed *Escherichia coli*

The following experiment demonstrates the therapeutic ability of an SG-16 protein as disclosed herein to affect immune activation as measured by cytokine production. Effects of SG-16 on cytokine production in a TEER assay were assessed using the materials and methods detailed in Example 1C above.

Production of the cytokines TNF-α, IL-23, and IL-10 by monocytes was measured in the tissue culture supernatant from the basolateral chamber of the co-culture TEER assay performed in Example 2B.

Figure 11A:
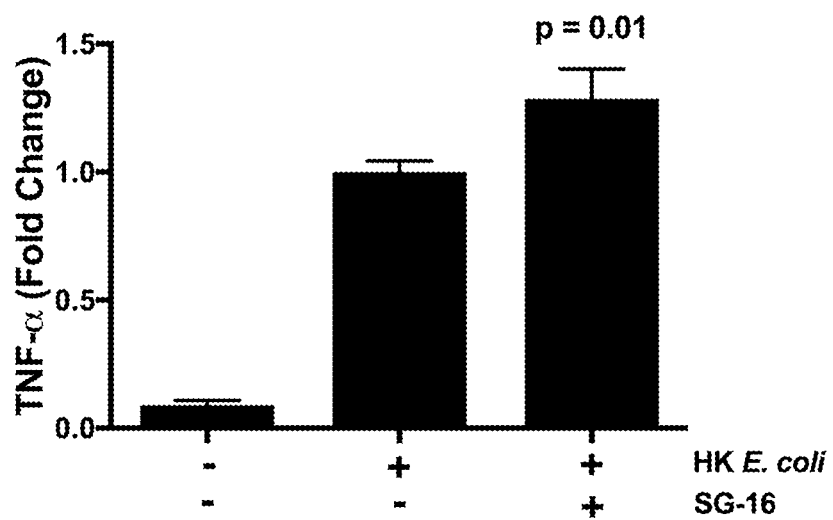
FIG. 11A shows effects of SG-16 administration on TNF-α production induced by heat killed *Escherichia coli* (HK *E. coli*), as described in Example 2C.
Figure 11B:
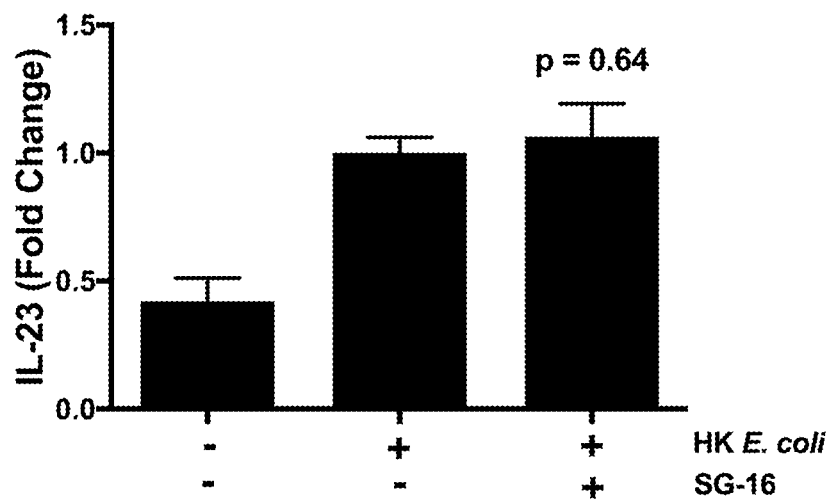
FIG. 11B shows effects of SG-16 administration on IL-23 production induced by HK *E. coli*, as described in Example 2C.
Figure 11C:
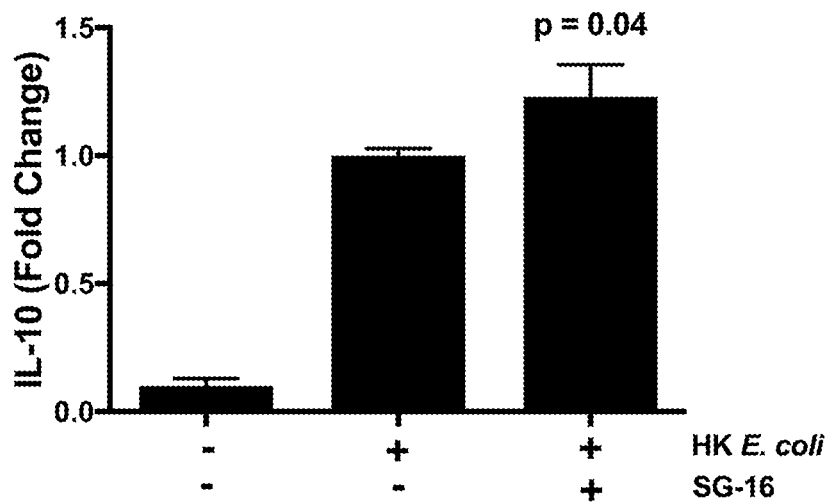
FIG. 11C shows effects of SG-16 administration on IL-10 production induced by HK *E. coli*, as described in Example 2C.

TNF-α, IL-23, and IL-10 production in untreated cells and cells pre-incubated with SG-16 for 6 hours prior to HK *E. coli* treatment was normalized to pg/ml concentrations elicited by HK *E. coli* only, which was set to 1.0. Pre-incubation with SG-16 significantly increased TNF-α production to 1.29 (p=0.01). Results are shown in FIG. 11A. Pre-incubation with SG-16 increased IL-23 production slightly to 1.06 (p=0.64). Results are shown in FIG. 11B. Pre-incubation with SG-16 significantly increased IL-10 production to 1.23 (p=0.04). Results are shown in FIG. 11C. The graphs in FIGS. 11A, 11B and tlC each represent data pooled from 3 individual experiments (n=9).

D. Effects of SG-16 on Mucin Expression Following Stimulation with Heat Killed *Escherichia coli*

The following experiment measures effects of an SG-16 protein as disclosed herein to increase mucin expression in gastrointestinal tissue. The experiment is therefore a demonstration of the functional utility of the therapeutic protein SG-16 to treat a gastrointestinal inflammatory disease, or disease involving impaired epithelial barrier integrity/function, where increased mucin expression would be beneficial.

Muc2 gene expression was measured in the epithelial cell monolayer from the apical chamber of the co-culture TEER assay described in Example 2B. Total RNA was isolated from the epithelial cell monolayer, cDNA was synthesized. qRT-PCR was performed on cDNA generated from the HCT8 & HT29-MTX cells treated with SG-16 (1 μg/ml; 40 nM) for 6 hours prior to addition of HK *E. coli* for 24 hours. muc2 gene expression is graphed as mean fold change ±SEM. Statistical analysis was performed by a one-way ANOVA compared to HK *E. coli* and a Fishers LSD test was used for multiple comparisons.

Figure 12:
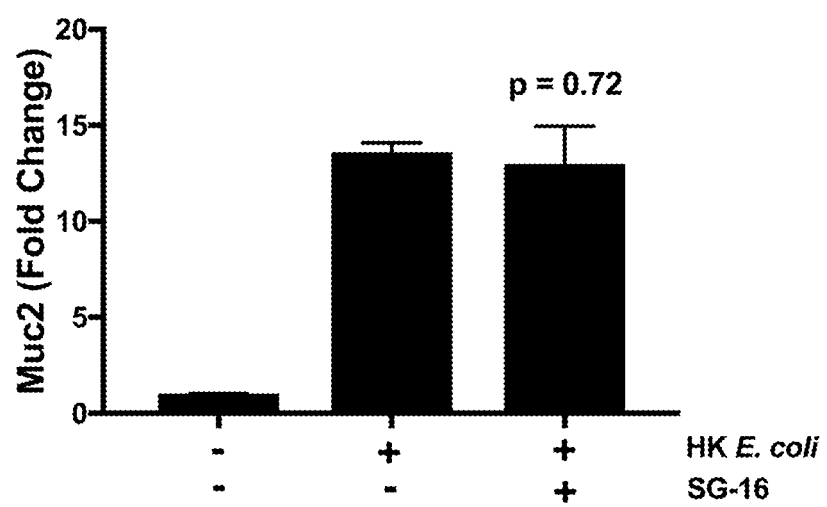
FIG. 12 shows effects of SG-16 administration on mucin expression following stimulation with HK *E. coli*, as described in Example 2D.

Analysis of muc2 gene expression revealed that no change in muc2 gene expression was observed in the epithelial cell monolayer with SG-16 pre-treatment for 6 hours prior to HK *E. co/i* stimulation, compared to the epithelial cell monolayer stimulated by HK *E. coli* without SG-16 pre-treatment (p=0.72). Results are shown in FIG. 12 with the graph representing data pooled from a single experiment (n=3).

E. Effects of SG-16 on Epithelial Cell Wound Healing

The following experiment demonstrates the therapeutic ability of SG-16 as disclosed herein to increase gastrointestinal epithelial cell wound healing. This experiment was performed as described in Example 1D in which HCT8 enterocytes and HT29-MTX goblet cells were used for the in vitro wound healing assay. Sample wells contained SG-16 protein at a concentration of 1 μg/ml diluted in cRPMI. Treatments were added to cells and incubated at 37° C.+5% $CO_2$ for 48 hours. Samples were normalized between 100% and 0% samples and values expressed as a percent growth.

Figure 13:
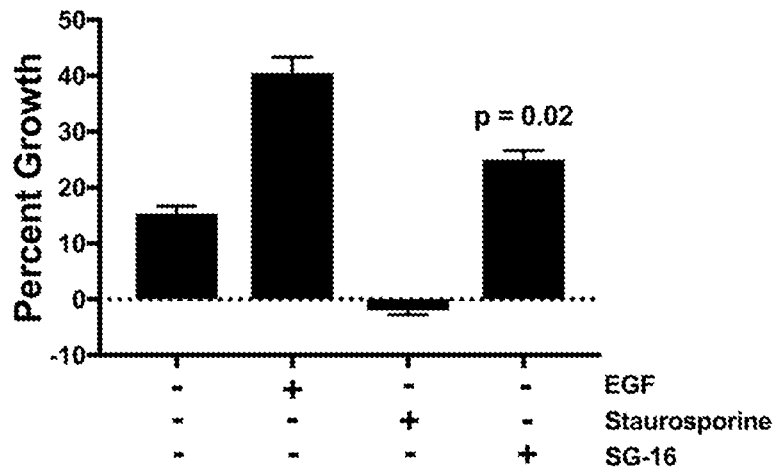
FIG. 13 shows effects of SG-16 administration on epithelial cell wound healing, as described in Example 2E.

As shown in FIG. 13, a significant increase in growth was observed with SG-16. In addition, control compounds (EGF and staurosporine) modulated wound healing as expected with EGF increasing proliferation, and staurosporine suppressing cell proliferation. Results are shown in FIG. 13, wherein the graph represents data from a single experiment (n=3).

F. SG-16 Demonstrates Therapeutic Activity in a DSS Model of Inflammatory Bowel Disease Example 2F demonstrates activity of an SG-16 protein as disclosed herein for the treatment of inflammatory bowel disease in an in vivo model. Specifically, the mice in Example 2F were treated with dextran sodium sulfate (DSS) according to the materials and methods described in detail in Example 1E above. In Example 2F, mice were treated with SG-16 protein approximately concurrent with (6 hours prior to) administration of DSS. In summary, 6 hours after the initial treatment with SG-16 the drinking water was changed to water containing 2.5% DSS. The mice were treated with 2.5% dextran sodium sulfate (DSS) in their drinking water for 6 days. Treatments were continued with SG-16 or Gly2-GLP2 b.i.d. in the morning and evening (every 8 and 16 hr) with i.p. injections at 50 nmoles/kg. Fresh 2.5% DSS drinking water was prepared every 2 days. The mice were then assessed for effects of SG-16 on clinically relevant markers of improved health.

Figure 14:
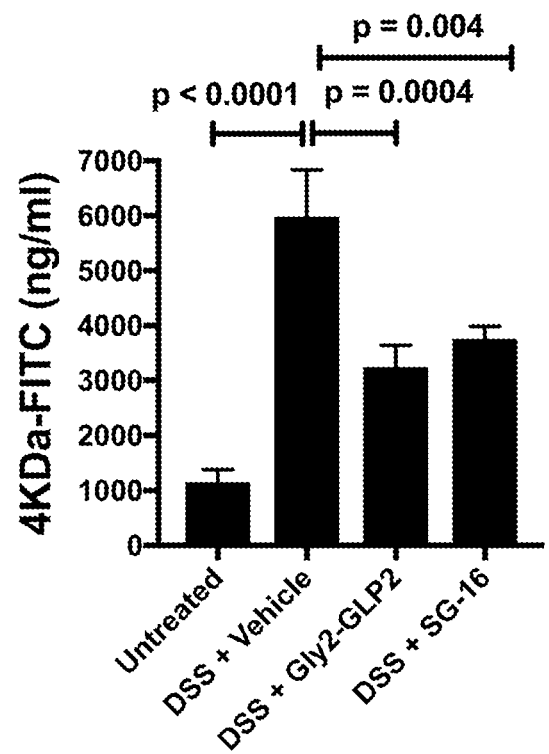
FIG. 14 shows effects of SG-16 administration on epithelial centric barrier function readouts in a DSS model of inflammatory bowel disease, as described in Example 2F.

On day 6, mice were fasted for 4 hours and then orally gavaged with 600 mg/kg 4KDa dextran labeled with fluorescein isothiocyanate (FITC) [4KDa-FITC]. One hour after the 4KDa-FITC gavage mice were euthanized, blood was collected and FITC signal was measured in serum. A significant increase in 4KDa-FITC dextran translocation across the epithelial barrier was observed in vehicle treated DSS mice in comparison to untreated mice. Additionally, a significant reduction in 4KDa-FITC dextran was observed in mice receiving DSS and treated with SG-16, as compared to DSS mice treated with vehicle. Results are shown in FIG. 14, and are presented as mean±SEM. The graph in FIG. 14 represents data from an individual experiment (n=10).

G. Effects of SG-16 on Inflammation Readouts Responsive to Impaired Barrier Function in a Concurrent DSS Model of Inflammatory Bowel Disease SG-16 was also assessed for its effects on the levels of LPS binding protein (LBP) in the blood of the DSS animals with and without SG-16 administration, following the materials and methods detailed in Example 1F above.

Figure 15:
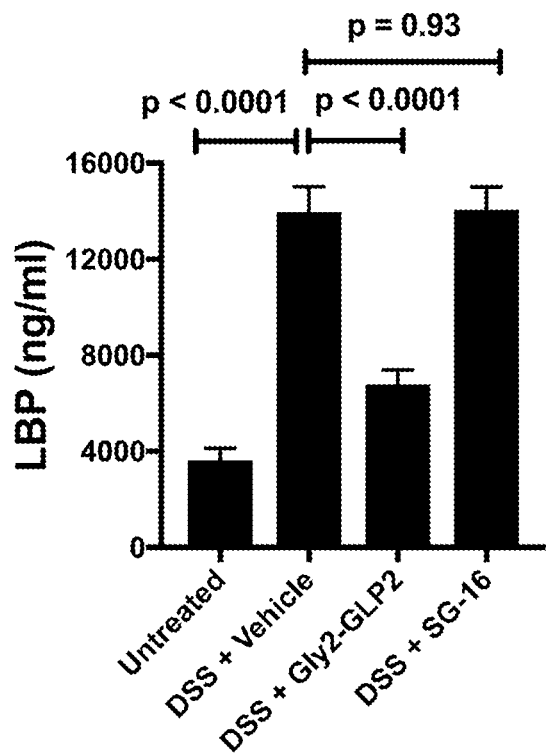
FIG. 15 shows effects of SG-16 administration on inflammatory readouts responsive to impaired barrier function in a DSS model of inflammatory bowel disease, as described in Example 2G.

LBP was measured by ELISA in the serum of mice tested in the DSS model described in Example 2F. A significant increase in LBP concentration was observed in vehicle-treated DSS mice, as compared to untreated mice. No change in LBP was observed in SG-16 treated mice given DSS as compared to DSS mice treated with vehicle. Results are shown in FIG. 15 and are presented as mean±SEM. The graph in FIG. 15 represents data from an individual experiment (n=10).

H. Effects of SG-16 on Weight Loss in a Concurrent DSS Model of Inflammatory Bowel Disease Also assessed was the therapeutic ability of an SG-16 protein as disclosed herein to ameliorate weight loss in an animal suffering from an inflammatory intestinal disorder, using materials and methods detailed in Example 1G above.

Figure 16:
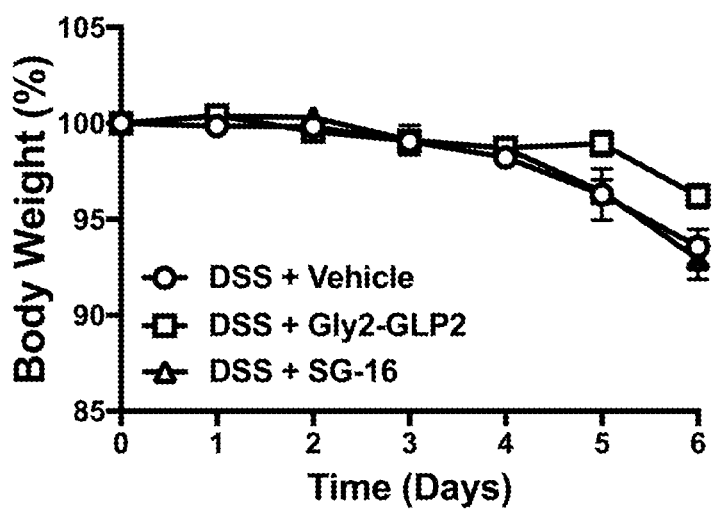
FIG. 16 shows effects of SG-16 administration on body weight in a DSS model of inflammatory bowel disease, as described in Example 2H.

Body weight was measured daily from mice included in the DSS model described in Example 2F. Percent change from starting weight on day 0 was determined for each mouse. SG-16 administration to DSS-treated mice significantly improved body weight compared to vehicle-treated DSS mice. SG-16 administration to DSS treated mice did not alter body weight as compared to vehicle treated DSS mice. Results are shown in FIG. 16, with the graph representing data from an individual experiment (n=10).

Figure 17:
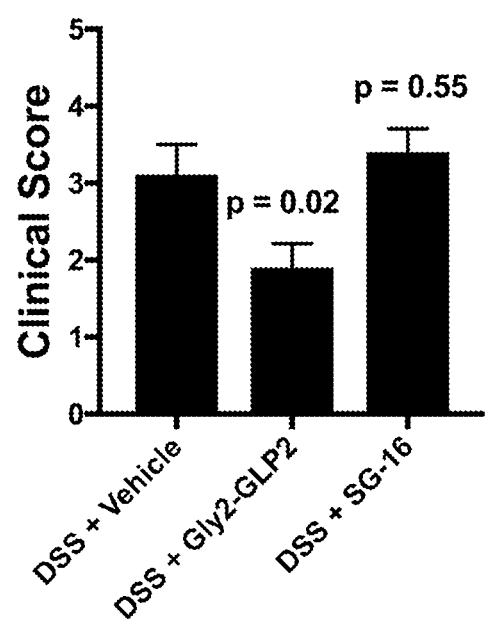
FIG. 17 shows effects of SG-16 administration on gross pathology in a DSS model of inflammatory bowel disease, as described in Example 2I.

I. Effects of SG-16 on Gross Pathology in a DSS Model of Inflammatory Bowel Disease Gross pathology observations were made in mice included in the concurrent DSS model performed in Example 2F, using the scoring system described in Example 1H above. SG-16 administration to DSS treated mice did not reduce gross pathology as compared to vehicle treated DSS mice. Results are shown in FIG. 17, with the graph representing data pooled from an individual experiment (n=10).

J. Effects of SG-16 on the Colon Length in a DSS Model of Inflammatory Bowel Disease The following experiment demonstrates the effects of SG-16 on colon shortening to treat in an in vivo model of inflammatory bowel disease.

Figure 18:
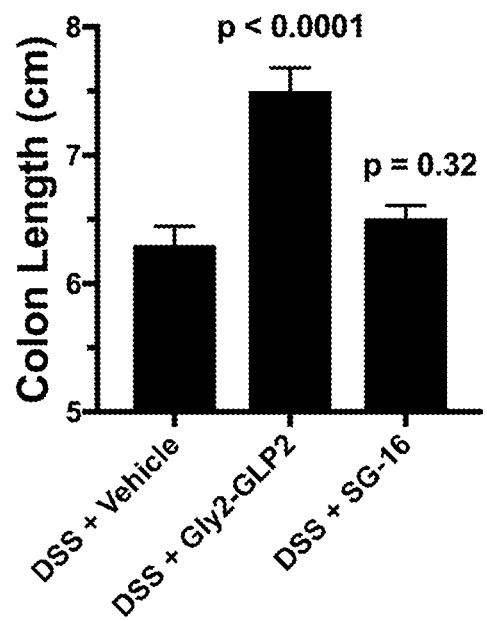
FIG. 18 shows effects of SG-16 administration on colon length in a DSS model of inflammatory bowel disease, as described in Example 2J.

Colon length was measured in mice included in the DSS model described in Example 2F. SG-16 administration to DSS treated mice slightly improved colon shortening elicited by DSS treatment. A significant improvement in colon length was observed with Gly2-GLP2 as a positive control and Gly2-GLP2 treatment had a significant improvement over SG-16. Results are shown in FIG. 18, with the graph representing data from an individual experiment (n=10).

K. Effects of SG-16 on Colon Weight to Length Ratio in a DSS Model of Inflammatory Bowel Disease The following experiment demonstrates the effects of SG-16 as disclosed herein on changes in colon weight to length ratio induced by DSS treatment.

Figure 19:
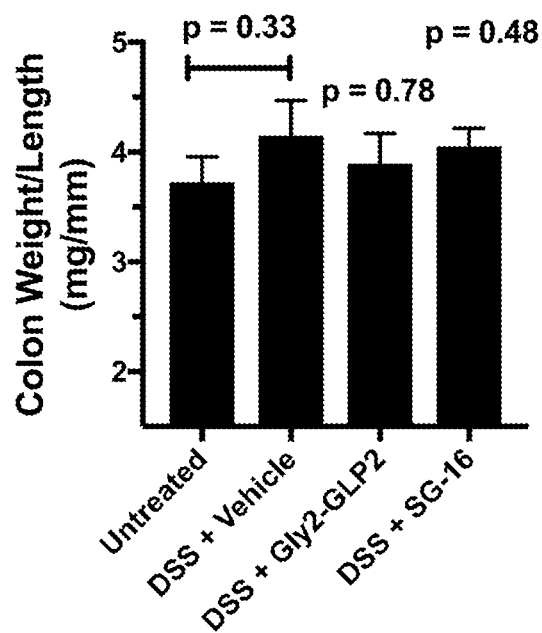
FIG. 19 shows effects of SG-16 administration on colon weight to length ratio in a DSS model of inflammatory bowel disease, as described in Example 2K.

Colon length and weight were measured in mice included in the DSS model study described in Example 2F. SG-16 administration to DSS treated mice did not alter the colon weight to length ratio elicited by DSS (DSS+vehicle=4.2 and DSS+SG-16=4.1; p=0.48). Results are shown in FIG. 19, with the graph representing data from an individual experiment (n=10).

Example 3. SG-17

A. Expression of SG-17

For experiments described in the examples below, a polynucleotide comprising a sequence encoding residues 1-327 of SEQ ID NO:13 (SG-17) was obtained by PCR amplification of genomic DNA obtained from *Eubacterium eligens* (C15-B4; DSM 3376 type strain), cloned into the pGEX-6-P1 vectors, expressed in *E. coli* transformed with the resultant vector construct, cleaved, and purified as described above in Example 1A. Purified protein was quantified by densitometry using bovine serum albumin as a reference following SDS-PAGE and Coomassie Brilliant Blue staining. Endotoxin levels were measured with Endosafe® nexgen-MCS™ (Charles River, Wilmington, MA) according to the manufacturer's instructions. Endotoxin levels of proteins used for the assays described herein were lower than 1 EU/mg.

B. Effect of SG-17 on Restoration of Epithelial Barrier Integrity Following Inflammation Induced Disruption The following experiment assesses the effects of an SG-17 protein as disclosed herein to restore gastrointestinal epithelial barrier integrity in vitro. Assays were performed and data were analyzed as described in Example 1B above to measure the effect of SG-17 on epithelial barrier function, muc2 gene expression, wound healing, and production of cytokines.

Figure 20A:
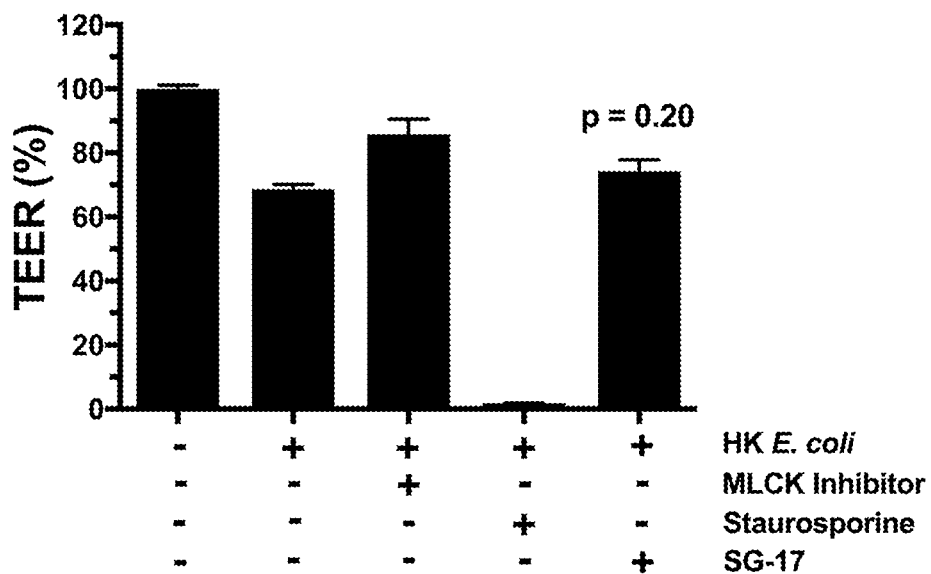
FIG. 20A and FIG. 20B show restoration, by SG-17, of epithelial barrier integrity following inflammation induced disruption, as described in Example 3B.
Figure 20B:
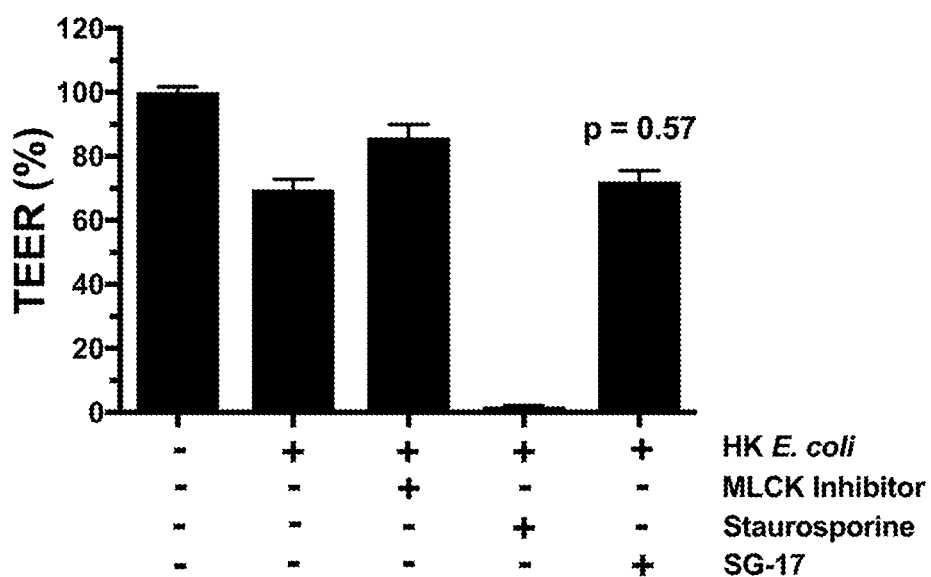

As described in Example 1B, a TEER assay was performed to study the effects of an SG protein on an in vitro intestinal epithelial barrier system which was challenged with heat killed E. coli (HK E. coli). SG-17 protein was added 30 minutes (FIG. 20A) or 6 hours (FIG. 20B) prior to exposure of both epithelial cells and monocytes to heat killed Escherichia coli (HK E. coli), inducing monocytes to produce inflammatory mediators resulting in disruption of the epithelial monolayer as indicated by a reduction in TEER. In FIG. 20A, TEER of epithelial cell barrier increased from 69.6% only when epithelial cells were exposed to HK E. coli to 72.0% when incubating epithelial cells with SG-17 for 30 minutes before exposing to HK E. coli (p=0.20). In FIG. 20B, epithelial cells pre-incubated with SG-17 for 6 hours before HK E. coli exposure showed an increase to about 74.2% in TEER from about 68.6% without SG-17 treatment (p=0.57). The graphs in FIGS. 20A-20B represent data pooled from 2 individual experiments (n=6).

C. Effect of SG-17 on TNF-α, IL-23, and IL-10 Production by Heat Killed Escherichia coli The following experiment demonstrates the therapeutic ability of an SG-17 protein as disclosed herein to affect immune activation as measured by cytokine production. Effects of SG-17 on cytokine production in a TEER assay were assessed using the materials and methods detailed in Example 1C above.

Production of the cytokines TNF-α, IL-23, and IL-10 by monocytes was measured in the tissue culture supernatant from the basolateral chamber of the co-culture TEER assay performed in Example 3B.

Figure 21A:
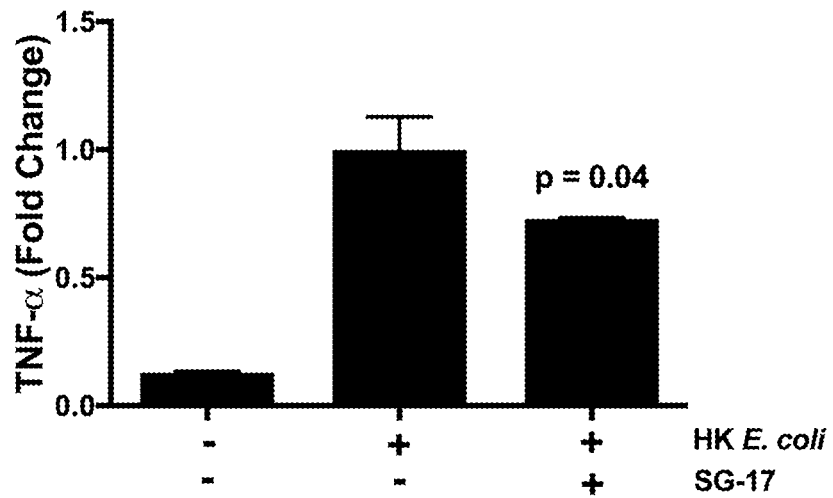
FIG. 21A shows effects of SG-17 administration on TNF-α production induced by heat killed *Escherichia coli* (HK *E. coli*), as described in Example 3C.
Figure 21B:
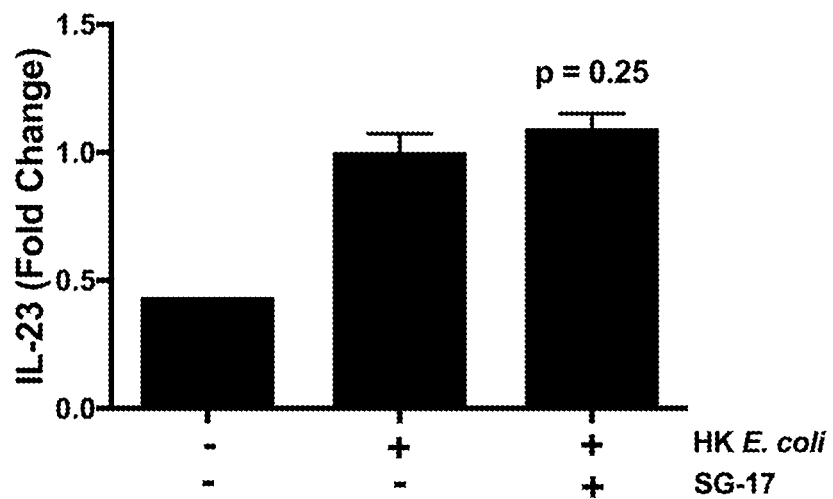
FIG. 21B shows effects of SG-17 administration on IL-23 production induced by HK *E. coli*, as described in Example 3C.
Figure 21C:
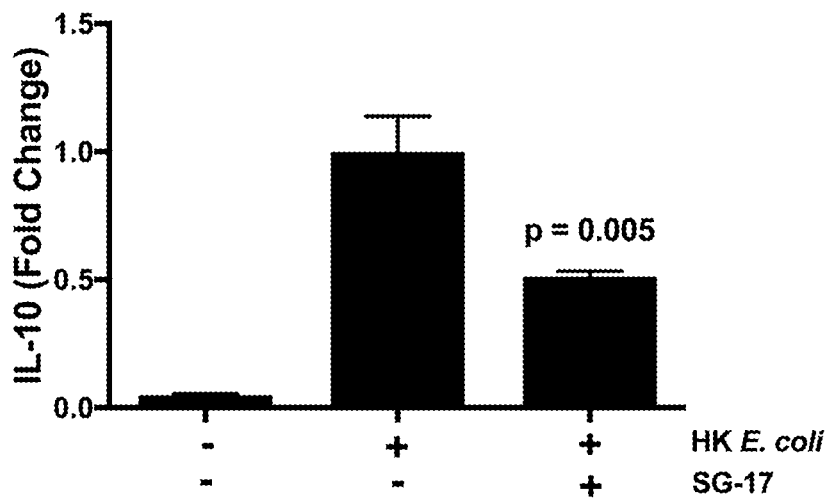
FIG. 21C shows effects of SG-17 administration on IL-10 production induced by HK *E. coli*, as described in Example 3C.

TNF-α, IL-23, and IL-10 production in untreated cells and cells pre-incubated with SG-17 for 6 hours prior to HK E. coli treatment was normalized to pg/ml concentrations elicited by HK E. coli only, which was set to 1.0. Pre-incubation with SG-17 significantly reduced TNF-α production to 0.73 (p=0.04). Results are shown in FIG. 21A. Pre-incubation with SG-17 increased IL-23 production to 1.10 (p=0.25). Results are shown in FIG. 21B. Pre-incubation with SG-17 significantly reduced IL-10 production to 0.51 (p=0.005). Results are shown in FIG. 21C. The graphs in FIGS. 21A, 21B and 21C each represent data from an individual experiment (n=3).

D. Effects of SG-17 on Mucin Expression Following Stimulation with Heat Killed Escherichia coli The following experiment measures effects of an SG-17 protein as disclosed herein to increase mucin expression in gastrointestinal tissue. The experiment is therefore a demonstration of the functional utility of the therapeutic protein SG-17 to treat a gastrointestinal inflammatory disease, or disease involving impaired epithelial barrier integrity/function, where increased mucin expression would be beneficial.

Muc2 gene expression was measured in the epithelial cell monolayer from the apical chamber of the co-culture TEER assay described in Example 3B, following the materials and methods detailed in Example 2D. Total RNA was isolated from the epithelial cell monolayer, cDNA was synthesized. qRT-PCR was performed on cDNA generated from the HCT8 & HT29-MTX cells treated with SG-17 (1 μg/ml; 40 nM) for 6 hours prior to addition of HK E. coli for 24 hours. muc2 gene expression is graphed as mean fold change ±SEM. Statistical analysis was performed by a one-way ANOVA compared to HK E. coli and a Fishers LSD test was used for multiple comparisons.

Figure 22:
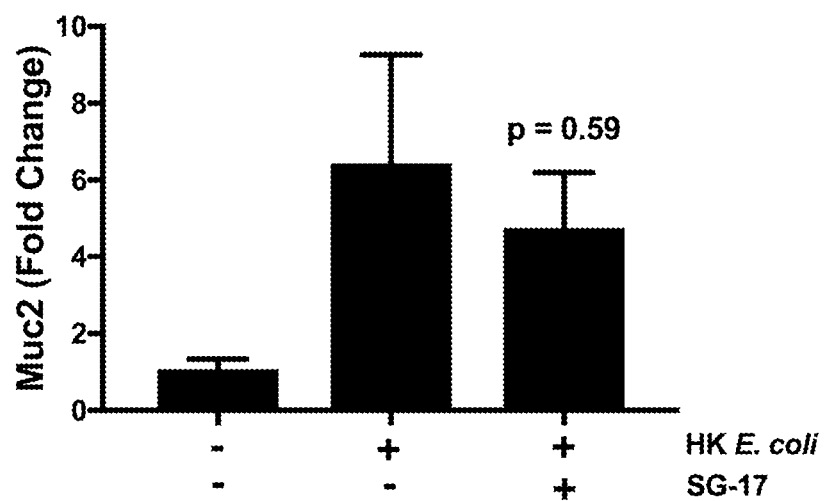
FIG. 22 shows effects of SG-17 administration on mucin expression following stimulation with HK *E. coli*, as described in Example 3D.

A decrease in muc2 gene expression was observed in the epithelial cell monolayer with SG-17 pre-treatment pre-treatment for 6 hours prior to HK E. coli stimulation, compared to the epithelial cell monolayer stimulated by HK E. coli without SG-17 pre-treatment (p=0.59). Results are shown in FIG. 22 with the graph representing data pooled from 2 independent experiments (n=3).

E. Effects of SG-17 on Epithelial Cell Wound Healing

The following experiment demonstrates the therapeutic ability of SG-17 as disclosed herein to increase gastrointestinal epithelial cell wound healing. This experiment was performed as described in Example 1D in which HCT8 enterocytes and HT29-MTX goblet cells were used for the in vitro wound healing assay. Sample wells contained SG-17 protein at a concentration of 1 μg/ml diluted in cRPMI. Treatments were added to cells and incubated at 37° C.+5% $CO_2$ for 48 hours. Samples were normalized between 100% and 0% samples and values expressed as a percent growth.

Figure 23:
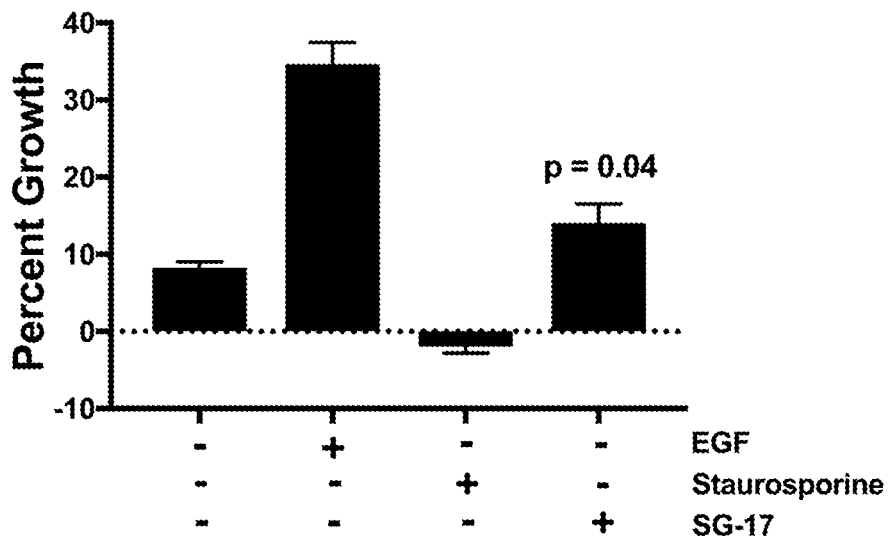
FIG. 23 shows effects of SG-17 administration on epithelial cell wound healing, as described in Example 3E.

As shown in FIG. 23, a significant increase in growth was observed with SG-17. In addition, control compounds (EGF and staurosporine) modulated wound healing as expected with EGF increasing proliferation, and staurosporine suppressing cell proliferation. Results are shown in FIG. 23, with the graph representing data from 4 replicate experiments (n=18).

F. Effect of SG-17 on Epithelial Centric Barrier Function Readouts in a DSS Model of Inflammatory Bowel Disease Example 3F demonstrates activity of an SG-17 protein as disclosed herein for the treatment of inflammatory bowel disease in an in vivo model. Specifically, the mice in Example 3F were treated with dextran sodium sulfate (DSS) according to the materials and methods described in detail in Example 1E above. In Example 3F, mice were treated with SG-17 protein approximately concurrent with (6 hours prior to) administration of DSS. In summary, 6 hours after the initial treatment with SG-17 the drinking water was changed to water containing 2.5% DSS. The mice were treated with 2.5% dextran sodium sulfate (DSS) in their drinking water for 6 days. Treatments were continued with SG-17 or Gly2-GLP2 b.i.d. in the morning and evening (every 8 and 16 hr) with i.p. injections at 50 nmoles/kg. Fresh 2.5% DSS drinking water was prepared every 2 days. The mice were then assessed for effects of SG-17 on clinically relevant markers of improved health.

Figure 24:
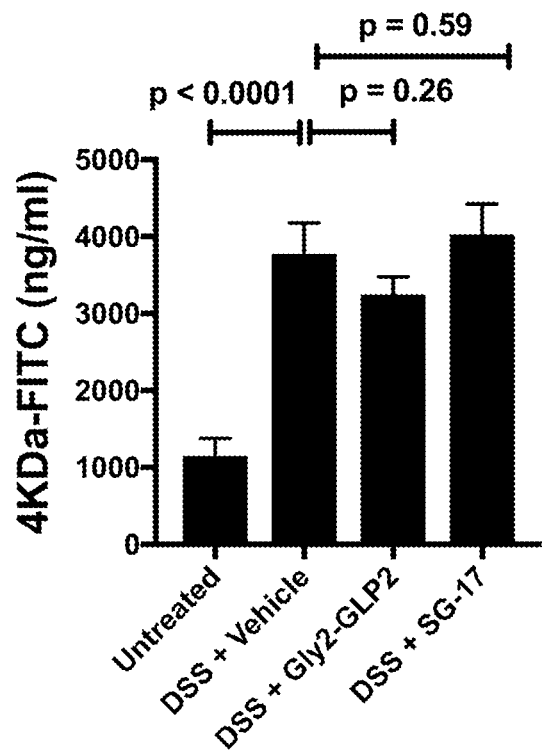
FIG. 24 shows effects of SG-17 administration on epithelial centric barrier function readouts in a DSS model of inflammatory bowel disease, as described in Example 3F.

On day 6, mice were fasted for 4 hours and then orally gavaged with 600 mg/kg 4KDa dextran labeled with fluorescein isothiocyanate (FITC) [4KDa-FITC]. One hour after the 4KDa-FITC gavage mice were euthanized, blood was collected and FITC signal was measured in serum. A significant increase in 4KDa-FITC dextran translocation across the epithelial barrier was observed in vehicle treated DSS mice in comparison to untreated mice. 4KDa-FITC dextran was not altered in mice receiving DSS and treated with SG-17, as compared to DSS mice treated with vehicle. Results are shown in FIG. 24, and are presented as mean±SEM. The graph in FIG. 24 represents data from an individual experiment (n=10).

G. Effects of SG-17 on Inflammation Readouts Responsive to Impaired Barrier Function in a Concurrent DSS Model of Inflammatory Bowel Disease SG-17 was also assessed for its effects on the levels of LPS binding protein (LBP) in the blood of the DSS animals with and without SG-17 administration, following the materials and methods detailed in Example 1F above.

LBP was measured by ELISA in the serum of mice tested in the DSS model described in Example 3F. A significant increase in LBP concentration was observed in vehicle-treated DSS mice, as compared to untreated mice. Additionally, a significant reduction in LBP was observed in SG-17 treated mice given DSS as compared to DSS mice treated with vehicle. Furthermore, SG-17 had a greater impact on LBP concentration as compared to the control peptide Gly2-

Figure 25:
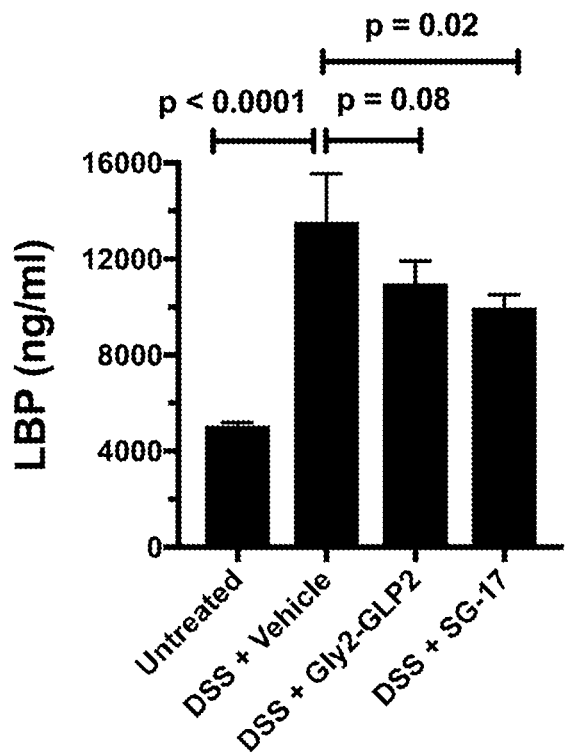
FIG. 25 shows effects of SG-17 administration on inflammatory readouts responsive to impaired barrier function in a DSS model of inflammatory bowel disease, as described in Example 3G.

GLP2. Results are shown in FIG. 25 and are presented as mean±SEM. The graph in FIG. 25 represents data from an individual experiment (n=10).

H. Effects of SG-17 on Weight Loss in a Concurrent DSS Model of Inflammatory Bowel Disease Also assessed was the therapeutic ability of an SG-17 protein as disclosed herein to ameliorate weight loss in an animal suffering from an inflammatory intestinal disorder, using materials and methods detailed in Example 1G above.

Figure 26:
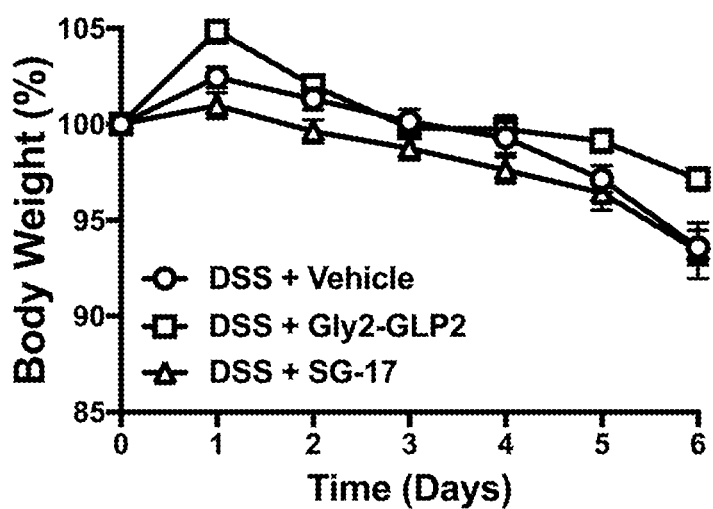
FIG. 26 shows effects of SG-17 administration on body weight in a DSS model of inflammatory bowel disease, as described in Example 3H.

Body weight was measured daily from mice included in the DSS model described in Example 3F. Percent change from starting weight on day 0 was determined for each mouse. SG-17 administration to DSS-treated mice did not alter body weight as compared to vehicle treated DSS mice. Results are shown in FIG. 26, with the graph representing data from an individual experiment (n=10).

Figure 27:
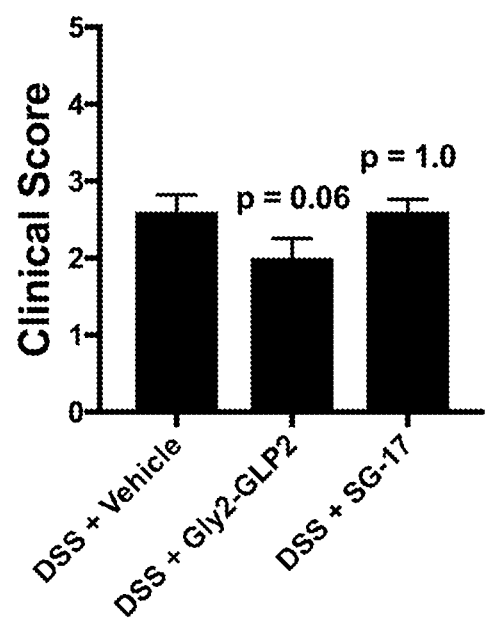
FIG. 27 shows effects of SG-17 administration on gross pathology in a DSS model of inflammatory bowel disease, as described in Example 3I.

I. Effects of SG-17 on Gross Pathology in a DSS Model of Inflammatory Bowel Disease Gross pathology observations were made in mice included in the concurrent DSS model performed in Example 3F, using the scoring system described in Example 1H above. SG-17 administration to DSS treated mice did not reduce gross pathology as compared to vehicle treated DSS mice. Results are shown in FIG. 27, with the graph representing data pooled from an individual experiment (n=10).

J. Effects of SG-17 on the Colon Length in a DSS Model of Inflammatory Bowel Disease The following experiment demonstrates the effects of SG-17 on colon shortening to treat in an in vivo model of inflammatory bowel disease.

Figure 28:
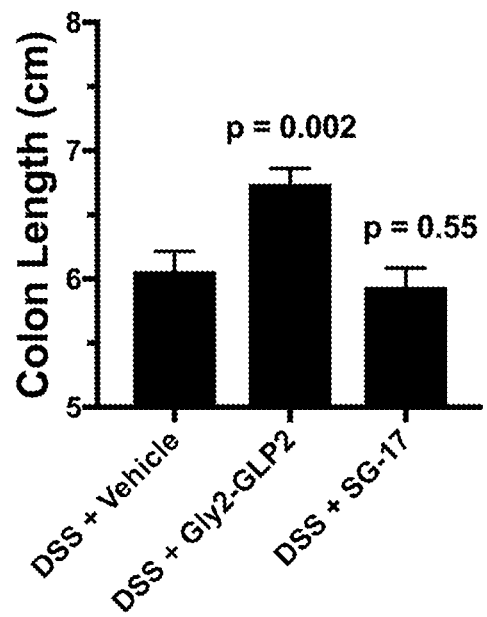
FIG. 28 shows effects of SG-17 administration on colon length in a DSS model of inflammatory bowel disease, as described in Example 3J.

Colon length was measured in mice included in the DSS model described in Example 3F. SG-17 administration to DSS treated mice did not reduce colon shortening elicited by DSS treatment. A significant improvement in colon length was observed with Gly2-GLP2 as a positive control and Gly2-GLP2 treatment had a significant improvement over SG-17. Results are shown in FIG. 28, with the graph representing data from an individual experiment (n=10).

K. Effects of SG-17 on Colon Weight to Length Ratio in a DSS Model of Inflammatory Bowel Disease The following experiment demonstrates the effects of SG-17 as disclosed herein on changes in colon weight to length ratio induced by DSS treatment.

Figure 29:
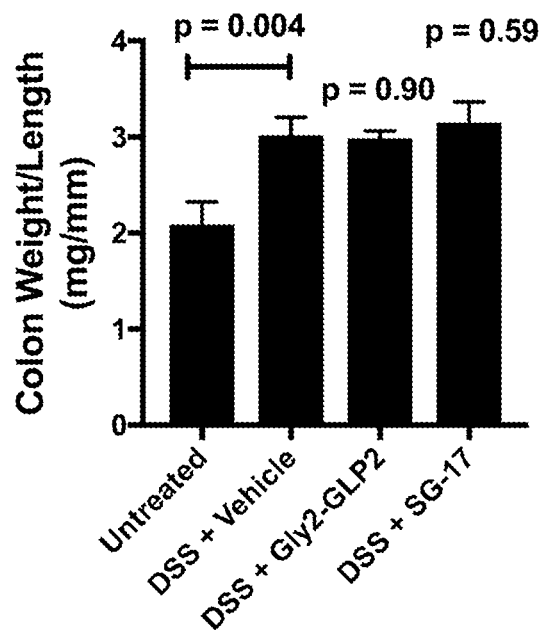
FIG. 29 shows effects of SG-17 administration on colon weight to length ratio in a DSS model of inflammatory bowel disease, as described in Example 3K.

Colon length and weight were measured in mice included in the DSS model study described in Example 3F. SG-17 administration to DSS treated mice did not alter the colon weight to length ratio elicited by DSS (DSS+vehicle=3.02 and DSS+SG-17=3.14; p=0.59). Results are shown in FIG. 29, with the graph representing data from an individual experiment (n=10).

Example 4. SG-18

A. Expression of SG-18

For experiments described in the examples below, a polynucleotide comprising a sequence encoding residues 1-267 of SEQ ID NO:19 (SG-18) was obtained by PCR amplification of genomic DNA obtained from *Clostridium bartlettii* (ATCC® BAA-827™ Type Strain; also designated 16795 per DSMZ), cloned into the pGEX-6-P1 vectors, expressed in *E. coli* transformed with the resultant vector construct, cleaved, and purified as described above in Example 1A. Purified protein was quantified by densitometry using bovine serum albumin as a reference following SDS-PAGE and Coomassie Brilliant Blue staining. Endotoxin levels were measured with Endosafe® nexgen-MCS™ (Charles River, Wilmington, MA) according to the manufacturer's instructions. Endotoxin levels of proteins used for the assays described herein were lower than 1 EU/mg.

B. Effect of SG-18 on Restoration of Epithelial Barrier Integrity Following Inflammation Induced Disruption The following experiment assesses the effects of an SG-18 protein as disclosed herein to restore gastrointestinal epithelial barrier integrity in vitro. Assays were performed and data were analyzed as described in Example 1B above to measure the effect of SG-18 on epithelial barrier function, wound healing, and production of cytokines.

Figure 30A:
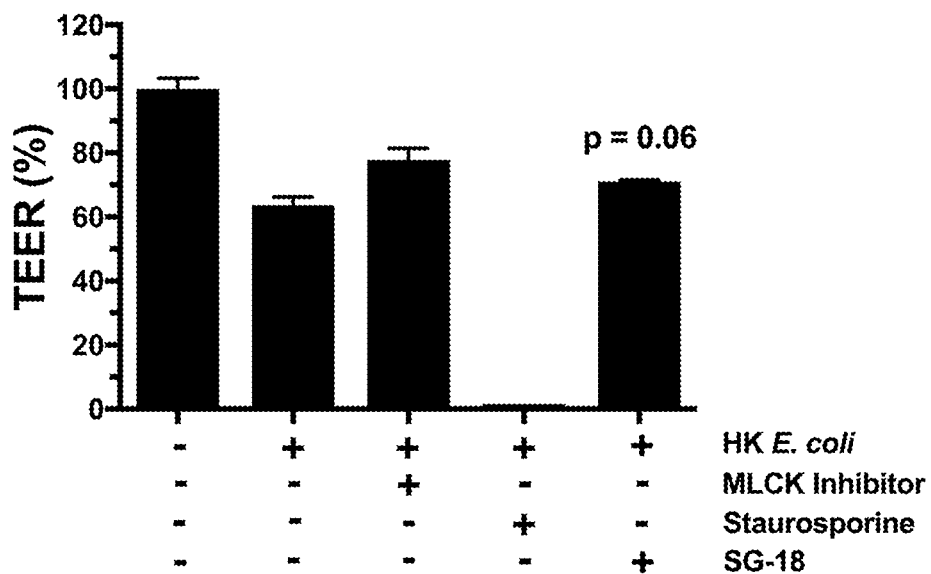
FIG. 30A and FIG. 30B show restoration, by SG-18, of epithelial barrier integrity following inflammation induced disruption, as described in Example 4B.
Figure 30B:
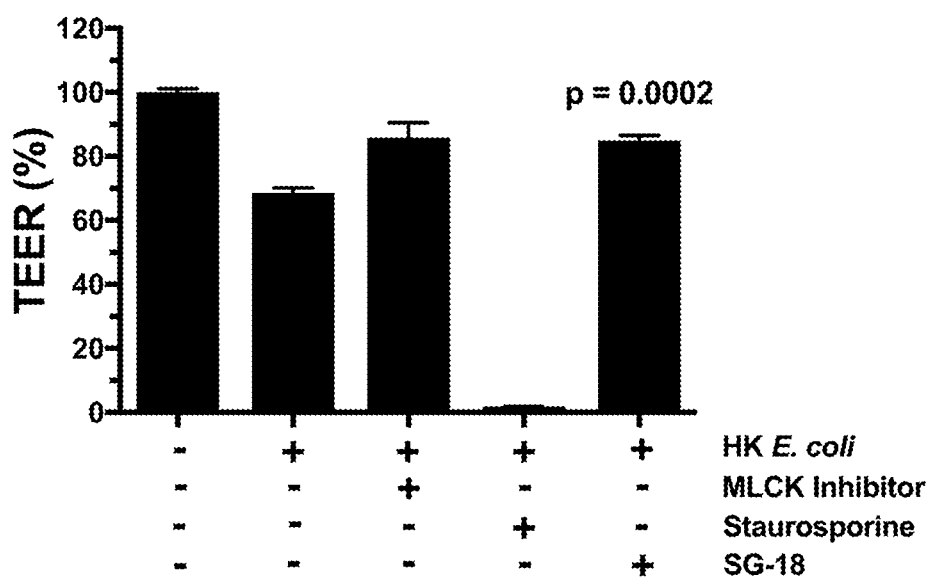

As described in Example 1B, a TEER assay was performed to study the effects of an SG protein on an in vitro intestinal epithelial barrier system which was challenged with heat killed *E. coli* (HK *E. coli*). SG-18 protein was added 30 minutes (FIG. 30A) or 6 hours (FIG. 30B) prior to exposure of both epithelial cells and monocytes to heat killed *Escherichia coli* (HK *E. coli*), inducing monocytes to produce inflammatory mediators resulting in disruption of the epithelial monolayer as indicated by a reduction in TEER. In FIG. 30A, TEER of epithelial cell barrier increased from 63.6% only when epithelial cells were exposed to HK *E. coli* to 71.0% when incubating epithelial cells with SG-18 for 30 minutes before exposing to HK *E. coli* (p=0.06). In FIG. 30B, epithelial cells pre-incubated with SG-18 for 6 hours before HK *E. coli* exposure showed an increase to about 85.0% in TEER from about 68.6% without SG-18 treatment (p=0.0002). The graphs in FIGS. 30A-30B represent data pooled from 2 individual experiments (n=6).

C. Effect of SG-18 on TNF-α, IL-23, and IL-10 Production by Heat Killed *Escherichia coli*

The following experiment demonstrates the therapeutic ability of an SG-18 protein as disclosed herein to affect immune activation as measured by cytokine production. Effects of SG-18 on cytokine production in a TEER assay were assessed using the materials and methods detailed in Example 1C above.

Production of the cytokines TNF-α, IL-23, and IL-10 by monocytes was measured in the tissue culture supernatant from the basolateral chamber of the co-culture TEER assay performed in Example 4B.

Figure 31A:
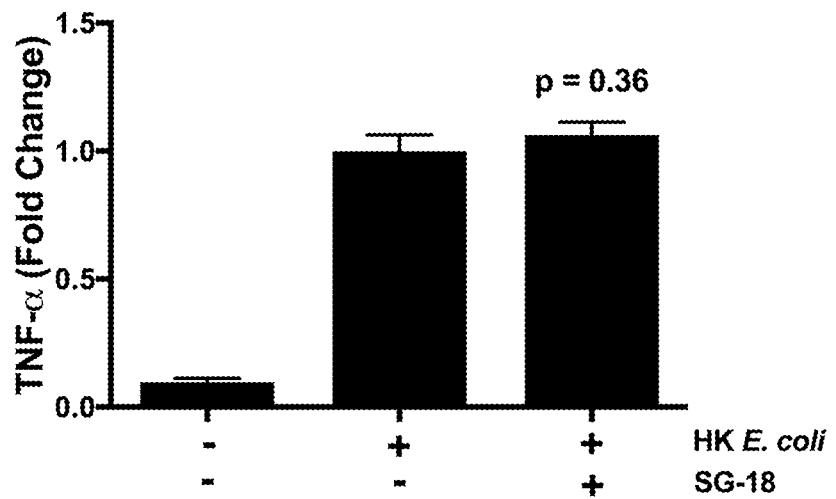
FIG. 31A shows effects of SG-18 administration on TNF-α production induced by heat killed *Escherichia coli* (HK *E. coli*), as described in Example 4C.
Figure 31B:
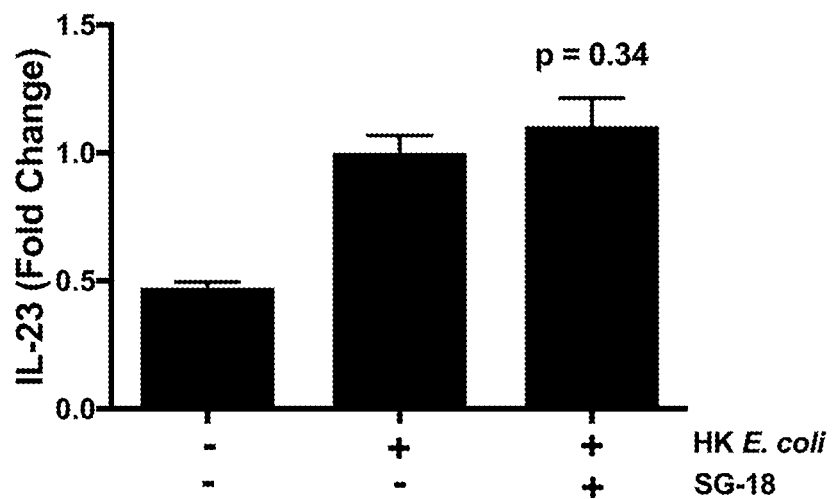
FIG. 31B shows effects of SG-18 administration on IL-23 production induced by HK *E. coli*, as described in Example 4C.
Figure 31C:
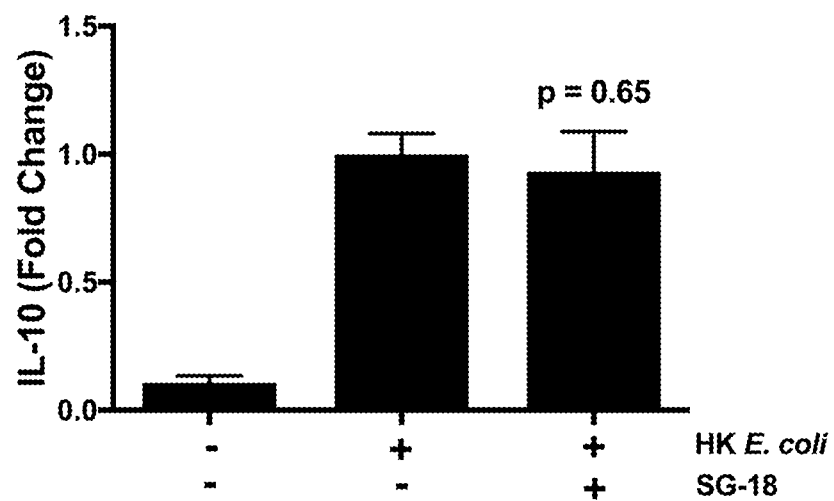
FIG. 31C shows effects of SG-18 administration on IL-10 production induced by HK *E. coli*, as described in Example 4C.

TNF-α, IL-23, and IL-10 production in untreated cells and cells pre-incubated with SG-18 for 6 hours prior to HK *E. coli* treatment was normalized to pg/ml concentrations elicited by HK *E. coli* only, which was set to 1.0. Pre-incubation with SG-18 increased TNF-α production to 1.06 (p=0.36). Results are shown in FIG. 31A. Pre-incubation with SG-18 increased IL-23 production to 1.10 (p=0.34). Results are shown in FIG. 31B. Pre-incubation with SG-18 reduced IL-10 production slightly to 0.93 (p=0.65). Results are shown in FIG. 31C. The graphs in FIGS. 31A, 31B and 31C each represent data from 2 individual experiments (n=6).

D. Effects of SG-18 on Epithelial Cell Wound Healing

The following experiment demonstrates the therapeutic ability of SG-18 as disclosed herein to increase gastrointestinal epithelial cell wound healing. This experiment was performed as described in Example 1D in which HCT8 enterocytes and HT29-MTX goblet cells were used for the in vitro wound healing assay. Sample wells contained SG-18 protein at a concentration of 1 μg/ml diluted in cRPMI. Treatments were added to cells and incubated at 37° C.+5% CO₂ for 48 hours. Samples were normalized between 100% and 0% samples and values expressed as a percent growth.

Figure 32:
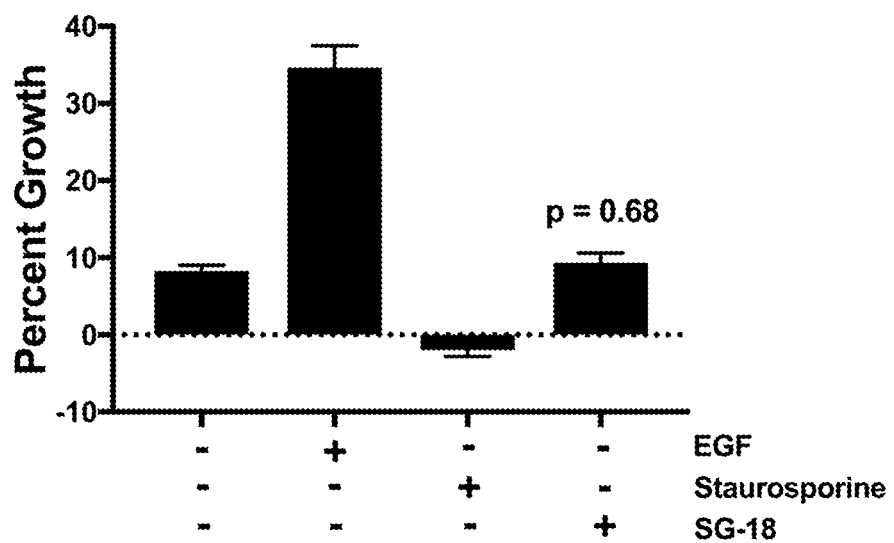
FIG. 32 shows effects of SG-18 administration on epithelial cell wound healing, as described in Example 4D.

As shown in FIG. 32, a slight increase in growth was observed with SG-18 (p=0.68). In addition, control compounds (EGF and staurosporine) modulated wound healing as expected with EGF increasing proliferation, and staurosporine suppressing cell proliferation. Results shown in FIG. 32 represent data pooled from 4 replicate experiments (n=18).

E. SG-18 Demonstrates Therapeutic Activity in a DSS Model of Inflammatory Bowel Disease Example 4E demonstrates activity of an SG-18 protein as disclosed herein for the treatment of inflammatory bowel disease in an in vivo model. Specifically, the mice in Example 4E were treated with dextran sodium sulfate (DSS) according to the materials and methods described in detail in Example 1E above. In Example 4E, mice were treated with SG-18 protein approximately concurrent with (6 hours prior to) administration of DSS. In summary, 6 hours after the initial treatment with SG-18 the drinking water was changed to water containing 2.5% DSS. The mice were treated with 2.5% dextran sodium sulfate (DSS) in their drinking water for 6 days. Treatments were continued with SG-18 or Gly2-GLP2 b.i.d. in the morning and evening (every 8 and 16 hr) with i.p. injections at 50 nmoles/kg. Fresh 2.5% DSS drinking water was prepared every 2 days. The mice were then assessed for effects of SG-18 on clinically relevant markers of improved health.

Figure 33:
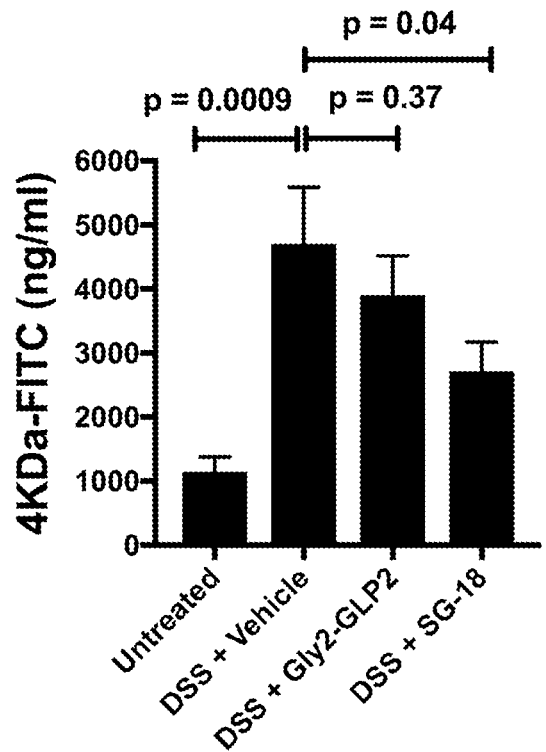
FIG. 33 shows effects of SG-18 administration on epithelial centric barrier function readouts in a DSS model of inflammatory bowel disease, as described in Example 4E.

On day 6, mice were fasted for 4 hours and then orally gavaged with 600 mg/kg 4KDa dextran labeled with fluorescein isothiocyanate (FITC) [4KDa-FITC]. One hour after the 4KDa-FITC gavage mice were euthanized, blood was collected and FITC signal was measured in serum. A significant increase in 4KDa-FITC dextran translocation across the epithelial barrier was observed in vehicle treated DSS mice in comparison to untreated mice. Additionally, a significant reduction in 4KDa-FITC dextran was observed in mice receiving DSS and treated with SG-18, as compared to DSS mice treated with vehicle. The magnitude of 4KDa-FITC dextran translocation observed for SG-18 was even lower than the positive control, Gly2-GLP2, which is known for enhancing intestinal epithelial barrier function. Results are shown in FIG. 33, and are presented as mean±SEM. The graph in FIG. 33 represents data pooled from 2 individual experiments (n=20).

F. Effects of SG-18 on Inflammation Readouts Responsive to Impaired Barrier Function in a Concurrent DSS Model of Inflammatory Bowel Disease SG-18 was also assessed for its effects on the levels of LPS binding protein (LBP) in the blood of the DSS animals with and without SG-18 administration, following the materials and methods detailed in Example 1F above.

Figure 34:
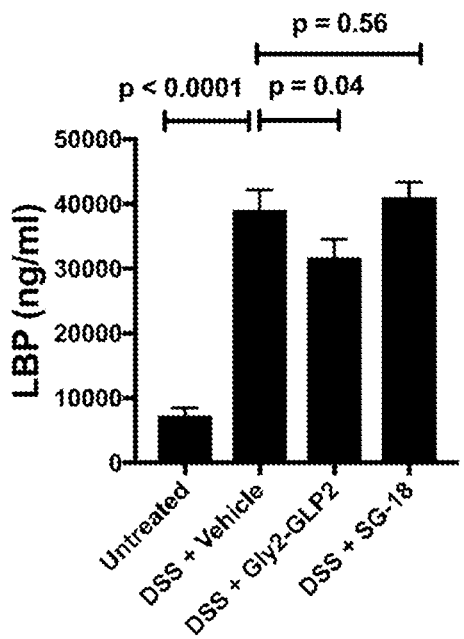
FIG. 34 shows effects of SG-18 administration on inflammatory readouts responsive to impaired barrier function in a DSS model of inflammatory bowel disease, as described in Example 4F.

LBP was measured by ELISA in the serum of mice tested in the DSS model described in Example 4E. A significant increase in LBP concentration was observed in vehicle-treated DSS mice, as compared to untreated mice. Similar levels in LBP were observed in SG-18 treated mice given DSS as compared to DSS mice treated with vehicle. Results are shown in FIG. 34 and are presented as mean±SEM. The graph in FIG. 34 represents data pooled from 2 individual experiments (n=20).

G. Effects of SG-18 on Weight Loss in a Concurrent DSS Model of Inflammatory Bowel Disease Also assessed was the therapeutic ability of an SG-18 protein as disclosed herein to ameliorate weight loss in an animal suffering from an inflammatory intestinal disorder, using materials and methods detailed in Example 1G above.

Figure 35:
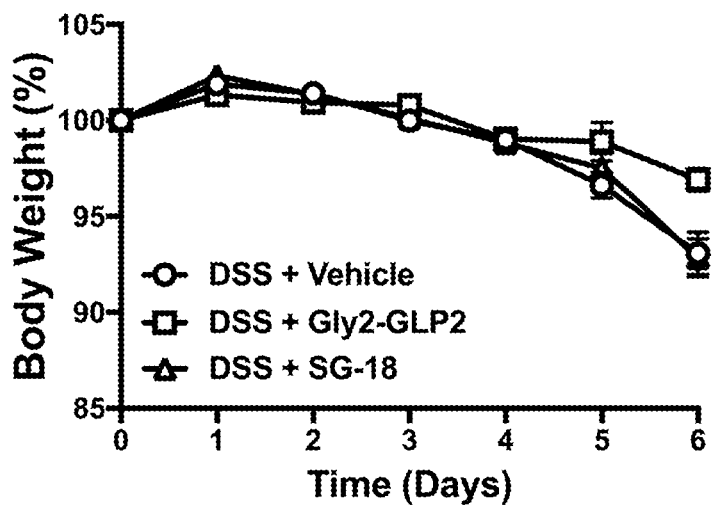
FIG. 35 shows effects of SG-18 administration on body weight in a DSS model of inflammatory bowel disease, as described in Example 4G.

Body weight was measured daily from mice included in the DSS model described in Example 4E. Percent change from starting weight on day 0 was determined for each mouse. SG-18 administration to DSS-treated mice did not alter body weight as compared to vehicle treated DSS mice. Results are shown in FIG. 35, with the graph representing data pooled from 2 individual experiments (n=20).

Figure 36:
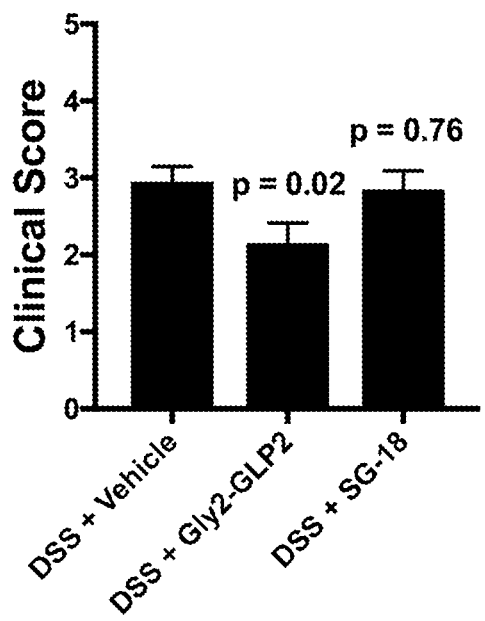
FIG. 36 shows effects of SG-18 administration on gross pathology in a DSS model of inflammatory bowel disease, as described in Example 4H.

H. Effects of SG-18 on Gross Pathology in a DSS Model of Inflammatory Bowel Disease Gross pathology observations were made in mice included in the concurrent DSS model performed in Example 4E, using the scoring system described in Example 1H above. SG-18 administration to DSS treated mice did not reduce gross pathology as compared to vehicle treated DSS mice. Results are shown in FIG. 36, with the graph representing data pooled from 2 individual experiments (n=20).

I. Effects of SG-18 on the Colon Length in a DSS Model of Inflammatory Bowel Disease The following experiment demonstrates the effects of SG-18 on colon shortening to treat in an in vivo model of inflammatory bowel disease.

Figure 37:
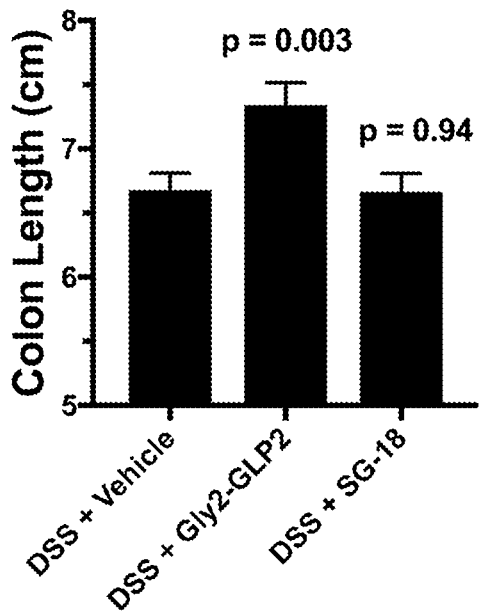
FIG. 37 shows effects of SG-18 administration on colon length in a DSS model of inflammatory bowel disease, as described in Example 4I.

Colon length was measured in mice included in the DSS model described in Example 4E. SG-18 administration to DSS treated mice did not reduce colon shortening elicited by DSS treatment. A significant improvement in colon length was observed with Gly2-GLP2 as a positive control and Gly2-GLP2 treatment had a significant improvement over SG-18. Results are shown in FIG. 37, with the graph representing data pooled from 2 individual experiments (n=20).

J. Effects of SG-18 on Colon Weight to Length Ratio in a DSS Model of Inflammatory Bowel Disease The following experiment demonstrates the effects of SG-18 as disclosed herein on changes in colon weight to length ratio induced by DSS treatment.

Figure 38:
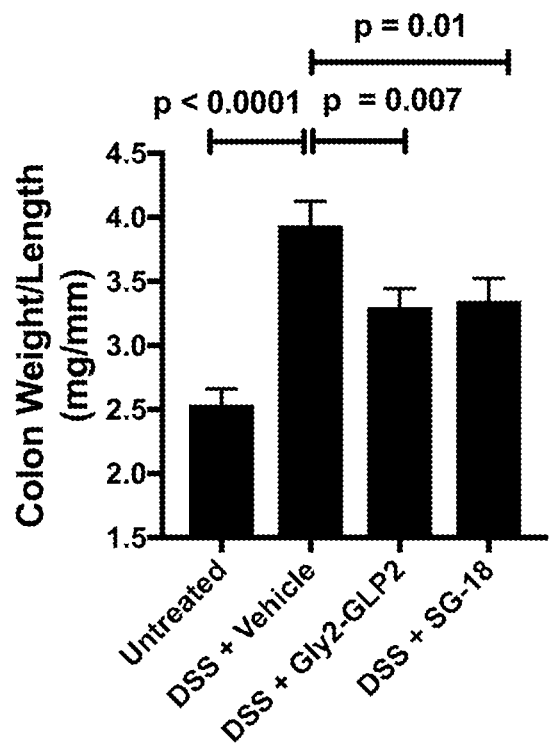
FIG. 38 shows effects of SG-18 administration on colon weight to length ratio in a DSS model of inflammatory bowel disease, as described in Example 4J.

Colon length and weight were measured in mice included in the DSS model study described in Example 4E. SG-18 administration to DSS treated mice reduced the colon weight to length ratio elicited by DSS (DSS+vehicle=3.9 and DSS+SG-18=3.3; p=0.01). A significant reduction in colon weight to length ratio was also observed with Gly2-GLP2 (p=0.007). SG-18 treatment reduced the colon weight to length ratio to a similar degree as observed for the positive control Gly2-GLP2 treatment. Results are shown in FIG. 38, with the graph representing data pooled from two individual experiments (n=20).

Table 2 describes SEQ ID NOs of the present disclosure with detailed information.

TABLE 2

| SEQ ID NO | Type | Description |
| --- | --- | --- |
| | | SG-15 |
| 1 | PRT | SG-15 protein sequence |
| 2 | DNA | coding sequence (cds) for SEQ ID NO: 1 |
| 3 | PRT | SG-15 protein sequence with "start methionine" |
| 4 | DNA | cds for SEQ ID NO: 3 |
| 5 | PRT | GenBank ACR71387 protein sequence |
| 6 | DNA | cds for SEQ ID NO: 5 |
| 7 | PRT | GenBank WP_041687898 protein sequence |
| 8 | DNA | cds for SEQ ID NO: 7 |
| | | SG-16 |
| 9 | PRT | SG-16 protein sequence |
| 10 | DNA | cds for SEQ ID NO: 9 |
| 11 | PRT | GenBank WP_012738427 protein sequence |
| 12 | DNA | cds for SEQ ID NO: 11 |
| | | SG-17 |
| 13 | PRT | SG-17 protein sequence |
| 14 | DNA | cds for SEQ ID NO: 13 |
| 15 | PRT | SG-17 protein sequence with "start methionine" |

TABLE 2-continued

| SEQ ID NO | Type | Description |
|---|---|---|
| 16 | DNA | cds for SEQ ID NO: 15 |
| 17 | PRT | GenBank WP_012740767 protein sequence |
| 18 | DNA | cds for SEQ ID NO: 17 |
| | | SG-18 |
| 19 | PRT | SG-18 protein sequence |
| 20 | DNA | cds for SEQ ID NO: 19 |
| 21 | PRT | SG-18 protein sequence with "start methionine" |
| 22 | DNA | cds for SEQ ID NO: 21 |
| 23 | PRT | GenBank SKA51491 protein sequence |
| 24 | DNA | cds for SEQ ID NO: 23 |
| 25 | PRT | GenBank WP_007286875 protein sequence |
| 26 | DNA | cds for SEQ ID NO: 25 |

NUMBERED EMBODIMENTS OF THE DISCLOSURE

Notwithstanding the appended claims, the disclosure sets forth the following numbered embodiments:

Methods of Treatment

1. A method of treating a gastrointestinal epithelial cell barrier function disorder, comprising:
   a. administering to a patient in need thereof a pharmaceutical composition, comprising:
      i. a therapeutic protein comprising an amino acid sequence having at least about 85% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25; and
      ii. a pharmaceutically acceptable carrier.
2. The method of embodiment 1, wherein the gastrointestinal epithelial cell barrier function disorder is a disease associated with decreased gastrointestinal wall integrity.
3. The method of any one of embodiments 1-2, wherein the gastrointestinal epithelial cell barrier function disorder is a disease associated with decreased gastrointestinal mucosal epithelium integrity.
4. The method of any one of embodiments 1-3, wherein the gastrointestinal epithelial cell barrier function disorder is a disease associated with decreased intestinal epithelium integrity.
5. The method of any one of embodiments 1-4, wherein the gastrointestinal epithelial cell barrier function disorder is at least one selected from the group consisting of: inflammatory bowel disease, Crohn's disease, ulcerative colitis, pouchitis, irritable bowel syndrome, enteric infections, *Clostridium difficile* infections, metabolic diseases, obesity, type 2 diabetes, non-alcoholic steatohepatitis, non-alcoholic fatty liver disease, liver disorders, alcoholic steatohepatitis, celiac disease, necrotizing enterocolitis, gastro intestinal disorders, short bowel syndrome, GI mucositis, chemotherapy induced mucositis, radiation induced mucositis, oral mucositis, interstitial cystitis, neurological disorders, cognitive disorders, Alzheimer's, Parkinson's, multiple sclerosis, autism, chemotherapy associated steatohepatitis (CASH), and pediatric versions of the aforementioned diseases.
6. The method of any one of embodiments 1-5, wherein the gastrointestinal epithelial cell barrier function disorder is inflammatory bowel disease.
7. The method of any one of embodiments 1-6, wherein the gastrointestinal epithelial cell barrier function disorder is Crohn's disease.
8. The method of any one of embodiments 1-6, wherein the gastrointestinal epithelial cell barrier function disorder is ulcerative colitis.
9. The method of any one of embodiments 1-8, wherein the therapeutic protein comprises an amino acid sequence having at least about 90% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.
10. The method of any one of embodiments 1-9, wherein the therapeutic protein comprises an amino acid sequence having at least about 95% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.
11. The method of any one of embodiments 1-10, wherein the therapeutic protein comprises an amino acid sequence having at least about 97% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.
12. The method of any one of embodiments 1-11, wherein the therapeutic protein comprises an amino acid sequence having at least about 98% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.
13. The method of any one of embodiments 1-12, wherein the therapeutic protein comprises an amino acid sequence having at least about 99% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.
14. The method of any one of embodiments 1-13, wherein the therapeutic protein comprises an amino acid sequence selected from the group consisting of: SEQ ID NO: 1, SEQ ID NO:3, SEQ ID NO:5, SEQ ID NO:7, SEQ ID NO:9, SEQ ID NO: 11, SEQ ID NO:13, SEQ ID NO: 15, SEQ ID NO:17, SEQ ID NO:19, SEQ ID NO:21, SEQ ID NO:23, or SEQ ID NO:25.
15. The method of any one of embodiments 1-14, wherein the therapeutic protein comprises the amino acid sequence of SEQ ID NO:1.
16. The method of any one of embodiments 1-15, wherein administering comprises rectal, parenteral, intravenous, topical, oral, dermal, transdermal, or subcutaneous administration.
17. The method of any one of embodiments 1-16, wherein administering is to the: mouth, gastrointestinal lumen, and/or intestines of the patient.
18. The method of any one of embodiments 1-17, wherein the patient experiences a reduction in at least one symptom associated with the gastrointestinal epithelial cell barrier function disorder.

19. The method of any one of embodiments 1-18, wherein the patient experiences a reduction in at least one symptom associated with the gastrointestinal epithelial cell barrier function disorder selected from the group consisting of: abdominal pain, blood in stool, pus in stool, fever, weight loss, frequent diarrhea, fatigue, reduced appetite, tenesmus, and rectal bleeding.

20. The method of any one of embodiments 1-19, wherein administering reduces gastrointestinal inflammation in the patient.

21. The method of any one of embodiments 1-19, wherein administering increases the production of mucin in intestinal tissue in the patient.

22. The method of any one of embodiments 1-19, wherein administering increases intestinal epithelium wound healing in the patient.

23. The method of any one of embodiments 1-22, further comprising: administering at least one second therapeutic agent to the patient.

24. The method of any one of embodiments 1-22, further comprising: administering at least one second therapeutic agent to the patient, said second therapeutic agent selected from the group consisting of: an anti-diarrheal, a 5-aminosalicylic acid compound, an anti-inflammatory agent, an antibiotic, an antibody, an anti-cytokine agent, an anti-inflammatory cytokine agent, a steroid, a corticosteroid, and an immunosuppressant.

Expression Vectors

1. An expression vector, comprising: a polynucleotide, which encodes a protein comprising an amino acid sequence having at least about 85% sequence identity to SEQ ID NO: 1, SEQ ID NO:3, SEQ ID NO:5, SEQ ID NO:7, SEQ ID NO: 9, SEQ ID NO: 11, SEQ ID NO:13, SEQ ID NO: 15, SEQ ID NO:17, SEQ ID NO:19, SEQ ID NO: 21, SEQ ID NO:23, or SEQ ID NO:25.

2. The expression vector of embodiment 1, wherein the encoded protein comprises an amino acid sequence having at least about 90% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.

3. The expression vector of any one of embodiments 1-2, wherein the encoded protein comprises an amino acid sequence having at least about 95% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO: 21, SEQ ID NO:23, or SEQ ID NO:25.

4. The expression vector of any one of embodiments 1-3, wherein the encoded protein comprises an amino acid sequence having at least about 97% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO: 21, SEQ ID NO:23, or SEQ ID NO:25.

5. The expression vector of any one of embodiments 1-4, wherein the encoded protein comprises an amino acid sequence having at least about 98% sequence identity to SEQ ID NO: 1, SEQ ID NO:3, SEQ ID NO:5, SEQ ID NO:7, SEQ ID NO: 9, SEQ ID NO: 11, SEQ ID NO:13, SEQ ID NO: 15, SEQ ID NO:17, SEQ ID NO:19, SEQ ID NO: 21, SEQ ID NO:23, or SEQ ID NO:25.

6. The expression vector of any one of embodiments 1-5, wherein the encoded protein comprises an amino acid sequence having at least about 99% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO: 21, SEQ ID NO:23, or SEQ ID NO:25.

7. The expression vector of any one of embodiments 1-6, wherein the encoded protein comprises an amino acid sequence selected from the group consisting of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25.

8. The expression vector of any one of embodiments 1-7, wherein the encoded protein comprises the amino acid sequence of SEQ ID NO:1.

Host Cells

1. A host cell, comprising: an exogenous polynucleotide which encodes a protein comprising an amino acid sequence having at least about 85% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO: 21, SEQ ID NO:23, or SEQ ID NO:25.

2. The host cell of embodiment 1, wherein the encoded protein comprises an amino acid sequence having at least about 90% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.

3. The host cell of any one of embodiments 1-2, wherein the encoded protein comprises an amino acid sequence having at least about 95% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.

4. The host cell of any one of embodiments 1-3, wherein the encoded protein comprises an amino acid sequence having at least about 97% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.

5. The host cell of any one of embodiments 1-4, wherein the encoded protein comprises an amino acid sequence having at least about 98% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.

6. The host cell of any one of embodiments 1-5, wherein the encoded protein comprises an amino acid sequence having at least about 99% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO:23, or SEQ ID NO:25.

7. The host cell of any one of embodiments 1-6, wherein the encoded protein comprises an amino acid sequence selected from the group consisting of SEQ ID NO: 1, SEQ ID NO: 3, SEQ ID NO: 5, SEQ ID NO:7, SEQ ID NO:9, SEQ ID NO:11, SEQ ID NO:13, SEQ ID NO:

15, SEQ ID NO:17, SEQ ID NO:19, SEQ ID NO:21, SEQ ID NO:23, and SEQ ID NO:25.
8. The host cell of any one of embodiments 1-7, wherein the encoded protein comprises the amino acid sequence of SEQ ID NO:1.
9. The host cell of any one of embodiments 1-8, wherein the exogenous polynucleotide further encodes a host cell specific signal sequence.
10. The host cell of any one of embodiments 1-9, wherein the exogenous polynucleotide comprises a nucleic acid sequence having at least about 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO:18, SEQ ID NO:20, SEQ ID NO:22, SEQ ID NO:24, or SEQ ID NO: 26.
11. The host cell of any one of embodiments 1-10, wherein the host cell is a prokaryotic cell.
12. The host cell of any one of embodiments 1-11, wherein the host cell is an *Escherichia coli* cell.
13. The host cell of any one of embodiments 1-10, wherein the host cell is a eukaryotic cell.
14. The host cell of any one of embodiments 1-10 and 13, wherein the host cell is a Chinese Hamster Ovary cell.
15. A method of producing a protein, comprising: culturing the host cell of any one of embodiments 1-14, under conditions sufficient for expression of the encoded protein.

Isolated Proteins and Pharmaceutical Compositions Thereof
1. An isolated protein, comprising: an amino acid sequence having at least about 85% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO: 15, SEQ ID NO:17, SEQ ID NO:19, SEQ ID NO:21, SEQ ID NO: 23, or SEQ ID NO: 25.
2. The isolated protein of embodiment 1, comprising: an amino acid sequence having at least about 90% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO: 25.
3. The isolated protein of any one of embodiments 1-2, comprising: an amino acid sequence having at least about 95% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.
4. The isolated protein of any one of embodiments 1-3, comprising: an amino acid sequence having at least about 97% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.
5. The isolated protein of any one of embodiments 1-4, comprising: an amino acid sequence having at least about 98% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.
6. The isolated protein of any one of embodiments 1-5, comprising: an amino acid sequence having at least about 99% sequence identity to SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25.
7. The isolated protein of any one of embodiments 1-6, comprising: an amino acid sequence selected from the group consisting of SEQ ID NO: 1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, and SEQ ID NO:25.
8. The isolated protein of any one of embodiments 1-7, comprising: the amino acid sequence of SEQ ID NO:1.
9. The isolated protein of any one of embodiments 1-8, wherein the protein increases electrical resistance in an in vitro transepithelial electrical resistance assay.
10. The isolated protein of any one of embodiments 1-9, wherein the protein increases electrical resistance in an in vitro transepithelial electrical resistance assay by at least about 5%, 10%, 20%, 30%, 40%, 50%, 60%, 70%, 80%, 90%, 95%, or 99%, as compared to the assay performed in the absence of the protein.
11. The isolated protein of any one of embodiments 1-10, wherein the protein increases electrical resistance in an in vitro transepithelial electrical resistance assay, as compared to a control of a kinase inhibitor.
12. The isolated protein of any one of embodiments 1-11, wherein the protein increases electrical resistance in an in vitro transepithelial electrical resistance assay, as compared to a control of staurosporine or myosin light chain kinase.
13. A pharmaceutical composition, comprising:
   a. the isolated protein of any one of embodiments 1-12; and
   b. a pharmaceutically acceptable carrier.
14. The pharmaceutical composition of any one of embodiments 1-13, wherein the protein comprises the amino acid sequence of SEQ ID NO:1.
15. The pharmaceutical composition of any one of embodiments 1-14, formulated for rectal, parenteral, intravenous, topical, oral, dermal, transdermal, or subcutaneous administration.
16. The pharmaceutical composition of any one of embodiments 1-15, formulated such that the protein has activity in the gastrointestinal lumen and/or intestines of the patient.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

Molodecky et al. 2012, Increasing incidence and prevalence of the inflammatory bowel diseases with time, based on systematic review, Gastroenterology 142(1): 46-54.

Aroniadis et al., 2013, Fecal microbiota transplantation: past, present and future, Curr. Opin. Gastroenterol. 29(1): 79-84.

Maloy et al., 2011, Intestinal homeostasis and its breakdown in inflammatory bowel disease, Nature 474(7351): 298-306.

Needleman et al., 1970, A general method applicable to the search for similarities in the amino acid sequence of two proteins J. Mol. Biol., 48(3): 444-453.

Myers et al., 1988, Optimal alignments in linear space, CABIOS 4: 11-17.

Altschul, et al., 1990, Basic local alignment search tool, J. Mol. Biol. 215: 403-410.

Altschul et al., 1997, Gapped BLAST and PSI-BLAST: a new generation of protein database search programs, Nucleic Acids Res. 25(17): 3389-3402.

Henikoff et al., 1992, Amino acid substitution matrices from protein blocks, Proc. Natl. Acad. Sci. 89(22): 10915-10919.

Karlin et al., 1993, Applications and statistics for multiple high-scoring segments in molecular sequences, Proc. Natl. Acad. Sci. 90: 5873-5877.

Higgins et al., 1988, CLUSTAL: a package for performing multiple sequence alignment on a microcomputer, Gene 73: 237-244.

Person et al., 1988, Improved tools for biological sequence comparison, Proc. Natl. Acad. Sci. 85: 2444-2448.

Bowie et al., 1990, Deciphering the message in protein sequences: tolerance to amino acid substitutions, Science 247: 1306-1310.

IUPAC Commission on the Nomenclature of Organic Chemistry (CNOC) and IUPAC-IUB Commission on Biochemical Nomenclature (CBN), 1975, Nomenclature of α-Amino Acids, (Recommendations 1974), Biochemistry 14: 449-462.

Remington's Pharmaceutical Sciences, 17th edition, Alfonso R. Gennaro (Ed.), Mark Publishing Company, Easton, PA, USA, 1985.

Encyclopaedia of Pharmaceutical Technology, 3rd edition, James Swarbrick (Ed.), Informa Healthcare USA (Inc.), NY, USA, 2007.

Berge et al., 1977, Pharmaceutical salts, J. Pharm. Sci. 66: 1-19.

Handbook of Pharmaceutical Salts: Properties, Selection, and Use, Stahl and Wermuth, Wiley-VCH, 2002.

In re Bergstrom, 427 F.2d 1394, (CCPA 1970)

In re Bergy, 596 F.2d 952 (CCPA 1979)

Parke-Davis & Co. v. HK. Mulford & Co., 189 F. 95 (S.D.N.Y. 1911) aff'd in part, rev'd in part, 196 F. 496 (2d Cir. 1912)

Merck & Co., Inc., v. Olin Mathieson Chemical Corporation, 253 F.2d 156 (4th Cir. 1958)

Horhota et al., 2006, Glycerol nucleoside triphosphates: Synthesis and polymerase substrate activities, Organic Letters 8: 5345-5347.

Botoman et al., 1998, Management of Inflammatory Bowel Disease, Am. Fam. Physician, 57(1): 57-68.

Neurath, 2014, Cytokines in Inflammatory Bowel Disease, Nature Reviews Immunology 14: 329-342.

Zhang et al., 2007, Cytokines, Inflammation and Pain, Int. Anesthesiol. Clin. 45(2): 27-37.

Strober et al., Proinflammatory cytokines in the pathogenesis of inflammatory bowel diseases, Gastroenterology 140 (6): 1756-1767.

Boltin et al., 2013, Mucin Function in Inflammatory Bowel Disease: An Update, J. Clin. Gastroenterol. 47(2):106-111.

Kim et al., 2012, Investigating Intestinal Inflammation in DSS-induced Model of IBD, Journal of Visualized Experiments, 60: 2-6.

Levesque et al., 2015 Converging goals of treatment of inflammatory bowel disease from clinical trials and practice, Gastroenterology 148: 37-51.

Best et al., 1976, Development of a Crohn's disease activity index. National Cooperative Crohn's Disease Study, Gastroenterol. 70: 439-444.

Johansson, et al., 2014, Bacteria penetrate the normally impenetrable inner colon mucus layer in both murine colitis models and patients with ulcerative colitis, Gut 63:281-291.

Simmonds et al., 2014, Paneth cell metaplasia in newly diagnosed inflammatory bowel disease in children, BMC Gastroenterol. 14:93.

Gassler et al., 2001, Inflammatory bowel disease is associated with changes of enterocytic junctions, Am. J. Physiol. Gastrointest. Liver Physiol. 281:G216-G228.

Dewi, et al., 2004, In vitro assessment of human endothelial cell permeability: effects of inflammatory cytokines and dengue virus infection. J. Virol. Methods. 121: 171-180.

Mandic, et al., 2004, Evaluation of head and neck squamous cell carcinoma invasiveness by the electrical resistance breakdown assay, Clin. Exp. Metast. 21: 699-704.

Dewi, et al., 2008, Peripheral blood mononuclear cells increase the permeability of dengue virus-infected endothelial cells in association with down-regulation of vascular endothelial cadherin, J. Gen. Virol. 89:642-652.

Sands, 2004, From symptom to diagnosis: clinical distinctions among various forms of intestinal inflammation, Gastroenterology 126: 1518-1532.

Danese et al., 2006, Etiopathogenesis of inflammatory bowel diseases, World J. Gastroenterol. 12: 4807-4812.

Duncan, S. H., Aminov, R. I., Scott, K. P., Louis, P., Stanton, T. B., Flint, H. J. (2006). Proposal of *Roseburia faecis* sp. nov., *Roseburia hominis* sp. nov. and *Roseburia inulinivorans* sp. nov., based on isolates from human faeces. *Int. J. Syst. Evol. Microbiol*. Vol. 56, pgs. 2437-2441.

International Human Genome Sequencing Consortium (2004) Finishing the euchromatic sequence of the human genome. Nature. 431, 931-45.

Jensen O. N. (2004) Modification-specific proteomics: Characterization of post-translational modifications by mass spectrometry. Curr Opin Chem Biol. 8, 33-41.

Ayoubi T. A. and Van De Ven W. J. (1996) Regulation of gene expression by alternative promoters. FASEB J. 10, 453-60.

Walsh C. (2006) Posttranslational modification of proteins: Expanding nature's inventory. Englewood, Colo.: Roberts and Co. Publishers. xxi, 490 p. p.

Gaston B. M. et al. (2003) S-nitrosylation signaling in cell biology. Mol Interv. 3, 253-63.

Jaffrey S. R. and Snyder S. H. (2001) The biotin switch method for the detection of S-nitrosylated proteins. Sci STKE. 2001, pl1.

Han P. and Chen C. (2008) Detergent-free biotin switch combined with liquid chromatography/tandem mass spectrometry in the analysis of S-nitrosylated proteins. Rapid Commun Mass Spectrom. 22, 1137-45.

Imai S. et al. (2000) Transcriptional silencing and longevity protein SIR2 is an NAD-dependent histone deacetylase. Nature. 403, 795-800.

Glozak M. A. et al. (2005) Acetylation and deacetylation of non-histone proteins. Gene. 363, 15-23.

Yang X. J. and Seto E. (2008) Lysine acetylation: Codified crosstalk with other posttranslational modifications. Mol Cell. 31, 449-61.

Bratt, et al., "A phase 1 trial with transgenic bacteria expressing interleukin-10 in Crohn's disease," Clinical Gastroenterology and Hepatology, 2006, Vol. 4, pgs. 754-759.

Shigemori, et al., "Oral delivery of *Lactococcus lactis* that secretes bioactive heme oxygenase-1 alleviates development of acute colitis in mice," Microbial Cell Factories, 2015, Vol. 14:189.

Steidler, et al., "Treatment of murine colitis by *Lactococcus lactis* secreting interleukin-10," Science, 2000, Vol. 289, pgs. 1352-1355.

Hanniffy, et al., "Mucosal delivery of a pneumococcal vaccine using *Lactococcus lactis* affords protection against respiratory infection," Journal of Infectious Diseases, 2007, Vol. 195, pgs. 185-193.

Vandenbroucke, et al., "Active delivery of trefoil factors by genetically modified *Lactococcus lactis* prevents and heals acute colitis in mice," Gastroenterology, 2004, Vol. 127, pgs. 502-513.

Sheth, et al., "Manipulating bacterial communities by in situ microbiome engineering," Trends in Genetics, 2016, Vol. 32, Issue 4, pgs. 189-200.

Lerner et al., "Dysbiosis may trigger autoimmune diseases via inappropriate post-translational modification of host proteins," Frontiers in Microbiology, 2016, Vol. 7, Article 84.

Shawki, A., and D. F. McCole. 2017. Mechanisms of Intestinal Epithelial Barrier Dysfunction by Adherent-Invasive *Escherichia coli*. Cell Mol Gastroenterol Hepatol 3: 41-50.

What is claimed is:

1. A pharmaceutical composition, comprising:
  i) a protein comprising an amino acid sequence having at least about 95% sequence identity to SEQ ID NO:1, SEQ ID NO:9, SEQ ID NO:13, or SEQ ID NO:19; and
  ii) a pharmaceutically acceptable carrier,
    wherein the protein comprises at least one post translational modification.

2. The pharmaceutical composition of claim 1, wherein the protein comprises an amino acid sequence having at least about 97% sequence identity to SEQ ID NO: 1, SEQ ID NO:9, SEQ ID NO: 13, or SEQ ID NO: 19.

3. The pharmaceutical composition of claim 1, wherein the protein comprises an amino acid sequence having at least about 98% sequence identity to SEQ ID NO: 1, SEQ ID NO:9, SEQ ID NO: 13, or SEQ ID NO: 19.

4. The pharmaceutical composition of claim 1, wherein the protein comprises an amino acid sequence having at least about 99% sequence identity to SEQ ID NO: 1, SEQ ID NO:9, SEQ ID NO: 13, or SEQ ID NO: 19.

5. The pharmaceutical composition of claim 1, wherein the protein comprises SEQ ID NO: 1, SEQ ID NO:9, SEQ ID NO: 13, or SEQ ID NO: 19.

6. The pharmaceutical composition of claim 1, wherein the protein comprises the amino acid sequence of SEQ ID NO: 1.

7. The pharmaceutical composition of claim 1, wherein the protein comprises the amino acid sequence of SEQ ID NO: 9.

8. The pharmaceutical composition of claim 1, wherein the protein comprises the amino acid sequence of SEQ ID NO: 13.

9. The pharmaceutical composition of claim 1, wherein the protein comprises the amino acid sequence of SEQ ID NO: 19.

10. The pharmaceutical composition of claim 1, wherein the pharmaceutical composition is formulated for rectal, parenteral, intravenous, topical, oral, dermal, transdermal, or subcutaneous administration.

11. The pharmaceutical composition of claim 1, wherein the at least one post translational modification is pegylation.

12. The pharmaceutical composition of claim 1, wherein the at least one post translational modification is glycosylation, ubiquitination, nitrosylation, methylation, acetylation, or lipidation.

13. The pharmaceutical composition of claim 1, wherein the at least one post translational modification is phosphorylation, glycosylation, ubiquitination, nitrosylaton, methylation, acetylation, or lipidation.

14. The pharmaceutical composition of claim 1, wherein the pharmaceutical composition is formulated such that the protein has activity in a gastrointestinal lumen and/or intestines of a patient to which the pharmaceutical composition is administered.

15. The pharmaceutical composition of claim 1, wherein the pharmaceutical composition further comprises a second therapeutic agent.

16. The pharmaceutical composition of claim 15, wherein the second therapeutic agent is selected from the group consisting of an anti-diarrheal, a 5-aminosalicylic acid compound, an anti-inflammatory agent, an antibiotic, an anti-cytokine agent, an anti-inflammatory cytokine agent, a steroid, a corticosteroid, an immunosuppressant, a JAK inhibitor, an anti-integrin biologic, an anti-IL12/23R biologic, a vitamin, and a protease inhibitor.

17. The pharmaceutical composition of claim 16, wherein the second therapeutic agent is a protease inhibitor.

18. The pharmaceutical composition of claim 17, wherein the protease inhibitor inhibits degradation of the protein in the presence of fecal matter and/or blood.

* * * * *

```
SEQUENCE LISTING

Sequence total quantity: 26
SEQ ID NO: 1              moltype = AA   length = 400
FEATURE                   Location/Qualifiers
source                    1..400
                          mol_type = protein
                          organism = Eubacterium eligens
SEQUENCE: 1
EYTEIRTASE LVEAAKSASG NYKLMTDIDM TGVEWTPWDF SGTFDGNGHS ILNLSVKTVS   60
KKTMKTYDGN RKEYKTYGAG FFGVLTGAKV TGLDIYGARI EITTTEPCFA APIAGLADDS  120
DISDCIIKDT YVSLTDSAKM WGTGGIAGFG SGNLDNITTD VTLVCVDTDA AVRDEQFMGG  180
AYAAGFLNIR NCSITIDGYD SDHGYVHDGG LVGMYMVYPL ELSKTYQGEV LNNKVKGMIT  240
FFEDNTDRRA YCQANMGEVM NWTYAYSGFT SDFKRNETYD YSVTLLPEMC SNPSYTDVVT  300
EATASDFGYT THTCSTCGYT YSDTYTIHEH KVDSYSVVKE AASTDKKDGI EAGTCSLCNQ  360
TVYREYAANV VTDDNTQATD NKASGTAVKK GMKESTAVFA                       400

SEQ ID NO: 2              moltype = DNA   length = 1200
FEATURE                   Location/Qualifiers
source                    1..1200
                          mol_type = other DNA
                          organism = Eubacterium eligens
SEQUENCE: 2
gaatacacag aaatccgaac agcgtcagaa cttgtggaag cagctaagag tgcgtcagga    60
aattataaac tgatgacaga tatagatatg acaggagttg agtggacgcc atgggatttt   120
tcgggaacat ttgacggtaa cggacacagc atacttaacc tgtcagtaaa gacagtaagc   180
aagaagacaa tgaagaccta tgacggcaac agaaaagagt acaaaacata cggcgcaggc   240
ttctttgggg tgcttacagg tgcgaaagta acaggactgg atatatatgg agcaagaatt   300
gagattacta caacggaacc atgttttgcg gcaccaatag cagggcttgc agacgacagc   360
gacatatcag actgtataat taaggataca tatgtgtcac tcacagattc agctaaaatg   420
tgggaaacag gcggaatcgc tggattttga agcggcaatc ttgataatat tactacagat   480
gtgacacttg tatgtgtaga tacagacgca gcggtcaggg acgagcagtt catgggaggc   540
gcgtatgcag caggtttcct taatataagg aattgttcta taacaataga tggatatgat   600
tcagaccacg gatatgtgca tgatggcgga cttgtcggca tgtatatggt atatccattg   660
gaactgtcaa agacatatca gggcgaagtg cttaacaaca aagttaaggg aatgataaca   720
tttttcgaag acaatacaga ccgccgtgca tactgtcagg caaatatggg tgaggtcatg   780
aactggacat atgcatattc aggcttcaca tcagatttta agagaaatga gacatatgat   840
tattcagtga cactgcttcc ggaaatgtgc agcaatcctt catacacaga tgtagtgaca   900
gaagcaacag catcagactt tggatacaca acacacacct gcagtacatg tggctacaca   960
tattcagaca cttacacaat acatgagcat aaggtcgaca gttacagcgt ggtaaaggaa  1020
gcagccagca cagacaagaa agacggaata gaggcaggaa catgcagcct gtgcaatcag  1080
acagtttaca gggaatatgc tgcaaatgta gtaacgacg ataatacaca ggcaacagac   1140
aataaagcat caggcacggc tgtcaaaaaa ggaatgaaag aaagtacagc agtatttgca  1200

SEQ ID NO: 3              moltype = AA   length = 401
FEATURE                   Location/Qualifiers
source                    1..401
                          mol_type = protein
                          organism = Eubacterium eligens
SEQUENCE: 3
MEYTEIRTAS ELVEAAKSAS GNYKLMTDID MTGVEWTPWD FSGTFDGNGH SILNLSVKTV   60
SKKTMKTYDG NRKEYKTYGA GFFGVLTGAK VTGLDIYGAR IEITTTEPCF AAPIAGLADD  120
SDISDCIIKD TYVSLTDSAK MWGTGGIAGF GSGNLDNITT DVTLVCVDTD AAVRDEQFMG  180
GAYAAGFLNI RNCSITIDGY DSDHGYVHDG GLVGMYMVYP LELSKTYQGE VLNNKVKGMI  240
TFFEDNTDRR AYCQANMGEV MNWTYAYSGF TSDFKRNETY DYSVTLLPEM CSNPSYTDVV  300
TEATASDFGY TTHTCSTCGY TYSDTYTIHE HKVDSYSVVK EAASTDKKDG IEAGTCSLCN  360
QTVYREYAAN VVTDDNTQAT DNKASGTAVK KGMKESTAVF A                     401
```

| SEQ ID NO: 4 | moltype = DNA   length = 1203 | |
|---|---|---|
| FEATURE | Location/Qualifiers | |
| source | 1..1203 | |
| | mol_type = other DNA | |
| | organism = Eubacterium eligens | |

SEQUENCE: 4

```
atggaataca cagaaatccg aacagcgtca gaacttgtgg aagcagctaa gagtgcgtca   60
ggaaattata aactgatgac agatatagat atgacaggag ttgagtggac gccatgggat  120
ttttcgggaa catttgacgg taacggacac agcatactta acctgtcagt aaagacagta  180
agcaagaaga caatgacggc ctatgacggc aacagaaaag agtacaaaac atacggcgca  240
ggcttctttg gggtgcttac aggtgcgaaa gtaacaggac tggatatata tggagcaaga  300
attgagatta ctacaacgga accatgtttt gcggcaccaa tagcagggct tgcagacgac  360
agcgacatat cagactgtat aattaaggat acatatgtgt cactcacaga ttcagctaaa  420
atgtgggggaa caggcggaat cgctggagtt ggaagcggaa atcttgataa tattactaca  480
gatgtgacac ttgtatgtgt agatacagac gcagcggtca gggacgagca gttcatggga  540
ggcgcgtatg cagcaggttt ccttaatata aggaattgtt ctataacaat agatggatat  600
gattcagacc acggatatgt gcatgatggc ggacttgtcg catgtatat ggtatatcca  660
ttggaactgt caaagacata tcagggcgaa gtgcttaaca acaaagttaa gggaatgata  720
acatttttcg aagacaatac agaccgccgt gcatactgtc aggcaaatat gggtgaggtc  780
atgaactgga catatgcata ttcaggcttc acatcagatt ttaagagaaa tgagacatat  840
gattattcag tgacactgct tccggaaatg tgcagcaatc cttcatacac agatgtagtg  900
acagaagcaa cagcatcaga cttttggatac acaacacaca cctgcagtac atgtggctac  960
acatattcag acacttacac aatacatgag cataaggtcg acagttacag cgtggtaaag 1020
gaagcagcca gcacagacaa gaaagacgga atagaggcag gaacatgcag cctgtgcaat 1080
cagacagttt acagggaata tgctgcaaat gtagtaacag acgataatac acaggcaaca 1140
gacaataaag catcaggcac ggctgtcaaa aaaggaatga agaaagtac agcagtattt 1200
gca                                                                1203
```

| SEQ ID NO: 5 | moltype = AA   length = 494 | |
|---|---|---|
| FEATURE | Location/Qualifiers | |
| source | 1..494 | |
| | mol_type = protein | |
| | organism = Eubacterium eligens | |

SEQUENCE: 5

```
MRYNQTAKDA NISEERGIKM FNKSIIKKAA AIAAVILAVT ALPTNMTKAD TQTSGSTVSQ   60
TTSEYTEIRT ASELVEAAKS ASGNYKLMTD IDMTGVEWTP WDFSGTFDGN GHSILNLSVK  120
TVSKKTMKTY DGNRKEYKTY GAGFFGVLTG AKVTGLDIYG ARIEITTTEP CFAAPIAGLA  180
DDSDISDCII KDTYVSLTDS AKMWGTGGIA GFGSGNLDNI TTDVTLVCVD TDAAVRDEQF  240
MGGAYAAGFL NIRNCSITID GYDSDHGYVH DGGLVGMYMV YPLELSKTYQ GEVLNNKVKG  300
MITFFEDNTD RRAYCQANMG EVMNWTYAYS GFTSDFKRNE TYDYSVTLLP EMCSNPSYTD  360
VVTEATASDF GYTHTCSTC GYTYSDTYTI HEHKVDSYSV VKEAASTDKK DGIEAGTCSL  420
CNQTVYREYA ANVVTDDNTQ ATDNKASGTA VKKGMKESTA VFAVILVVIV IVIIITVVMM  480
VQNNKRKRRY NRRR                                                    494
```

| SEQ ID NO: 6 | moltype = DNA   length = 1482 | |
|---|---|---|
| FEATURE | Location/Qualifiers | |
| source | 1..1482 | |
| | mol_type = other DNA | |
| | organism = Eubacterium eligens | |

SEQUENCE: 6

```
ttgcgttata atcagacagc gaaagatgca aatatatcag aagaaagagg cataaaaatg   60
tttaataaat caattataaa aaaggcagcg gcgatagcag cagtaatact tgcagtgaca  120
gcacttccga ctaatatgac gaaggcagat acacaaacat caggaagtac cgtaagccag  180
acaacatcag aatacacaga aatccgaaca gcgtcagaac ttgtggaagc agctaagagt  240
gcgtcaggaa attataaact gatgacagat atagatatga caggagttga gtggacgcca  300
tgggattttt cgggaacatt tgacggtaac ggacacagca tacttaacct gtcagtaaag  360
acagtaagca agaagacaat gaagacctat gacggcaaca gaaaagagta caaaacatac  420
ggcgcaggct ctttggggt gcttacaggt gcgaaagtaa caggactgga tatatatgga  480
gcaagaattg agattactac aacggaacca tgttttgcgg caccaatagc agggcttgca  540
gacgacagcg acatatcaga ctgtataatt aaggatacat atgtgtcact cacagattca  600
gctaaaatgt ggggaacagg cggaatcgct ggagtttggaa gcgcaatct tgataatatt  660
actacagatg tgacacttgt atgtgtagat acagacgcag cggtcaggga cgagcagttc  720
atgggaggcg cgtatgcagc aggtttcctt aatataagga attgttctat aacaatagat  780
ggatatgatt cagaccacgg atatgtgcat gatggcggac ttgtcgcatg tatatggtat  840
atccattgg aactgtcaaa gacatatcag ggcgaagtgc ttaacaacaa agttaaggga  900
atgataacat tttcgaaga acatacagac cgccgtgcat actgtcaggc aaatatgggt  960
gaggtcatga actggacata tgcatattca ggcttcacat cagattttaa agaaaatgag 1020
acatatgatt attcagtgac actgcttccg gaaatgtgca gcaatcctca atacacagat 1080
gtagtgacag aagcaacagc atcagacttt ggatacacaa cacacacctg cagtacatgt 1140
ggctacacat attcagacac ttacacaata catgagcata aggtcgacag ttacagcgtg 1200
gtaaaggaag cagccagcac agacaagaaa gacggaatag aggcaggaac atgcagcctg 1260
tgcaatcaga cagtttacag ggaatatgct gcaaatgtag taacagacga ataatacacag 1320
gcaacagaca ataaagcatc aggcacggct gtcaaaaaag gaatgaaaga agtacagca 1380
gtatttgcag taatattggt ggtaatagtt attgtaataa ttataacagt agtcatgatg 1440
gtacagaata taaaagaaa aagagatat aacgacgcga ga                      1482
```

| SEQ ID NO: 7 | moltype = AA   length = 475 | |
|---|---|---|
| FEATURE | Location/Qualifiers | |
| source | 1..475 | |

```
                              mol_type = protein
                              organism = Eubacterium eligens
SEQUENCE: 7
MFNKSIIKKA AAIAAVILAV TALPTNMTKA DTQTSGSTVS QTTSEYTEIR TASELVEAAK      60
SASGNYKLMT DIDMTGVEWT PWDFSGTFDG NGHSILNLSV KTVSKKTMKT YDGNRKEYKT     120
YGAGFFGVLT GAKVTGLDIY GARIEITTTE PCFAAPIAGL ADDSDISDCI IKDTYVSLTD     180
SAKMWGTGGI AGFGSGNLDN ITTDVTLVCV DTDAAVRDEQ FMGGAYAAGF LNIRNCSITI     240
DGYDSDHGYV HDGGLVGMYM VYPLELSKTY QGEVLNNKVK GMITFFEDNT DRRAYCQANM     300
GEVMNWTYAY SGFTSDFKRN ETYDYSVTLL PEMCSNPSYT DVVTEATASD FGYTTHTCST     360
CGYTYSDTYT IHEHKVDSYS VVKEAASTDK KDGIEAGTCS LCNQTVYREY AANVVTDDNT     420
QATDNKASGT AVKKGMKEST AVFAVILVVI VIVIIITVVM MVQNNKRKRR YNRRR          475

SEQ ID NO: 8                  moltype = DNA   length = 1425
FEATURE                       Location/Qualifiers
source                        1..1425
                              mol_type = other DNA
                              organism = Eubacterium eligens
SEQUENCE: 8
atgtttaata aatcaattat aaaaaaggca gcggcgatag cagcagtaat acttgcagtg      60
acagcacttc cgactaatat gacgaaggca gatacacaaa catcaggaag taccgtaagc     120
cagacaacat cagaatacac agaaatccga acagcgtcag aacttgtgga agcagctaag     180
agtgcgtcag gaaattataa actgatgaca gatatagata tgacaggagt tgagtggacg     240
ccatgggatt tttcgggaac atttgacggt aacggacaca gcatacttaa cctgtcagta     300
aagacagtaa gcaagaagac aatgaagacc tatgacggca acagaaaaga gtacaaaaca     360
tacggcgcag gcttctttgg ggtgcttaca ggtgcgaaag taacaggact ggatatatat     420
ggagcaagaa ttgagattac tacaacgaaa ccatgttttg cggcaccaat agcagggctt     480
gcagacgaca gcgacatatc agactgtata attaaggata catatgtgtc actcacagat     540
tcagctaaaa tgtggggaac aggcggaatc gctggatttg gaagcggcaa tcttgataat     600
attactacag atgtgacact tgtatgtgta gatacagacg cagcggtcag ggacgagcag     660
ttcatgggag gcgcgtatgc agcaggtttc cttaatataa ggaattgttc tataacagat     720
gatggatatg attcagacca cggatatgtg catgatggcg gacttgtcgg catgtatatg     780
gtatatccat ggaactgtc aaagacatat cagggcgaag tgcttaacaa caaagttaag     840
ggaatgataa cattttttga agacaataca gaccgccgtg catactgtca ggcaaatatg     900
ggtgaggtca tgaactggac atatgcatat tcaggcttca catcagattt taagagaaat     960
gagacatatg attattcagt gacactgctt ccggaaatgt gcagcaatcc ttcatacaca    1020
gatgtagtga cagaagcaac agcatcagac tttggataca aacacacac ctgcagtaca    1080
tgtggctaca catattcaga cacttacaca atacatgagc ataaggtcga cagttacagc    1140
gtggtaaagg aagcagccag cacagacaag aaagacggaa tagaggcagg aacatgcagc    1200
ctgtgcaatc agacagttta cagggaatat gctgcaaatg tagtaacaga cgataacaa    1260
caggcaacag acaataaagc atcaggcacg gctgtcaaaa aaggaatgaa agaaagtaca    1320
gcagtatttg cagtaatatt ggtggtaata gttattgtaa taattataac agtagtcatg    1380
atggtacaga taataaaag aaaaagaaga tataacgac gcaga                      1425

SEQ ID NO: 9                  moltype = AA   length = 119
FEATURE                       Location/Qualifiers
source                        1..119
                              mol_type = protein
                              organism = Eubacterium eligens
SEQUENCE: 9
MTGCSGSKEP DNKTSVDYTV VENADLPEEL KKLIESKKDK VMRLTYTTKD YTYVVAGYGT      60
RETSGYSIKV NDVYTGDNAL YIDLNLIGPA AGEAVNEVET YPVIVLKMER REESVVFKM     119

SEQ ID NO: 10                 moltype = DNA   length = 357
FEATURE                       Location/Qualifiers
source                        1..357
                              mol_type = other DNA
                              organism = Eubacterium eligens
SEQUENCE: 10
atgacagggt gttctggcag caaagagcca gataataaga ccagtgttga ttatacagtg      60
gttgaaaatg cagacctgcc ggaagagctt aagaagctta ttgaaagcaa aaagataaa     120
gtgatgaggc ttacatacac gactaaggat tatacatatg ttgtggccgg ttatggaaca     180
agggaaacaa gtggatattc aattaaggta aatgatgtat acacaggaga taatgcacta     240
tacattgatc ttaatctgat aggtccggca gcggggggaag ctgtaaatga ggttgagaca    300
tatccggtaa tagtgcttaa gatggaaaga cgtgaagaaa gcgttgtttt taaaatg        357

SEQ ID NO: 11                 moltype = AA   length = 143
FEATURE                       Location/Qualifiers
source                        1..143
                              mol_type = protein
                              organism = Eubacterium eligens
SEQUENCE: 11
MCGKLWGKVV TVVLALLIIM PACAMTGCSG SKEPDNKTSV DYTVVENADL PEELKKLIES      60
KKDKVMRLTY TTKDYTYVVA GYGTRETSGY SIKVNDVYTG DNALYIDLNL IGPAAGEAVN     120
EVETYPVIVL KMERREESVV FKM                                             143

SEQ ID NO: 12                 moltype = DNA   length = 429
FEATURE                       Location/Qualifiers
source                        1..429
                              mol_type = other DNA
```

```
                              organism = Eubacterium eligens
SEQUENCE: 12
atgtgtggga aattatgggg aaaagttgtg actgttgtgt tggcattgct gataattatg      60
cctgcgtgtg caatgacagg gtgttctggc agcaaagagc cagataataa gaccagtgtt    120
gattatacag tggttgaaaa tgcagacctg ccggaagagc ttaagaagct tattgaaagc    180
aaaaaagata aagtgatgag gcttacatac acgactaagg attatacata tgttgtggcc    240
ggttatggaa caagggaaac aagtggatat tcaattaagg taaatgatgt atacacagga    300
gataatgcac tatacattga tcttaatctg ataggtccgg cagcggggga agctgtaaat    360
gaggttgaga catatccggt aatagtgctt aagatggaaa gacgtgaaga aagcgttgtt    420
tttaaaatg                                                             429

SEQ ID NO: 13           moltype = AA  length = 327
FEATURE                 Location/Qualifiers
source                  1..327
                        mol_type = protein
                        organism = Eubacterium eligens
SEQUENCE: 13
CNSKIDVKYD YNVEDYVQLG QYENISVQVD KTSIENELIE SKIKQDVEDN TTYTEVDRGA     60
IASDQILVTY TATSSGASLS GLTNTDGKTM ILGTDTLGLE LDELDQALYG MTPGQTKILI    120
VDIPEDYSSD LYKGTRVVFE LTMQTVAQAN VPMITNAYVK EAFGYDTVEE YRQSIKESLE    180
TDINSKVENK IQEDVLSSLQ DTFKISSYPD SLMEETRSRL ETSIGFYADF SNLSKDEYCQ    240
KQYGLSFDDF VKKSVVQQLI MEAIVKDRNM TMREYDYKGS LDDFAADNGY SNADTFVEKF    300
GKDKIVKAML VQKAQDYVIE HANISYK                                        327

SEQ ID NO: 14           moltype = DNA  length = 981
FEATURE                 Location/Qualifiers
source                  1..981
                        mol_type = other DNA
                        organism = Eubacterium eligens
SEQUENCE: 14
tgtaatagta agattgatgt taagtatgat tataatgttg aagattatgt tcagcttgga     60
cagtatgaaa acatatcagt ccaggtagat aaaacttcaa tagagaatga acttatagag    120
agtaaaatta acaggatgt agaagataat actacttata cagaagttga cagaggtgcg    180
atagcttctg atcagattct tgttacatat actgctacat cttcaggcgc atctcttagc    240
ggacttacta atacagatgg taaaacaatg attcttggaa cggatactct cggacttgaa    300
cttgatgagt tagatcaggc tttatatggt atgaccccag gtcagacaaa gatacttatt    360
gttgatatac ctgaggatta tagttcggat ttatataagg gcacgagggt tgtatttgaa    420
cttacaatgc agacagttgc acaggcaaat gttccaatga taactaatgc atatgttaag    480
gaagcgtttg gatatgatac cgttgaagaa tatagacagt caataaagga atctcttgaa    540
actgatatta attcaaaggt tgagaacaag atacaggaag atgtattatc ttctttacag    600
gatacattca agataagcag ttatcctgat tcacttatgg aagaaacaag atccagactt    660
gaaacatcta ttggtttcta tgcggatttt tcaaatcttt caaggatgaa atactgtcag    720
aagcagtatg gactttcttt tgatgacttt gttaagaaat ctgttgtaca gcagcttatt    780
atggaggcta tagttaaaga ccgcaatatg acaatgagag aatacgatta taaaggttct    840
cttgatgatt ttgcggcaga taatggatat tctaatgcgg atacatttgt tgaaaaattc    900
ggaaaagata agattgtaaa ggctatgctt gtgcagaagg cacaggatta tgttattgag    960
catgccaata tttcttataa g                                              981

SEQ ID NO: 15           moltype = AA  length = 328
FEATURE                 Location/Qualifiers
source                  1..328
                        mol_type = protein
                        organism = Eubacterium eligens
SEQUENCE: 15
MCNSKIDVKY DYNVEDYVQL GQYENISVQV DKTSIENELI ESKIKQDVED NTTYTEVDRG     60
AIASDQILVT YTATSSGASL SGLTNTDGKT MILGTDTLGL ELDELDQALY GMTPGQTKIL    120
IVDIPEDYSS DLYKGTRVVF ELTMQTVAQA NVPMITNAYV KEAFGYDTVE EYRQSIKESL    180
ETDINSKVEN KIQEDVLSSL QDTFKISSYP DSLMEETRSR LETSIGFYAD FSNLSKDEYC    240
QKQYGLSFDD FVKKSVVQQL IMEAIVKDRN MTMREYDYKG SLDDFAADNG YSNADTFVEK    300
FGKDKIVKAM LVQKAQDYVI EHANISYK                                       328

SEQ ID NO: 16           moltype = DNA  length = 984
FEATURE                 Location/Qualifiers
source                  1..984
                        mol_type = other DNA
                        organism = Eubacterium eligens
SEQUENCE: 16
atgtgtaata gtaagattga tgttaagtat gattataatg ttgaagatta tgttcagctt     60
ggacagtatg aaaacatatc agtccaggta gataaaactt caatagaaga tgaacttata    120
gagagtaaaa ttaaacagga tgtagaagat aatactactt atacagaagt tgacagaggt    180
gcgatagctt ctgatcagat tcttgttaca tatactgcta catcttcagg cgcatctctt    240
agcggactta ctaatacaga tggtaaaaca atgattcttg gaacggatac tctcggactt    300
gaacttgatg agttagatca ggctttatat ggtatgaccc caggtcagac aaagatactt    360
attgttgata tacctgagga ttatagttcg gatttatata agggcacgag ggttgtattt    420
gaacttacaa tgcagacagt gcacaggcaa atgttccaa tgataactaa tgcatatgtt    480
aaggaagcgt ttggatatga taccgttgaa gaatatagac agtcaataaa ggaatctctt    540
gaaactgata ttaattcaaa ggttgagaac aagatacagg aagatgtatt atcttcttta    600
caggatacat tcaagataag cagttatcct gattcactta tggaagaaac aagatccaga    660
cttgaaacat ctattggttt ctatgcggat ttttcaaatc tttcaaagga tgaatactgt    720
```

```
cagaagcagt atggactttc ttttgatgac tttgttaaga aatctgttgt acagcagctt    780
atcatggagg ctatagttaa agaccgcaat atgacaatga gagaatacga ttataaaggt    840
tctcttgatg attttgcggc agataatgga tattctaatg cggatacatt tgttgaaaaa    900
ttcggaaaag ataagattgt aaaggctatg cttgtgcaga aggcacagga ttatgttatt    960
gagcatgcca atatttctta taag                                           984

SEQ ID NO: 17           moltype = AA   length = 345
FEATURE                 Location/Qualifiers
source                  1..345
                        mol_type = protein
                        organism = Eubacterium eligens
SEQUENCE: 17
MKKTAVALLS VSMLMVTACN SKIDVKYDYN VEDYVQLGQY ENISVQVDKT SIENELIESK     60
IKQDVEDNTT YTEVDRGAIA SDQILVTYTA TSSGASLSGL TNTDGKTMIL GTDTLGLELD    120
ELDQALYGMT PGQTKILIVD IPEDYSSDLY KGTRVVFELT MQTVAQANVP MITNAYVKEA    180
FGYDTVEEYR QSIKESLETD INSKVENKIQ EDVLSSLQDT FKISSYPDSL MEETRSRLET    240
SIGFYADFSN LSKDEYCQKQ YGLSFDDFVK KSVVQQLIME AIVKDRNMTM REYDYKGSLD    300
DFAADNGYSN ADTFVEKFGK DKIVKAMLVQ KAQDYVIEHA NISYK                    345

SEQ ID NO: 18           moltype = DNA   length = 1035
FEATURE                 Location/Qualifiers
source                  1..1035
                        mol_type = other DNA
                        organism = Eubacterium eligens
SEQUENCE: 18
atgaagaaga cagcagttgc tttattatca gtttctatgc ttatggtaac ggcatgtaat     60
agtaagattg atgttaagta tgattataat gttgaagatt atgttcagct tggacagtat    120
gaaaacatat cagtccaggt agataaaact tcaatagaga atgaacttat agagagtaaa    180
attaaacagg atgtagaaga taatactact tatacagaag ttgacagagg tgcgatagct    240
tctgatcaga ttcttgttac atatactgct acatcttctg gcgcatctct tagcggactt    300
actaatacag atggtaaaac aatgattctt ggaacggata ctctcggact tgaacttgat    360
gagttagatc aggctttata tggtatgacc ccaggtcaga caaagatact tattgttgat    420
ataccctgagg attatagttc ggatttatat aagggcacga gggttgtatt tgaacttaca    480
atgcagacag ttgcacaggc aaatgttcca atgataacta atgcatatgt taaggaagcg    540
tttggatatg ataccgttga agaatataga cagtcaataa atggaatctct tgaaactgat    600
attaattcaa aggttgagaa caagatacag gaagatgtat tatcttcttt acaggataca    660
ttcaagataa gcagttatcc tgattcactt atggaagaaa caagatccag acttgaaaca    720
tctattggtt tctatgcgga ttttttcaaat ctttcaaagg atgaatactg tcagaagcag    780
tatggacttt cttttgatga ctttgttaag aaatctgttg tacagcagct tatcatggag    840
gctatagtta agaccgcaat atgacaatga gagaatacg attataaagg ttctcttgat    900
gattttgcgg cagataatgg atattctaat gcggatacat tgttgaaaaa attcggaaaa    960
gataagattg taaaggctat gcttgtgcag aaggcacagg attatgttat tgagcatgcc   1020
aatatttctt ataag                                                    1035

SEQ ID NO: 19           moltype = AA   length = 267
FEATURE                 Location/Qualifiers
source                  1..267
                        mol_type = protein
                        organism = Clostridium bartlettii
SEQUENCE: 19
EVDSSKEQAT SKDEKQVVVA TSVAITEILD RLGVEVSGVP QTSYELPESA KGATEIGSPM     60
NPDMEIIKSL NPTDVICVDT LGSDFEKQFE ENNINADFYN LSNVDGLKET IAALGEKFNK    120
QDKANEILDE IKEVENKVNS NKKSDDKILV LFGAPGSVMV ATDKSYIGNL VELAGGNNIF    180
SNATSSFTQI NLEEIIKLNP DKILVMTHAV PEAAKKSVEE ELSKDLWKNV NAVKNNDITY    240
LENGYFGMSA NLQIVEAVEK LGDILYE                                        267

SEQ ID NO: 20           moltype = DNA   length = 801
FEATURE                 Location/Qualifiers
source                  1..801
                        mol_type = other DNA
                        organism = Clostridium bartlettii
SEQUENCE: 20
gaggtagata gttctaaaga acaagctaca tcaaaagatg aaaaacaagt agtagtagct     60
acatcagttg caattactga aatattagat aggttaggtg tagaagttag tggtgtacca    120
caaactagct atgaacttcc agaaagtgca aaaggtgcta cggaaattgg aagtccaatg    180
aatccagata tggaaataat aaaatccacta atccaacag acgtaatatg tgttgatact    240
ttaggaagtg atttttgaaaa acaatttgaa gaaaacaata taaatgctga ttttttataat    300
ctaagcaatg tagacggatt aaaagaaaca atagctgctt taggagaaaa attcaataaa    360
caagataaag caaatgaaat attagatgaa ataaaagaag tagaaaataa agttaattct    420
aataaaaaaat ctgatgataa gatcttagta ttatttggag caccaggaag tgtaatggta    480
gctacggaca aaagttatat aggaaactta gtcgagttag ctggaggaaa taatatattc    540
tcaaatgcaa ctagctcatt tactcaaata aacttagaag aaataataaa gttaaatcca    600
gataaaatat tagttatgac tcatgccgtt ccagaggctg caaaaaaatc tgtagaagaa    660
gaattaagta aagcccttg gaaaaatgta aatgcagtta aaaataacga tataactyat    720
ttagaaaatg gttattcgg aatgagtgca aacttacaaa tagttgaggc agtagaaaaa    780
ttaggagata tattttatga g                                              801

SEQ ID NO: 21           moltype = AA   length = 268
FEATURE                 Location/Qualifiers
```

-continued

```
source                  1..268
                        mol_type = protein
                        organism = Clostridium bartlettii
SEQUENCE: 21
MEVDSSKEQA TSKDEKQVVV ATSVAITEIL DRLGVEVSGV PQTSYELPES AKGATEIGSP  60
MNPDMEIIKS LNPTDVICVD TLGSDFEKQF EENNINADFY NLSNVDGLKE TIAALGEKFN  120
KQDKANEILD EIKEVENKVN SNKKSDDKIL VLFGAPGSVM VATDKSYIGN LVELAGGNNI  180
FSNATSSFTQ INLEEIIKLN PDKILVMTHA VPEAAKKSVE EELSKDLWKN VNAVKNNDIT  240
YLENGYFGMS ANLQIVEAVE KLGDILYE                                   268

SEQ ID NO: 22           moltype = DNA  length = 804
FEATURE                 Location/Qualifiers
source                  1..804
                        mol_type = other DNA
                        organism = Clostridium bartlettii
SEQUENCE: 22
atggaggtag atagttctaa agaacaagct acatcaaaag atgaaaaaca agtagtagta  60
gctacatcag ttgcaattac tgaaatatta gataggttag gtgtagaagt tagtggtgta  120
ccacaaacta gctatgaact tccagaaagt gcaaaaggtg ctacggaaat tggaagtcca  180
atgaatccag atatggaaat aataaaatca ctaaatccaa cagacgtaat atgtgttgat  240
actttaggaa gtgattttga aaaacaattt gaagaaaaca atataaatgc tgatttttat  300
aatctaagca atgtagacgg attaaaagaa acaatagctg ctttaggaga aaaattcaat  360
aaacaagata aagcaaatga aatattagat gaaataaaag aagtagaaaa taaagttaat  420
tctaataaaa aatctgatga taagatctta gtattatttg gagcaccagg aagtgtaatg  480
gtagctacgg acaaaagtta tataggaaac ttagtcgagt tagctggagg aaataatata  540
ttctcaaatg caactagctc atttactcaa ataaacttag aagaaataat aaagttaaat  600
ccagataaaa tattagttat gactcatgcc gttccagagg ctgcaaaaaa atctgtagaa  660
gaagaattaa gtaaagacct ttggaaaaat gtaaatgcag ttaaaaataa cgatataact  720
tatttagaaa atggttattt cggaatgagt gcaaacttac aaatagttga ggcagtagaa  780
aaattaggag atatattata tgag                                       804

SEQ ID NO: 23           moltype = AA  length = 290
FEATURE                 Location/Qualifiers
source                  1..290
                        mol_type = protein
                        organism = Clostridium bartlettii
SEQUENCE: 23
MKKILCLISI LMVTFSVIGC SSSEVDSSKE QATSKDEKQV VVATSVAITE ILDRLGVEVS  60
GVPQTSYELP ESAKGATEIG SPMNPDMEII KSLNPTDVIC VDTLGSDFEK QFEENNINAD  120
FYNLSNVDGL KETIAALGEK FNKQDKANEI LDEIKEVENK VNSNKKSDDK ILVLFGAPGS  180
VMVATDKSYI GNLVELAGGN NIFSNATSSF TQINLEEIIK LNPDKILVMT HAVPEAAKKS  240
VEEELSKDLW KNVNAVKNND ITYLENGYFG MSANLQIVEA VEKLGDILYE            290

SEQ ID NO: 24           moltype = DNA  length = 870
FEATURE                 Location/Qualifiers
source                  1..870
                        mol_type = other DNA
                        organism = Clostridium bartlettii
SEQUENCE: 24
ttgaaaaaga ttttatgttt aatatcgatt ttgatggtta ctttttcagt aattggatgc  60
tcatctagcg aggtagatag ttctaaagaa caagctacat caaaagatga aaaacaagta  120
gtagtagcta catcagttgc aattactgaa atattagata ggttaggtgt agaagttagt  180
ggtgtaccac aaactagcta tgaacttcca gaaagtgcaa aaggtgctac ggaaattgga  240
agtccaatga atccagatat ggaaataata aaatcactaa atccaacaga cgtaatatgt  300
gttgatactt taggaagtga ttttgaaaaa caatttgaag aaaacaatat aaatgctgat  360
ttttataatc taagcaatgt agacggatta aaagaaacaa tagctgcttt aggagaaaaa  420
ttcaataaac aagataaagc aaatgaaata ttagatgaaa taaaagaagt agaaaataaa  480
gttaattcta ataaaaaatc tgatgataag atcttagtat tatttggagc accaggaagt  540
gtaatggtag ctacggacaa aagttatata ggaaacttag tcgagttagc tggaggaaat  600
aatatattct caaatgcaac tagctcattt actcaaataa acttagaaga aataataaag  660
ttaaatccag ataaaatatt agttatgact catgccgttc cagaggctgc aaaaaaatct  720
gtagaagaag aattaagtaa agacctttgg aaaaatgtaa atgcagttaa aaataacgat  780
ataacttatt tagaaaatgg ttatttcgga atgagtgcaa acttacaaat agttgaggca  840
gtagaaaaat taggagatat attatatgag                                 870

SEQ ID NO: 25           moltype = AA  length = 279
FEATURE                 Location/Qualifiers
source                  1..279
                        mol_type = protein
                        organism = Clostridium bartlettii
SEQUENCE: 25
MVTFSVIGCS SSEVDSSKEQ ATSKDEKQVV VATSVAITEI LDRLGVEVSG VPQTSYELPE  60
SAKGATEIGS PMNPDMEIIK SLNPTDVICV DTLGSDFEKQ FEENNINADF YNLSNVDGLK  120
ETIAALGEKF NKQDKANEIL DEIKEVENKV NSNKKSDDKI LVLFGAPGSV MVATDKSYIG  180
NLVELAGGNN IFSNATSSFT QINLEEIIKL NPDKILVMTH AVPEAAKKSV EEELSKDLWK  240
NVNAVKNNDI TYLENGYFGM SANLQIVEAV EKLGDILYE                       279

SEQ ID NO: 26           moltype = DNA  length = 837
FEATURE                 Location/Qualifiers
```

```
source          1..837
                mol_type = other DNA
                organism = Clostridium bartlettii
SEQUENCE: 26
atggttactt tttcagtaat tggatgctca tctagcgagg tagatagttc taaagaacaa   60
gctacatcaa aagatgaaaa acaagtagta gtagctacat cagttgcaat tactgaaata  120
ttagataggt taggtgtaga agttagtggt gtaccacaaa ctagctatga acttccagaa  180
agtgcaaaag gtgctacgga aattggaagt ccaatgaatc cagatatgga aataataaaa  240
tcactaaatc caacagacgt aatatgtgtt gatactttag gaagtgattt tgaaaaacaa  300
tttgaagaaa acaatataaa tgctgatttt tataatctaa gcaatgtaga cggattaaaa  360
gaaacaatag ctgctttagg agaaaaattc aataaacaag ataaagcaaa tgaaatatta  420
gatgaaataa aagaagtaga aaataaagtt aattctaata aaaaatctga tgataagatc  480
ttagtattat ttggagcacc aggaagtgta atggtagcta cggacaaaag ttatatagga  540
aacttagtcg agttagctgg aggaaataat atattctcaa atgcaactag ctcatttact  600
caaataaact tagaagaaat aataaagtta aatccagata aaatattagt tatgactcat  660
gccgttccag aggctgcaaa aaaatctgta gaagaagaat taagtaaaga cctttggaaa  720
aatgtaaatg cagttaaaaa taacgatata acttatttag aaaatggtta tttcggaatg  780
agtgcaaact tacaaatagt tgaggcagta gaaaaattag gagatatatt atatgag    837
```